(12) United States Patent
Takemura et al.

(10) Patent No.: US 7,428,468 B2
(45) Date of Patent: Sep. 23, 2008

(54) MONITORING APPARATUS

(75) Inventors: Yasuhiro Takemura, Tokyo (JP);
Toshiharu Takesue, Tokyo (JP);
Kazuhiro Mimura, Tokyo (JP); Kei Katou, Tokyo (JP); Masato Nakajima, Yokohama (JP)

(73) Assignees: Sumitomo Osaka Cement Co., Ltd., Tokyo (JP); Keio University, Tokyo (JP)

( * ) Notice: Subject to any disclaimer, the term of this patent is extended or adjusted under 35 U.S.C. 154(b) by 974 days.

(21) Appl. No.: 10/480,782

(22) PCT Filed: Jun. 17, 2002

(86) PCT No.: PCT/JP02/06020

§ 371 (c)(1),
(2), (4) Date: Mar. 15, 2004

(87) PCT Pub. No.: WO02/102242

PCT Pub. Date: Dec. 27, 2002

(65) Prior Publication Data

US 2004/0210155 A1      Oct. 21, 2004

(30) Foreign Application Priority Data

Jun. 15, 2001    (JP)    ............... 2001-181077
Feb. 6, 2002     (JP)    ............... 2002-029406
Mar. 29, 2002    (JP)    ............... 2002-096209

(51) Int. Cl.
*G06F 19/00*    (2006.01)

(52) U.S. Cl. ................. 702/159; 342/118; 708/300

(58) Field of Classification Search .............. 702/105, 702/182–185, 188, 159, 179, 150, 152, 153, 702/181, 187; 455/3.02, 12.1, 13.1, 24, 98, 455/115; 706/17, 21; 701/207, 213, 226; 342/118, 135, 352, 357.01, 357.03, 357.08; 708/300

See application file for complete search history.

(56) References Cited

U.S. PATENT DOCUMENTS 5,334,831 A * 8/1994 Maurice ............... 250/227.17

FOREIGN PATENT DOCUMENTS

| JP | 3-4208 B2 | 1/1991 |
| JP | 3-4209 B2 | 1/1991 |
| JP | 4-71905 U | 6/1992 |
| JP | 6-205762 A | 7/1994 |
| JP | 11-276443 A | 10/1999 |
| JP | 2000-105281 A | 4/2000 |
| JP | 2000-217802 A | 8/2000 |
| JP | 2001-037739 A | 2/2001 |
| JP | 2001-070256 A | 3/2001 |
| JP | 2002-214327 A | 7/2002 |

* cited by examiner

*Primary Examiner*—Edward Raymond
(74) *Attorney, Agent, or Firm*—Foley & Lardner LLP

(57) ABSTRACT

To provide a monitoring device which can detect conditions of a sleeping person reliably and which is simple. A monitoring device comprising: multiple independent distance sensors 11 installed facing different positions in a monitored target area 50 to be monitored for measuring a distance to a monitored target 2, a calculating unit 22 for calculating changes over time in the outputs of the distance sensors 11, and a detection processor 23 for detecting changes in shape of the monitored target 2 based on the calculated changes over time in one or multiple distance sensor 11 among the multiple distance sensors 11.

48 Claims, 26 Drawing Sheets

FIG.2
(a)
(b)
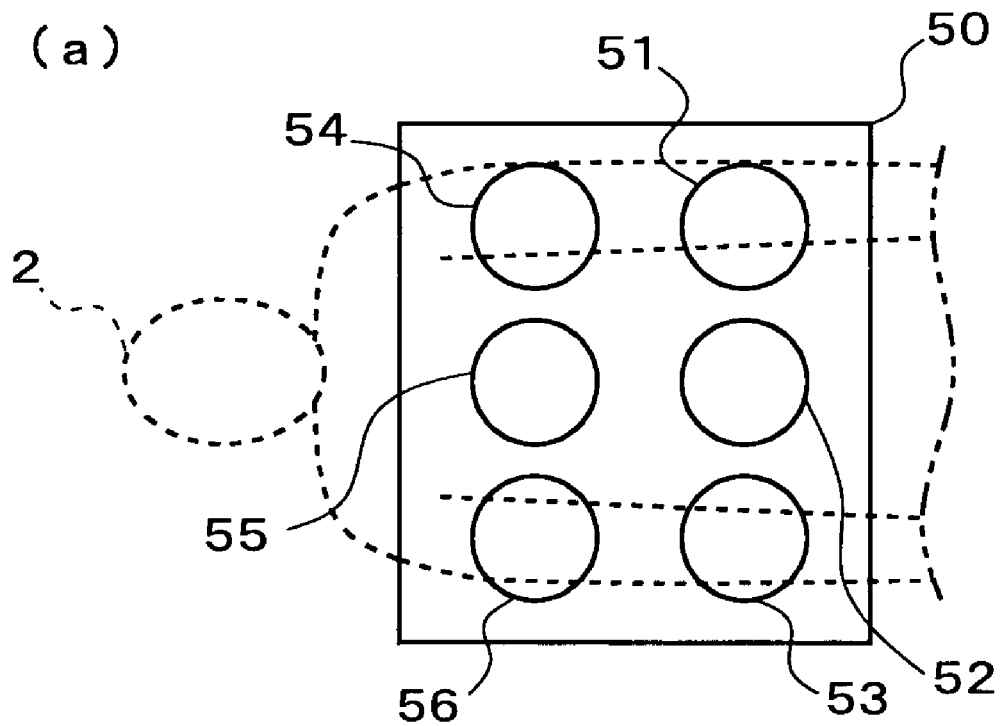
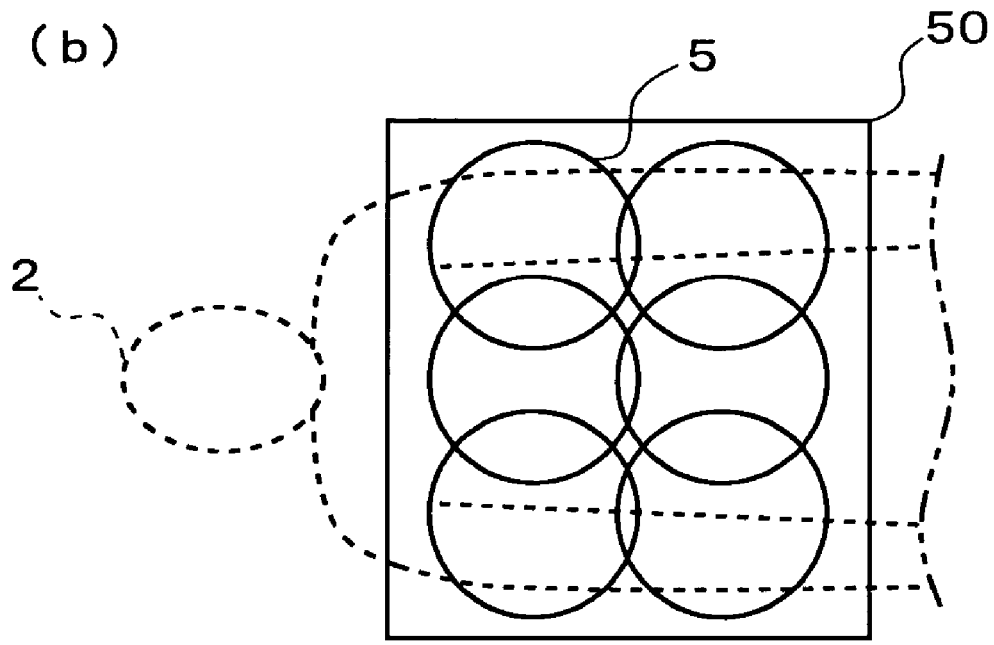

38

Imaging pattern 38c
38a
38b

FIG.8

| Distance to target | Pattern diameter | Position of center of gravity of imaging pattern | Entire area of imaging pattern | Area of region A | Area of region A / Area of region B |
|---|---|---|---|---|---|
| 2000 | 1.282 | 0.00000 | 1.291 | 0.645 | 0.998 |
| 1999 | 1.283 | 0.00255 | 1.292 | 0.643 | 0.991 |
| 1995 | 1.285 | 0.01278 | 1.298 | 0.632 | 0.949 |
| 1990 | 1.289 | 0.02563 | 1.304 | 0.619 | 0.904 |
| 1950 | 1.316 | 0.13077 | 1.360 | 0.509 | 0.598 |

[Unit: mm]

Baseline length: 200 mm
Beam light diameter: 50 mm
Sensor installation height: 2000 mm
Focal distance: 50 mm
Image distance: 51.0 mm Size of Bipartite PD: 4 mm × 4 mm × 2

FIG.14
(a)
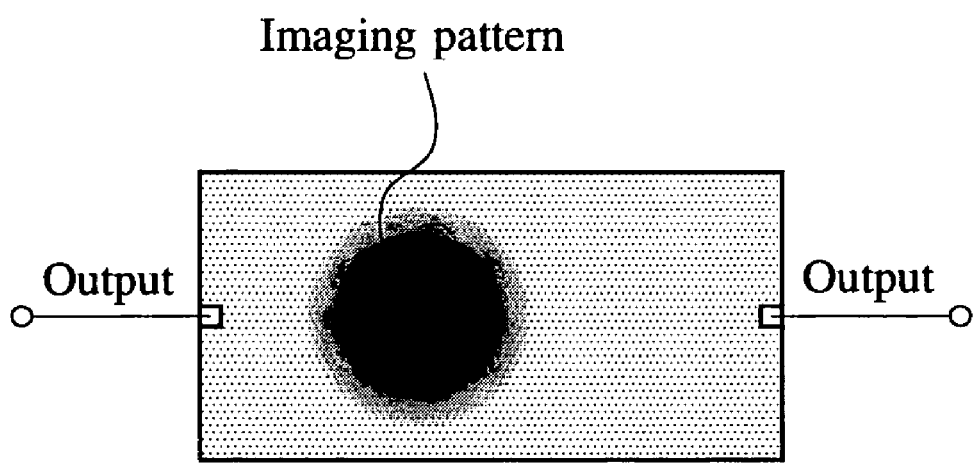
(b)
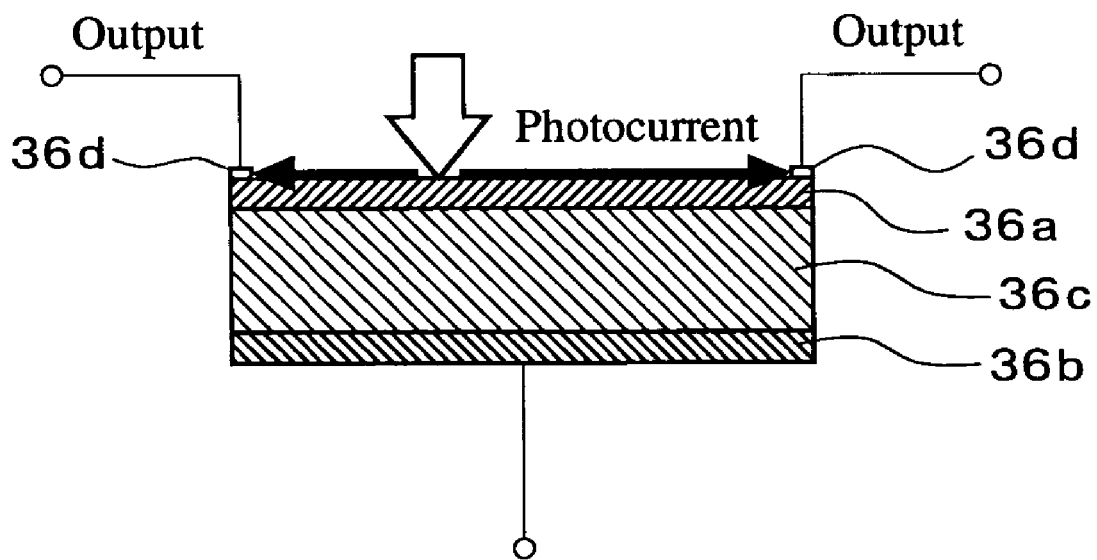

FIG.18
(a)
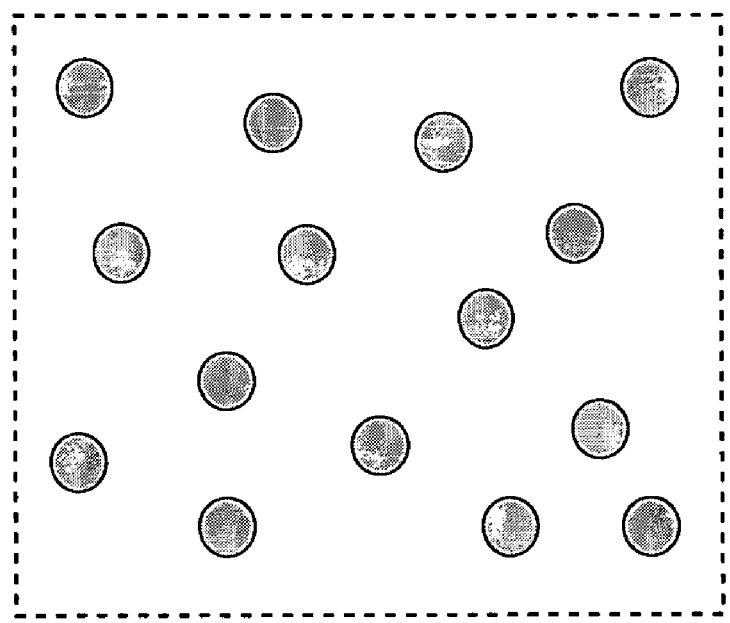
(b)
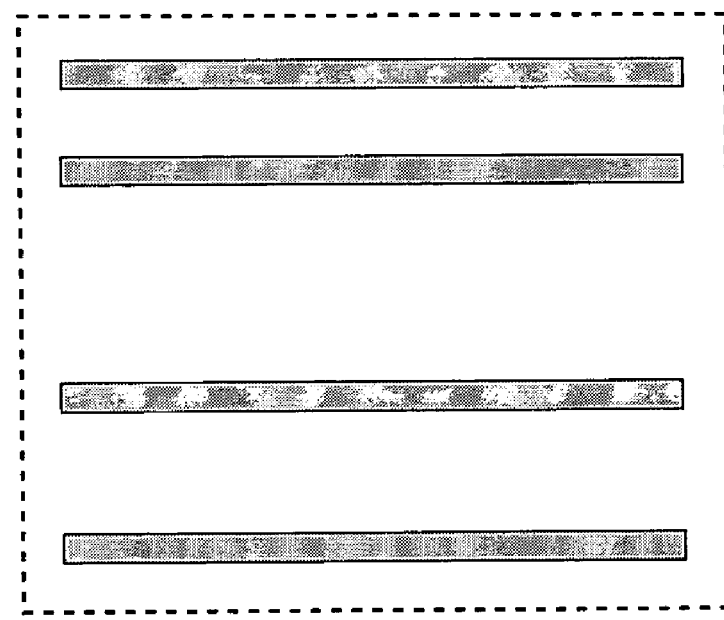

FIG.21
(a)
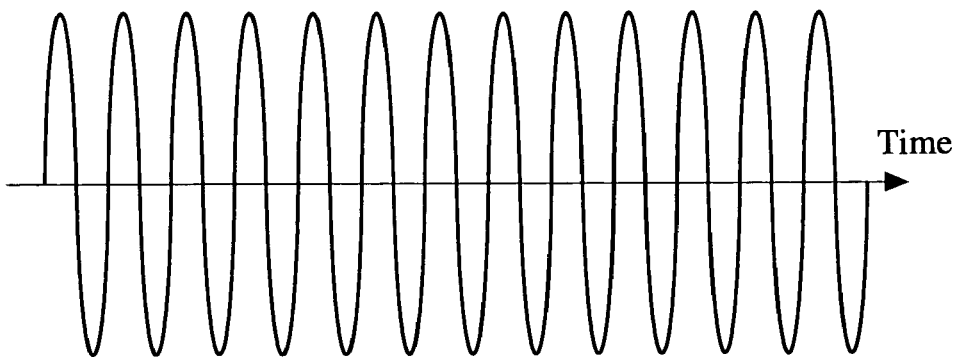
(b)
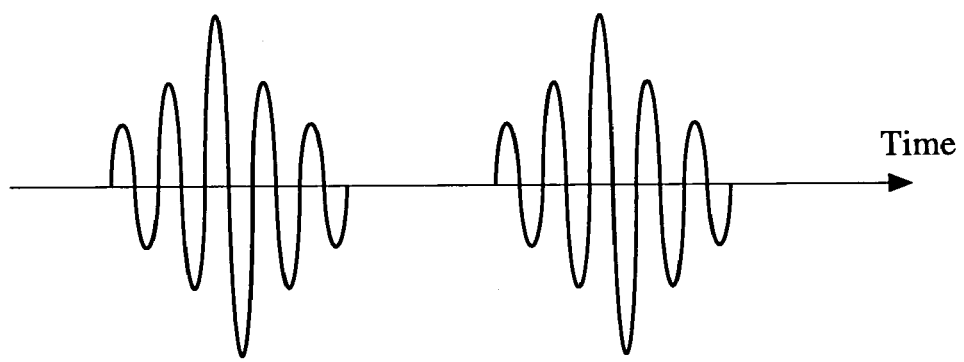
(c)
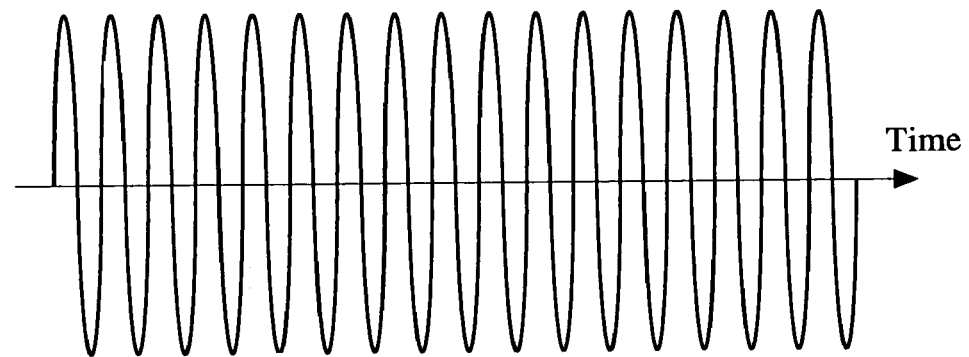
(d)
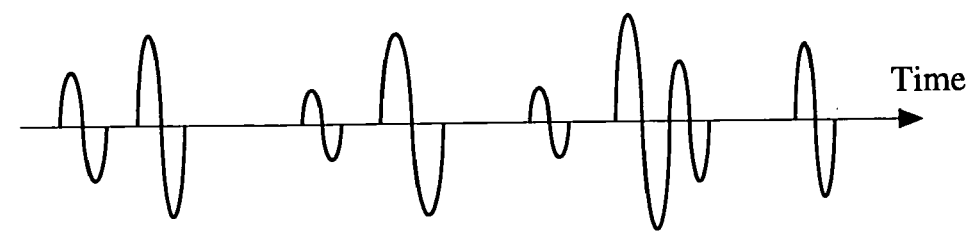

FIG.22

| Cheyne-Stokes respiration | Disorder in part under celebral cortex on both sides and in diencephalons. |
|---|---|
| Central hyperventilation | Disorder in part from lower mesencephalon to upper pons. |
| Ataxic respiration | Disorder in part from lower pons to upper medulla oblongata. |
| Kussmaul respiration | Diabetic coma or uremia. |

FIG.23
(a)
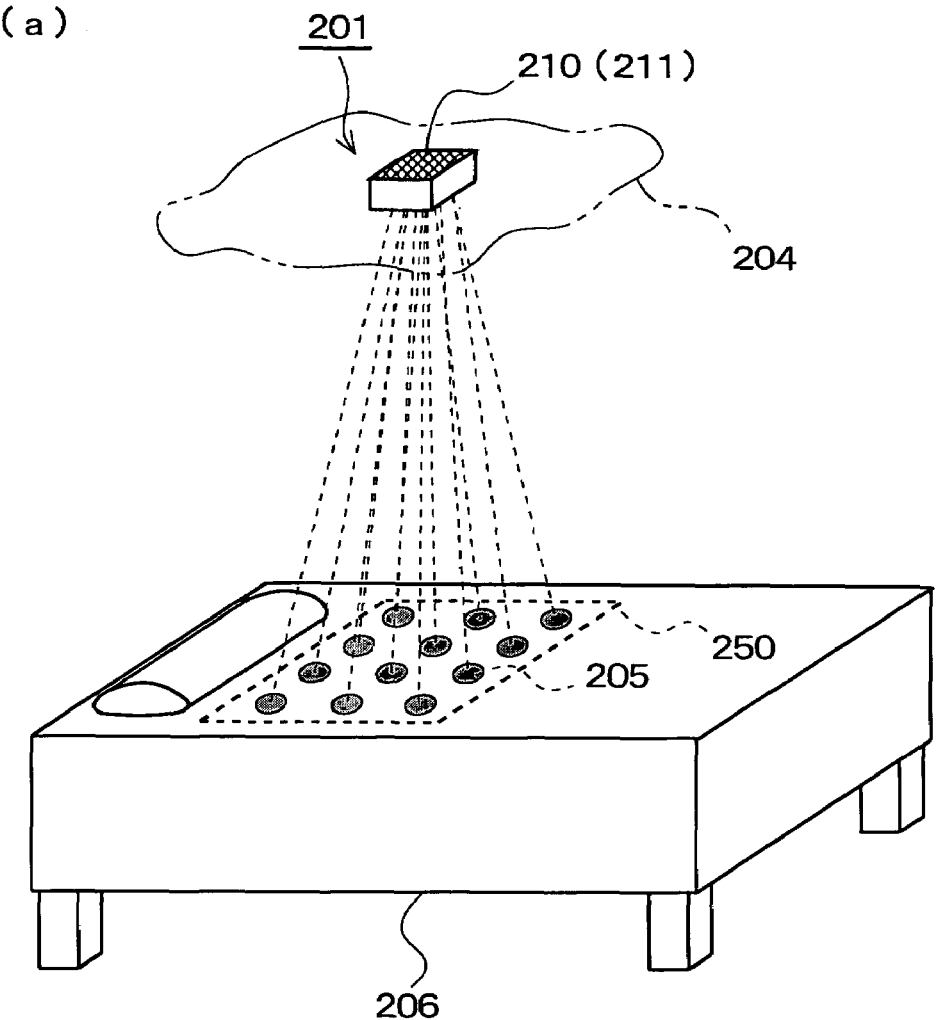
(b)
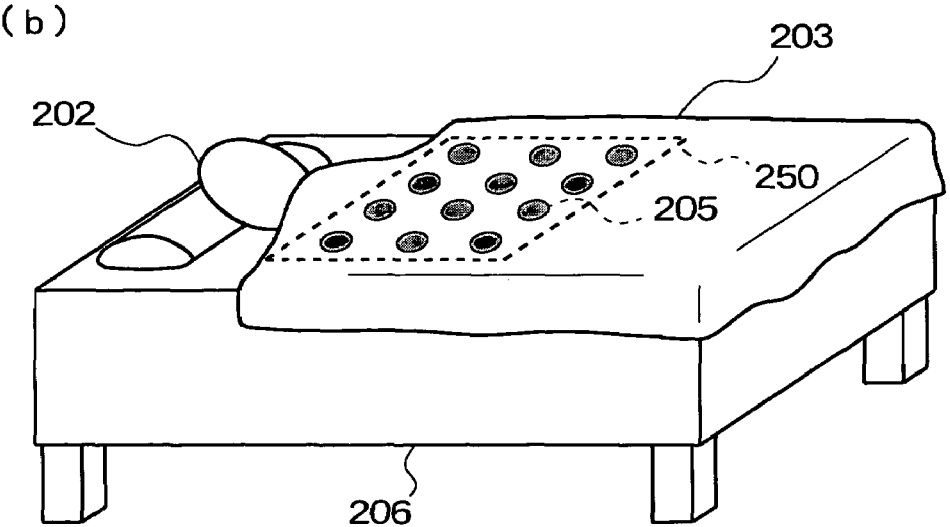

FIG.25
(a)
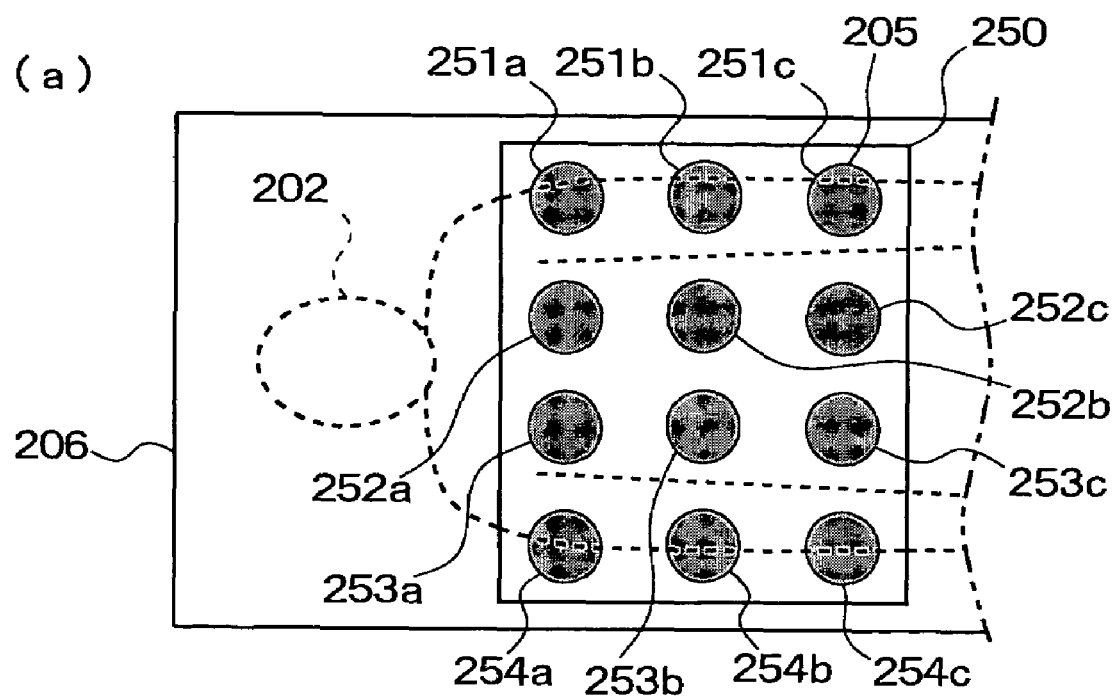
(b)
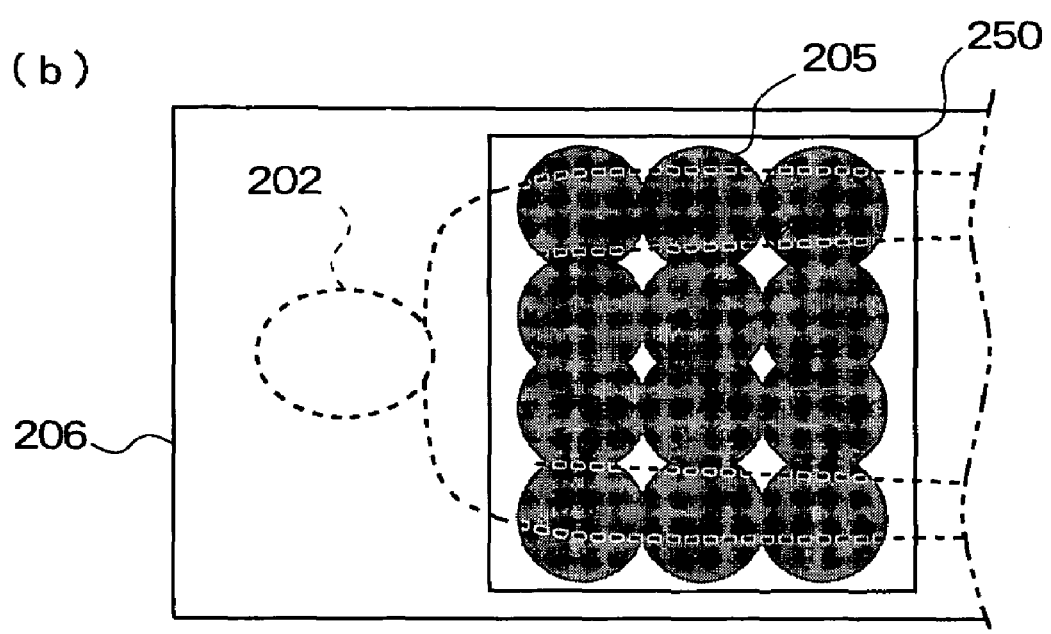

US 7,428,468 B2

MONITORING APPARATUS

TECHNICAL FIELD

This invention relates to a monitoring device and a monitoring method for monitoring a monitored target and, more particularly, to a monitoring device and a monitoring method for monitoring changes in respiration or the like of a sleeping person.

BACKGROUND ART

As a monitoring device for monitoring changes in respiration of a sleeping person, there has been conventionally proposed a device which monitors changes in respiration of a sleeping person based on changes over time in pressure distribution detected by load sensors or pressure sensors.

Such a conventional device, however, needs a high-performance signal amplifier or some signal processing means to obtain and detect stable signals since measured signals are weak. Thus, the device is complicated and large as a system.

It is, therefore, an object of this invention to provide a monitoring device which can detect conditions of a sleeping person reliably and which is simple.

DISCLOSURE OF THE INVENTION

An object of this invention is to provide a monitoring device comprising: a distance sensor 11 installed facing a monitored target area 50 for measuring the distance to a monitored target 2; a calculating unit 22 for calculating changes over time in the output of the distance sensor 11; and a detection processor 23 for detecting changes in shape of the monitored target 2 based on the calculated changes over time as shown, for example, in FIG. 1 and FIG. 3.

An object of this invention is to provide a monitoring device comprising: multiple independent distance sensors 11 installed facing different positions respectively in a monitored target area 50 for measuring the distance to a monitored target 2; a calculating unit 22 for calculating the changes over time in the outputs of each of the multiple distance sensors 11; and a detection processor 23 for detecting changes in shape of the monitored target 2 based on the calculated changes over time in one or multiple selected distance sensors 11 among the multiple distance sensors 11 as shown, for example, in FIG. 1 and FIG. 3.

The monitoring device 1 constituted as described above has multiple distance sensors 11, a calculating unit 22 and a detection processor 23. The multiple distance sensors 11 measure the distances to the monitored target 2 in the monitored target area 50, and the changes over time in the outputs of each of the multiple distance sensors 11 is calculated. Then, changes in shape of the monitored target 2 are detected based on the calculated changes over time in one or multiple selected distance sensors 11 among the multiple distance sensors 11. The monitoring device 1 can therefore reliably detect the condition of a sleeping person.

The monitoring device 1 preferably determines the condition of the monitored target based on the detected changes in shape of the monitored target 2.

In the monitoring device 1, the detection processor 23 preferably determines that the monitored target 2 is in the monitored target area 50 when periodic changes in the detected changes in shape has continued for a predetermined period of time or longer. The monitoring device 1 can therefore determine that a sleeping person, for example, is in bed.

In the monitoring device 1, the detection processor 23 preferably determines that the monitored target 2 has deviated from the monitored target area 50 when no periodic change is detected after a transitional change has been detected in the detected changes in shape and neither transitional change nor periodic change can be detected for a predetermined period of time or longer. The monitoring device 1 can therefore determine that a sleeping person, for example, has left bed.

In the monitoring device 1, the detection processor 23 may determine the condition of the monitored target 2 based on either or both of the period and amplitude of periodic changes in the detected changes in shape. A target, which shows periodic changes, is a concept including an animal such as a human.

In the monitoring device 1, the detection processor 23 may select an output which showed the largest change over time within a predetermined period of time in the immediate past and detect changes in shape of the monitored target 2 based on change over time in the output.

In the monitoring device 1, the detection processor 23 may select all of the multiple distance sensors 11, obtain the total of changes over time in the distances, and detect changes in shape of the monitored target 2 based on the total.

In the monitoring device 1, the detection processor 23 may calculate the frequency spectra of all the outputs from the multiple distance sensors 11, select a distance sensor 11 whose output has a frequency spectrum with a peak having a sharpness which is a predetermined value or higher and the highest among the calculated frequency spectra, and detect changes in shape of the monitored target 2 based on changes over time in the selected distance sensor 11.

In the monitoring device 1, the detection processor 23 preferably calculates the frequency spectra of outputs from the distance sensors 11 which detected a change over time having an absolute value within a predetermined range, selects a distance sensor 11 whose output has a frequency spectrum with a peak having a sharpness which is a predetermined value or higher and the highest among the calculated frequency spectra, and detects changes over time in shape of the monitored target 2 based on changes over time in the selected distance sensor 11.

In the monitoring device 1, the detection processor 23 preferably calculates the frequency spectra of outputs from a plurality of the distance sensors 11 which detected a change over time having one of the largest absolute values, selects a distance sensor 11 whose output has a frequency spectrum with a peak having a sharpness which is a predetermined value or higher and the highest among the calculated frequency spectra, and detects changes in shape of the monitored target 2 based on changes over time in the selected distance sensor 11.

In the monitoring device 1, the detection processor 23 may select changes over time having absolute values which are larger than a predetermined value and detect changes in shape of the monitored target 2 based on the average of the selected changes over time.

In the monitoring device 1, the detection processor 23 may select changes over time having absolute values which are larger than a predetermined value and detect changes in shape of the monitored target 2 based on the average of the absolute values of the selected changes over time.

In the monitoring device 1, the detection processor 23 may compare the phases of changes over time relating to a plurality of the selected distances each other, classify the changes over time into groups according to the similarity of the phases, obtain the total of the changes over time in each group, calculate the difference between the totals of groups, the groups having approximately opposite phases each other, and detect changes in shape of the monitored target 2 based on the value obtained by the calculation.

The monitoring device 1 has light emitting means 31a for emitting a light flux to the monitored target 2 and an imaging optical system 37a for forming an image of light emission pattern generated on the monitored target 2 by the light emitting means 31a, and obtains an output corresponding to the distance by trigonometry based on the position where imaging pattern light is formed into an image by the imaging optical system 37a as shown, for example, in FIG. 5.

In the monitoring device 1, the distance sensor 11 may have at least two imaging units 41 and 42 for forming images of the monitored target 2 by individual optical axes and obtains an output corresponding to the distance by trigonometry based on information on the position where the images are formed from the imaging units 41 and 42 as shown, for example, in FIG. 17.

An object of this invention is to provide a monitoring method comprising the steps of: measuring a distances to multiple different positions within a monitored target area to measure the distances to a monitored target changing in shape within said monitored area; calculating changes over time in the multiple distances; and detecting changes in shape of the monitored target based on the calculated changes over time in one or multiple selected distances among changes over time. In the distance measuring step, typically, the distances from one point to multiple different positions in the monitored target area are preferably measured. The one point here is a concept including a plurality of points in the vicinity.

Preferably in the monitoring method, an output which showed the largest change over time within a predetermined period of time in the immediate past is selected and changes in shape of the monitored target are detected based on change over time in the output in the step of detecting.

Preferably in the monitoring method, all the multiple distances are selected, the total of all the changes over time in the distances is obtained, and changes in shape of the monitored target are detected based on the total in the step of detecting.

Preferably in the monitoring method, changes over time having absolute values which are larger than a predetermined value are selected and changes in shape of the monitored target are detected based on the average of the selected changes over time in the step of detecting.

Preferably in the monitoring method, changes over time having absolute values which are larger than a predetermined value are selected and changes in shape of the monitored target are detected based on the average of the absolute values of the selected changes over time in the step of detecting.

Preferably in the monitoring method, the phases of changes over time relating to a plurality of the selected distances are compared each other, the changes are classified into groups according to the similarity of the phases, the total of the changes over time in each group is obtained, the difference between the totals of the groups, the groups having approximately opposite phases each other, is calculated, and changes in shape of the monitored target are detected based on the value obtained by the calculation in the step of detecting. In the step of detecting, all the changes over time in the multiple distances may be selected or changes over time having absolute values, which are greater than a predetermined value may be selected.

Another object of this invention is to provide a monitoring device comprising: a distance sensor 11 for measuring a distance to a monitored target 2 to be monitored to in a monitored target area 50; a calculating unit 22 for calculating changes over time in the output from the distance sensor 11; and a detection processor 23 for detecting a changes in shape of the monitored target 2 based on the calculated changes over time; wherein the distance sensor 11 has light emitting means 31a for emitting a light flux to the monitored target 2, an imaging optical system 37a for forming an image of a light emission pattern generated on the monitored target 2 by the light emitting means 31a; and a light receiving surface 38 disposed in the vicinity of the position where the imaging optical system 37a forms an image and divided into a plurality of light receiving regions 38a and 38b for receiving imaging pattern light from the formed image of the light emission pattern; and further has a position information output unit 39a for receiving signals from the light receiving regions 38a and 38b, comparing the intensities of imaging pattern lights incident on the light receiving regions 38a and 38b based on the receiving signals, and outputting information on the position where an imaging pattern is formed corresponding to the distance to the monitored target 2 as shown, for example, in FIG. 1, FIG. 3 and FIG. 5. The changes in shape are typically continuous changes in shape.

The monitoring device 1 constituted as described above has a distance sensor 11, a calculating unit 22 and a detection processor 23. The distance sensor 11 measures the distance to the monitored target 2 in the monitored target area 50, and changes over time in the output from the distance sensor 11 are calculated. Then, changes in shape of the monitored target 2 are detected based on the calculated changes over time. The monitoring device 1 can therefore reliably detect the condition of a sleeping person. Also, the distance sensor 11 has a light emitting means 31a, an imaging optical system 37a and a light receiving surface 38 divided into a plurality of light receiving regions 38a and 38b. Thus, the circuit configuration can be simplified and the monitoring device 1 can be cost-effective and simple.

Another object of this invention is to provide a monitoring device comprising: a distance sensor 11 for measuring the distance to a monitored target 2 to be monitored in a monitored target area 50; a calculating unit 22 for calculating changes over time in the output from the distance sensor 11; and a detection processor 23 for detecting changes in shape of the monitored target 2 based on the calculated changes over time; wherein the distance sensor 11 has light emitting means 31b for emitting a light flux to the monitored target 2, an imaging optical system 37b for forming an image of light emission pattern generated on the monitored target 2 by the light emitting means 31b, light receiving means 36 disposed in the vicinity of the position where the imaging optical system 37b forms an image for receiving imaging pattern light from the formed image of the light emission pattern; and a position information output unit 39b for outputting information on the position where an imaging pattern is formed corresponding to the distance to the monitored target 2 based on the position where imaging pattern light is formed into an image on the light receiving means 36 as shown, for example, in FIG. 1, FIG. 3 and FIG. 13.

The monitoring device 1 constituted as described above has a distance sensor 11, a calculating unit 22 and a detection processor 23. The distance sensor 11 measures the distance to the monitored target 2 in the monitored target area 50, and changes over time in the output from the distance sensor 11 are calculated. Then, changes in shape of the monitored target 2 are detected based on the calculated changes over time. The monitoring device 1 can therefore reliably detect the condition of a sleeping person. Also, the distance sensor 11 has a light emitting means 31b, an imaging optical system 37b and light receiving means 36 and outputs information on the position where an imaging pattern is formed corresponding to the distance to the monitored target 2 based on the position where imaging pattern light is formed into an image on the light receiving means 36. Thus, the monitoring device 1 can be cost-effective and simple.

In the monitoring device, the monitored target 2 is a target which shows periodic changes, and the detection processor 23 preferably monitors the period of the periodic changes based on the detected changes in shape of the monitored target 2. The target which shows periodic changes is a concept including an animal such as a human.

Since the monitoring device 1 constituted as described above monitors the respiration rate of the monitored target 2, the condition of a sleeping person can be detected reliably.

The monitoring device 1 described above has a plurality of distance sensors 11, and the plurality of distance sensors 11 are independent respectively and installed facing to different positions in the monitored target area 50. Since the monitoring device constituted as described above has a plurality of distance sensors 11, the condition of a sleeping person can be detected reliably.

In the monitoring device 1, the detection processor 23 selects a distance sensor 11 which detected the largest change over time within a predetermined period of time in the immediate past and detect changes in shape of the monitored target 2 based on the change over time.

In the monitoring device 1, the detection processor 23 may select all of the plurality of distance sensors 11, obtain the total of changes over time in the distances, and detect changes in shape of the monitored target 2 based on the total.

In the monitoring device 1, the detection processor 23 may select changes over time having absolute values, which are greater than a predetermined value and detect changes in shape of the monitored target 2 based on the average of the selected changes over time.

In the monitoring device 1, the detection processor 23 may select changes over time having absolute values which are greater than a predetermined value and detect changes in shape of the monitored target 2 based on the average of the absolute values of the selected changes over time.

In the monitoring device 1, the detection processor 23 may compare the phases of the changes over time relating to the a plurality of selected distance sensors 11 each other, and classify the changes into groups according to the similarity of the phases, obtain the total of the changes over time in each group and calculate the difference between the totals of the groups, the groups having approximately opposite phases each other, and detect changes in shape of the monitored target 2 based on the value obtained by the calculation.

Another object of this invention is to provide a monitoring device comprising a sensor 211 for detecting a variable correlating to a distance to a monitored target 202 in a monitored target area 250; a calculating unit 222 for calculating a distance-related value based on the variable output from the sensor 211; and a determination unit 223 for determining if there are changes in shape of the monitored target 202 based on the distance-related value; wherein the determination unit 223 determines that the monitored target 202 has had a first change in shape when the distance-related value is the same or larger than a first threshold value $Th_{1x}$ and lower than a second threshold value $Th2_x$, with the second threshold value being larger than the first threshold value $Th_{1x}$; and wherein the determination unit 223 determines that the monitored target 202 has had a second change in shape, which is different from the first change in shape, when the distance-related value is the same or larger than the second threshold value $Th_{2x}$ and lower than a third threshold value $Th_{3x}$, with the third threshold value being larger than the second threshold value $Th_{2x}$ as shown, for example, in FIG. 23 and FIG. 26. The monitored target 202 is a sleeping person, for example.

The monitoring device 201 constituted as described above has a sensor 211, a calculating unit 222 and a determination unit 223, and the determination unit 223 determines that the monitored target 202 has had a first change in shape when the distance-related value is the same or larger than a first threshold value $Th_{1x}$ and lower than a second threshold value $Th_{2x}$, with the second threshold value being larger than the first threshold value $Th_{1x}$. Thus, for example, the respiration of the sleeping person can be detected. Also, the determination unit 223 determines that the monitored target 202 has had a second change in shape, which is different from the first change in shape, when the distance-related value is the same or larger than the second threshold value $Th_{2x}$ and lower than a third threshold value $Th_{3x}$, with the third threshold value being larger than the second threshold value $Th_{2x}$. Thus, for example, motion of a sleeping person can be detected. There can be therefore provided a monitoring device 201 which can detect changes of the sleeping person precisely and is simple.

In the monitoring device 201, the determination unit 223 preferably determines that the monitored target 202 has deviated from the monitored target area 250 when no change in shape of the monitored target 202 can be detected within a first predetermined period of time after the distance-related value has exceeded the third threshold value $Th_{3x}$.

The monitoring device 201 constituted as described above determines that the monitored target 202 has deviated from the monitored target area 250 when no change in shape of the monitored target 202 can be detected within a first predetermined period of time after the distance-related value has exceeded the third threshold value $Th_{3x}$. The monitoring device 201 can therefore, for example, determine that a sleeping person has left bed.

In the monitoring device 201, the determination unit 223 is preferably configure to determine that the monitored target 202 has deviated from the monitored target area 250 when neither the first change in shape nor the second changes in shape of the monitored target 202 can be detected within a predetermined period of time without detection of periodic changes after the distance-related value has exceeded the third threshold value $Th_{3x}$. Also, the monitored target 202 is a target, which shows periodic changes, and a target, which shows periodic changes, is a concept including an animal such as a human.

In the monitoring device 201, the determination unit 223 preferably determines that there has been a third change in shape when periodic changes in the distance-related value are detected.

The monitoring device 201 constituted as described above, for example, can detect the respiration of a sleeping person precisely. Also, the determination unit 223 monitors the period of the periodic changes based on the detected periodic changes. The period is a concept including the respiration rate of a sleeping person.

In the monitoring device 201, the determination unit 223 preferably determines that the monitored target 202 is in the monitored target area 250 when changes in shape of the monitored target 202 are determined to have continued for a second predetermined period of time.

The monitoring device 201 constituted as described above determines that the monitored target 202 is in the monitored target area 250 when changes in shape of the monitored target 202 are determined to have continued for a second predetermined period of time. The monitoring device 202, for example, can therefore determine that a sleeping person is in bed.

In the monitoring device 201, the determination unit 223 may determine that the monitored target 202 is in the monitored target area 250 when periodic changes in the distance-related value has been detected for a predetermined period of time. The monitoring device 201 constituted as described above determines that the monitored target 202 is in the monitored target area 250 when periodic changes in the distance-related value has been detected for a predetermined period of time. The monitoring device 202, for example, can therefore determine that a sleeping person is in bed.

In the monitoring device 201, the determination unit 223 preferably determines that the monitored target 202 has no changes in shape when the distance-related value is lower than the first threshold value $Th_{1x}$ and determines that the monitored target 202 is in a critical condition when the monitored target 202 is determined to have had no change in shape for a third predetermined period of time after the monitored target 202 has been determined to be in the monitored target area 250.

The monitoring device 201 constituted as described above determines that the monitored target 202 is in a critical condition when the monitored target 202 is determined to have had no change in shape for a third predetermined period of time after the monitored target 202 has been determined to be in the monitored target area 250. Thus, for example, a critical condition of a sleeping person such as respiratory arrest can be determined with high reliability.

In the monitoring device 201, the determination unit 223 preferably determines that the monitored target 202 is in a critical condition when the second change in shape is determined to have continued for a fourth predetermined period of time.

The monitoring device 201 constituted as described above determines that the monitored target 202 is in a critical condition when the second change in shape is determined to have continued for a fourth predetermined period of time. The monitoring device 201, for example, can therefore determine that a sleeping person is in a critical condition, such as when the person is suffering and struggling, with high reliability.

Preferably, the monitoring device 201 is provided with alarm means 290 for issuing an alarm; and the determination unit 223 to sends an alarm signal to the alarm means 290 when the monitored target 202 is determined to be in a critical condition.

The monitoring device 201 constituted as described above is provided with alarm means 290, and the determination unit 223 sends an alarm signal to the alarm means 290 when the monitored target 202 is determined to be in a critical condition. Since, for example, the monitoring device 201 can issue an alarm when a sleeping person is in a critical condition, it has high reliability.

Another object of this invention is to provide a monitoring device comprising a sensor 211 for detecting a variable correlating the distance to a monitored target 202 in a monitored target area 250; a calculating unit 222 for calculating a distance-related value based on the variable output from the distance sensor 211; and a determination unit 223 for determining if there are changes in shape of the monitored target 202 based on the calculated distance-related value; wherein the determination unit 223 determines that the monitored target 202 has deviated from the monitored target area 250 when no change in shape of the monitored target 202 can be detected within a first predetermined period of time after the distance-related value has exceeded the third threshold value $Th_{3x}$ as shown, for example, in FIG. 23 and FIG. 26.

The monitoring device constituted as described above has a sensor 211, a calculating unit 222 and a determination unit 223. The distance-related value is calculated based on the variable output from the sensor 211 and the presence or absence of changes in shape of the monitored target 202 is determined based on the calculated distance-related value. The monitoring device, for example, can therefore detect changes in a sleeping person. Also, the determination unit 223 determines that the monitored target 202 has deviated from the monitored target area 250 when no change in shape of the monitored target 202 can be detected within a first predetermined period of time after the distance-related value has exceeded the third threshold value $Th_{3x}$. The monitoring device, for example, can therefore detect the fact that a sleeping person has left bed. There can be therefore provided a monitoring device 201 which can reliably detect changes in a person and is simple.

In the monitoring device 201, the determination unit 223 preferably determines that the monitored target 202 has had a fourth change in shape when the distance-related value exceeds the third threshold value $Th_{3x}$.

The monitoring device 201 constituted as describe above determines that the monitored target 202 has had a fourth change in shape when the distance-related value exceeds a third threshold value $Th_{3x}$. The monitoring device 201, for example, therefore can detect motion of a sleeping person such as sitting-up.

In the monitoring device 201, the calculated distance-related value is preferably changes over time in the variable or the absolute value of the changes over time.

In the monitoring device 201, the sensor 211 (30a) has light emitting means 31a for emitting a light flux to the monitored target 202, an imaging optical system 37a for forming an image of light emission pattern generated on the monitored target 202 by the light emitting means 31a, a light receiving surface 38 disposed in the vicinity of the position where the imaging optical system 37a forms an image and divided into a plurality of light receiving regions 38a and 38b for receiving imaging pattern light from the formed image of the light emission pattern; and a position information output unit 39a for receiving signals from the light receiving regions 38a and 38b, comparing the intensities of imaging pattern lights incident on the light receiving regions 38a and 38b based on the receiving signals, and outputting information on the position where an imaging pattern is formed corresponding to the distance to the monitored target 202 as shown, for example, in FIG. 5, FIG. 6 and FIG. 23.

In the monitoring device 201 constituted as described above, the distance sensor 211 (30a) has a light emitting means 31a, an imaging optical system 37a and a light receiving surface 38 divided into a plurality of light receiving regions 38a and 38b. Thus, for example, the circuit configuration can be simplified and the monitoring device 201 can be cost-effective and simple.

In the monitoring device 201, the sensor 211(30b) has light emitting means 31b for emitting a light flux to the monitored target 202, an imaging optical system 37b for forming an image of light emission pattern generated on the monitored target 202 by the light emitting means 31b, light receiving means 36 disposed in the vicinity of the position where the imaging optical system 37b forms an image for receiving imaging pattern light from the formed image of the light emission pattern; and a position information output unit 39b for outputting information on the position where an imaging pattern is formed corresponding to the distance to the monitored target 202 based on the position where imaging pattern light is formed into an image on the light receiving means 36.

In the monitoring device constituted as described above, the sensor 211 (30b) has a light emitting means 31b, an imaging optical system 37b and light receiving means 36, and outputs information on the position where an imaging pattern is formed corresponding to the distance to the monitored target 202 based on the position where imaging pattern light is formed into an image on the light receiving means 36. Thus, the monitoring device 201 can be cost-effective and simple.

The monitoring device 201 may have a plurality of the sensors 211. Since the monitoring device 201 constituted as described above has a plurality of sensors 211, it can detect changes of a sleeping person more precisely.

The monitoring device 201 is preferably provided with presence detection means 241 for detecting the monitored target 202 in or in the vicinity of the monitored target area 250. The monitoring device constituted described as above, for example, can save power since the power supply to the monitoring device 201 can be cut off when the presence detecting means cannot detect the presence of the monitored target 202 in or in the vicinity of the monitored target area 250.

Another object of this invention is to provide a monitoring device comprising multiple independent distance sensors 11 installed facing different positions respectively within a monitored target area 50 for measuring the distances to a monitored target 2; a calculating unit 22 for calculating changes over time respectively in the outputs from the distance sensors 11; and a detection processor 23 for selecting a distance sensor 11 which detected the largest change over time within a predetermined period of time in the immediate past and detect movement or changes in shape of the monitored target 2 based on changes over time detected by the selected distance sensor 11; wherein the detection processor 23 selects a distance sensor 11 which detected the largest change over time within a predetermined period of time after the monitored target 2 has been in a quiet state and detects movement or changes in shape of the monitored target 2 based on the changes over time detected by the selected distance sensor 11 when movement of the monitored target 2 has been detected as shown, for example, in FIG. 1 and FIG. 3.

The monitoring device constituted as described above has multiple distance sensors 11, a control part 21, calculating unit 22 and detection processor 23. The multiple distance sensors 11 measure the distances to the monitored target 2 in the monitored target area 50, and changes in each of the outputs from the distance sensors 11 are calculated. Then, a distance sensor 11 which detected the largest change over time within a predetermined period of time in the immediate past is selected and movement or periodic changes in shape of the monitored target 2 are detected based on changes over time detected by the selected distance sensor 11. When the detection processor 23 detects movement of the monitored target 2, a distance sensor which detected the largest change over time in a predetermined period of time after the monitored target 2 has been in a quiet state, and changes in shape of the monitored target can be detected based on changes over time detected by the selected distances sensor 11.

This application is based on the Patent Application No. 2001-181077, filed on Jun. 15, 2001 in Japan, No. 2002-029406, filed on Feb. 6, 2002 in Japan, No. 2002-096209, filed on Mar. 29, 2002 in Japan, the content of which is incorporated herein, as part thereof.

Also, the invention can be fully understood, referring to the following description in details. Further extensive applications of the invention will be apparent from the following description in details. However, it should be noted that the detailed description and specific examples are preferred embodiments of the invention, only for the purpose of the description thereof. Because it is apparent for the person ordinary skilled in the art to modify and change in a variety of manners, within the scope and spirits of the invention.

The applicant does not intend to dedicate any disclosed embodiments to the public, and to the extent any disclosed modifications or alterations may not literally fall within the scope of the claims, they are considered to be part of the invention under the doctrine of the equivalents.

BRIEF DESCRIPTION OF THE DRAWINGS

FIG. 2 is a schematic plan view illustrating an example of arrangement of monitored areas (a) and an example of arrangement of monitoring (b) areas in which the monitored areas overlap in the first embodiment of this invention;

FIG. 8 is a table showing an example of the relation between the area ratio and the distance to an object in the case where an infrared distance sensor using a bipartite PD for use in the first embodiment of this invention is used;

FIG. 14(a) and FIG. 14(b) are a schematic plan view and a schematic front cross-sectional view illustrating the PSD in the case shown in FIG. 13, respectively;

FIG. 18 is a schematic view illustrating illumination patterns in the case shown in FIG. 17;

FIG. 21 is a schematic view illustrating normal and abnormal respiration waveform patterns in the case shown in FIG. 20;

FIG. 22 is a table showing the names of the diseases or diseased sections corresponding to the abnormal respiration waveform patterns shown in FIG. 21;

FIG. 23 is a schematic perspective view illustrating a monitoring device according a second embodiment of this invention;

FIG. 25 is a schematic plan view illustrating an example of arrangement of monitored areas (a) and an example of arrangement of monitored areas (b) in which the monitored areas overlap in the second embodiment of this invention;

BEST MODE FOR CARRYING OUT THE INVENTION

Description will be hereinafter made of embodiments of this invention with reference to the drawings. The same or corresponding components are denoted in all the drawings by the same or similar numerals and overlapping descriptions will be omitted.

Figure 1:
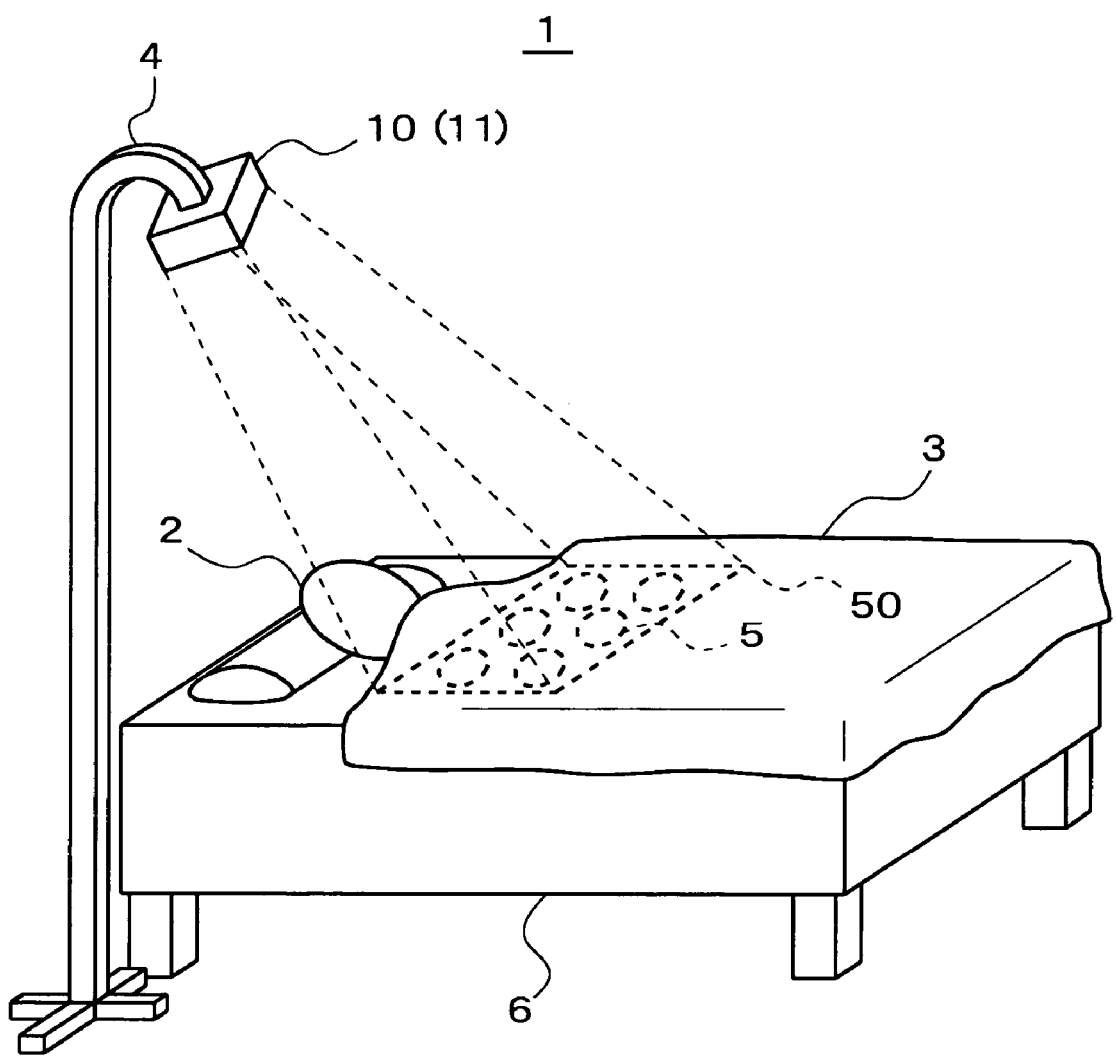
FIG. 1 is a schematic perspective view illustrating the outline of a monitoring device according to a first embodiment of this invention.

FIG. 1 is a schematic perspective view of a monitoring device 1 as a first embodiment of this invention. As shown in the drawing, a sleeping person 2 as a monitored target which shows periodic changes lies on the upper side of a bed 6 as a monitored target area (which will be hereinafter referred to as "monitored area 50"). A bed cloth 3 is laid over the sleeping person 2 and covers part of the sleeping person 2 and part of the bed 6. Namely, The monitoring device 1 monitors the upper surface of the bed cloth 3. The bed cloth 3 may not be used and the monitoring device 1 may monitor the body of the sleeping person 2. In this embodiment, a change in shape is a continuous change, and the continuous change is a concept including periodic and transitional change. Changes in shape of the sleeping person 2 are periodic changes or transitional changes of the sleeping person 2, for example. An example of periodic changes of the sleeping person 2 is respiration of the sleeping person 2. Examples of transitional changes of the sleeping person 2 are motion and movement of the sleeping person 2. Periodic changes are changes with a cycle equivalent to that of respiration of a sleeping person such as a cycle of 5 to 30 times per minute. Namely, the periodic changes in this embodiment do not include periodic changes with a cycle which is considerably different from that of respiration. The respiratory rate of an adult is in a range of 5 to 60 times per minute, and an infant tends to breath at a higher rate.

The monitoring device 1 is configured to determine the condition of the sleeping person 2 based on detected changes in shape of the sleeping person 2. The condition of the sleeping person 2 is, for example, whether it is breathing normally or it is breathing abnormally and thus in a critical condition, whether it is making a motion such as rolling, whether it is making movement such as entering or leaving the bed, and so on.

A casing 10 including a plurality of distance sensors 11 for measuring the distance to the sleeping person 2 in the monitored area 50 is mounted on a stand 4 as shown in the drawing. In the casing 10, the plurality of distance sensors 11 are provided corresponding to a plurality of points to be monitored (which will be hereinafter referred to as "objective points"). The casing 10 (distance sensors 11), which is mounted on the stand 4 in this embodiment, may be installed on a wall or ceiling, if possible. The installation position may be determined depending upon the purpose and the type of the monitoring device. The stand 4 is movable and thus makes placement of the casing 10 easy. The distance sensors 11 are preferably arranged in at least two rows in the casing 10.

Description will be made of the objective points with reference to examples of arrangement of objective points in the schematic plan view of FIG. 2, and with reference to FIG. 1 when necessary. As shown in FIG. 2($a$), a plurality of objective points corresponding to a plurality of distance sensors 11 are arranged in such a manner that they do not overlap with adjacent objective points. In this case, objective points 51, 52, 53, 54, 55 and 56 (which will be hereinafter referred to as "objective points 5" when they are not mentioned separately) are arranged in a grid pattern in the monitored area 50 in such a manner that they do not overlap with each other as shown, for example, in the drawing. The objective points 5 are preferably arranged throughout an area which covers the area in which the chest, abdomen, back and shoulders of the sleeping person 2 on the bed 6 (under the bed cloth 3) can possibly move while it is sleeping. Although the objective points 5 are arranged in a matrix of three rows by two columns (which will be hereinafter represented as "3×2") in this embodiment, the number of the objective points 5 can be determined depending upon conditions such as the place and the sleeping person 2 to be monitored. The objective points 5 may be arranged in, for example, 3×3 or 4×4. In the case where a plurality of the objective points 5 are arranged as described above, even when emission type sensors which measure distance by emitting light or ultrasonic waves are used as the distance sensors 11, distance sensors 11 corresponding to objective points 5 adjacent to each other does not have to be so controlled as not to make emission simultaneously as described later. The monitoring device 1 can therefore be simple in structure.

As shown in an example of arrangement of objective points 5 shown in the schematic plan view of FIG. 2($b$), adjacent objective points 5 may overlap with each other. In this case, since blind areas in the monitored area 50 can be reduced, monitoring can be performed with higher precision. When emission type sensors which measure distance by emitting light or ultrasonic waves are used as the distance sensors 11, the distance sensors 11 corresponding to the objective points 5 overlapping with each other must be so controlled as not to make emission simultaneously so that they cannot be influenced by each other. This is because when a plurality of distance sensors 11 emit light, for example, simultaneously, light emitted from other distance sensors 11 is mixed with the light which must be received and makes it difficult to measure the distance to the corresponding objective points 5.

In the case where hereinafter described infrared distance sensors 30$a$ (see FIG. 5) are used as the distance sensors 11, when the infrared distance sensors 30$a$ emit light fluxes with different wavelengths and hereinafter described light receiving lenses 37a are configured to transmit light in a wavelength band corresponding to that of the emitted beam light as described later by means of coating, for example, the distance sensors 30a do not have to be so controlled as not to make emissions simultaneously even when adjacent objective points 5 overlap with each other. Also, when the light sources of the emitted light flux are blinked at prescribed frequencies, which are different from each other among the distance sensors 30a and hereinafter described electric band pass filters for extracting signals with the frequencies are provided with the distance sensor 11, the distance sensors 30a do not have to be so controlled as not to make emissions simultaneously even when adjacent objective points 5 overlap with each other.

Here, the operation control in the case where emission type sensors are used as the distance sensors 11 and the objective points 5 corresponding to a plurality of the distance sensors 11 are overlapped with each other as shown in FIG. 2(b) will be described. The control is performed by a control part 21 of a hereinafter described control unit 20. When emission type distance sensors are used, each of the distance sensors 11 is controlled to measure the distance after another has finished measurement. Namely, the plurality of distance sensors 11 are so controlled as not to measure the distance simultaneously. Such operation is repeated until all the distance sensors 11 finish measuring the distance. This series of operations is defined as one cycle, and the time for one cycle is defined as T.

When the distance sensors 11 are not so controlled as to measure the distance one after another but so controlled as not to measure the distances to adjacent objective points 5 simultaneously (for example, the distance sensors 11 are controlled to measure the distances to every other objective points 5 simultaneously), it is possible to allow a plurality of distance sensors 11 to measure the distance simultaneously. The time T for one cycle can thereby be considerably reduced.

Figure 3:
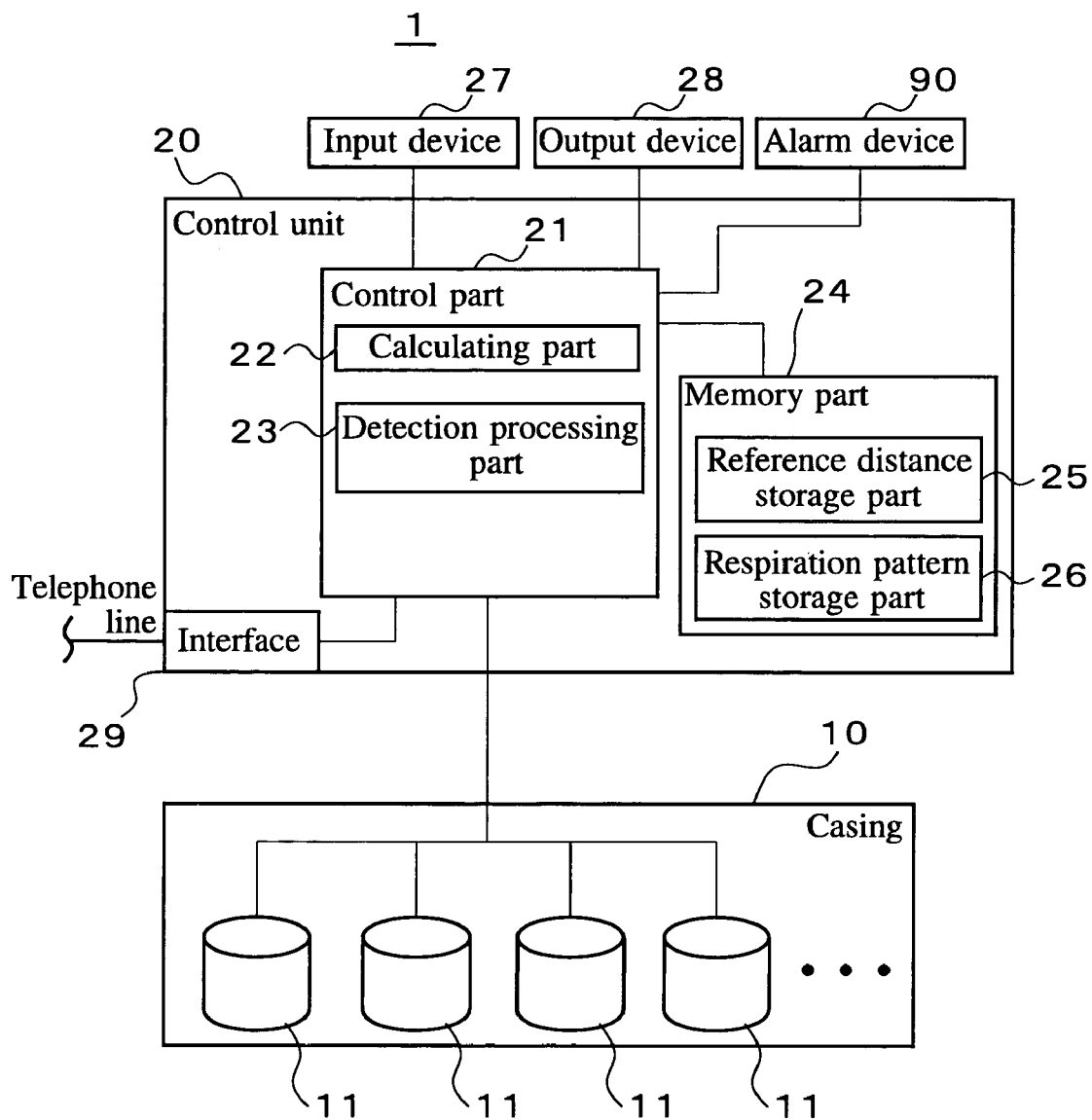
FIG. 3 is a block diagram illustrating a configuration example of the monitoring device for use in the first embodiment of this invention.

Description will be made of an example of the configuration of the monitoring device 1 with reference to FIG. 3. The monitoring device 1 comprises a casing 10 in which a plurality of distance sensors are installed and a control unit 20. The control unit 20 is typically a personal computer or a microcomputer. The plurality of distance sensors 11 are connected to the control unit 20 and configured to output distance information as outputs there from to the control unit 20. The distance information herein is an output value from each distance sensor 11 before calculation of the real distance but may be the distance to the object (sleeping person 2). This will be hereinafter referred to simply as "distance". Description will be hereinafter made using the term "distance". The distance is preferably obtained from each distance sensor 11 in time series. The distance sensors 11 and the control unit 20, which are shown as being separate in the drawing, may be integrated together.

The distance sensors 11 in this embodiment are arranged in 3×2 in the casing 10 corresponding to monitored areas 6 arranged in 3×2 as described with FIG. 2.

Figure 4:
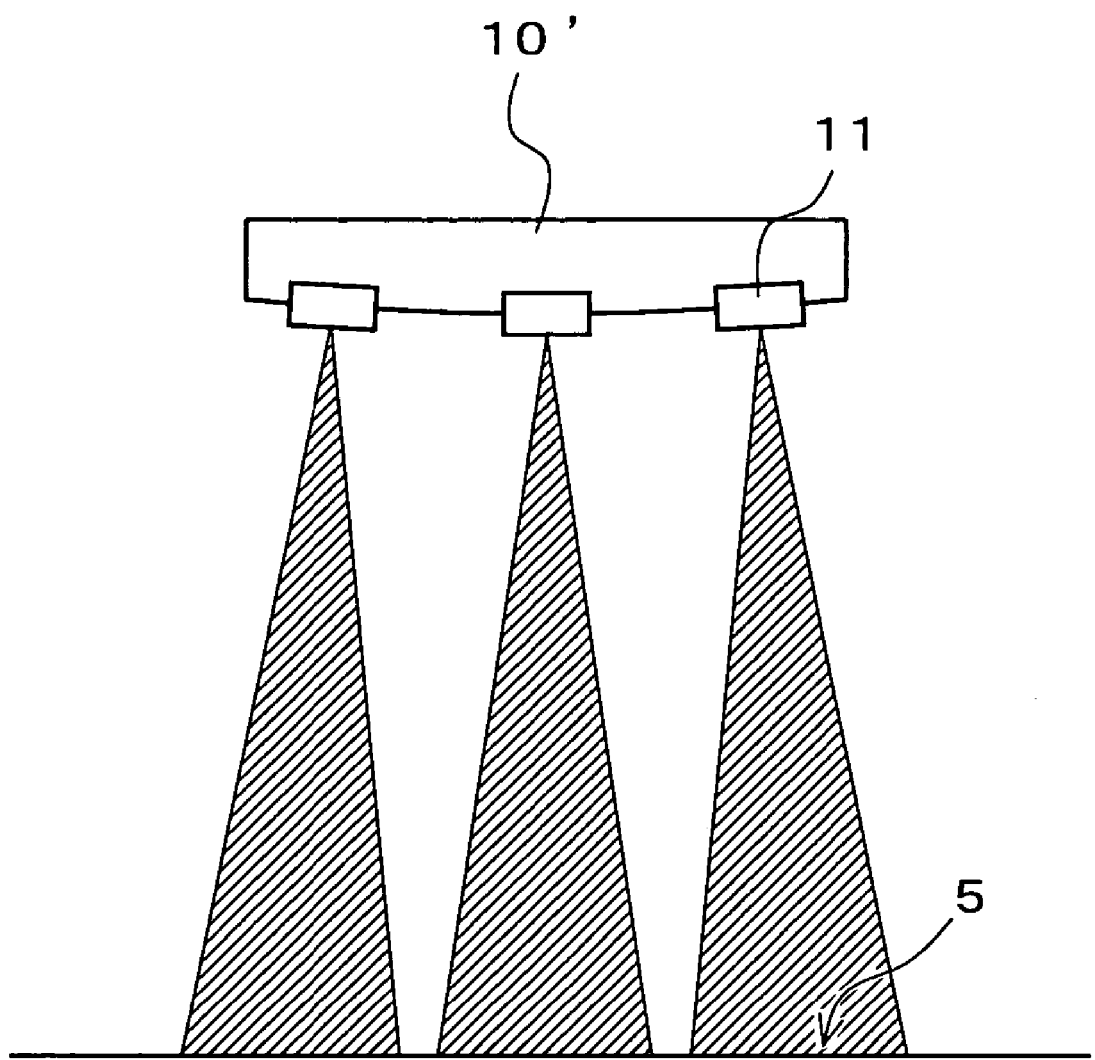
FIG. 4 is a schematic side view illustrating the case in which distance sensors are arranged along a curve in the first embodiment.

Though The distance sensors 11 are typically aligned in the casing 10, the casing 10 may be curved as is a casing 10' shown in the schematic view of FIG. 4. In this case, the distance sensors 11 are arranged along the curve. When the casing 10' is used, the wide monitored area 50 can be easily obtained even when the casing 10' is small. The casing 10' enables the distance sensors 11 to be arranged in such a manner that adjacent objective points 5 do not overlap with each other with ease even when the casing 10' is small. Thus, the device can be small in size.

Description will be made of the distance sensors 11 further in detail. As the distance sensors 11, infrared emitting distance sensors, ultrasonic wave sensors, electromagnetic pulse distance sensors, passive optical distance sensors or the like can be used. Among them, infrared emitting distance sensors, ultrasonic wave sensors, and electromagnetic pulse distance sensors are emission type sensors. As the distance sensors 11, relatively simple and inexpensive sensors such as sensors used in auto-focus cameras are preferably used. By using such distance sensors 11, the monitoring device 1 can be simple and cost-effective. Description will be made of an infrared distance sensor, an ultrasonic wave sensor, an electromagnetic pulse distance sensor, and a passive optical distance sensor as examples of the distance sensor 11 with reference to drawings.

Figure 5:
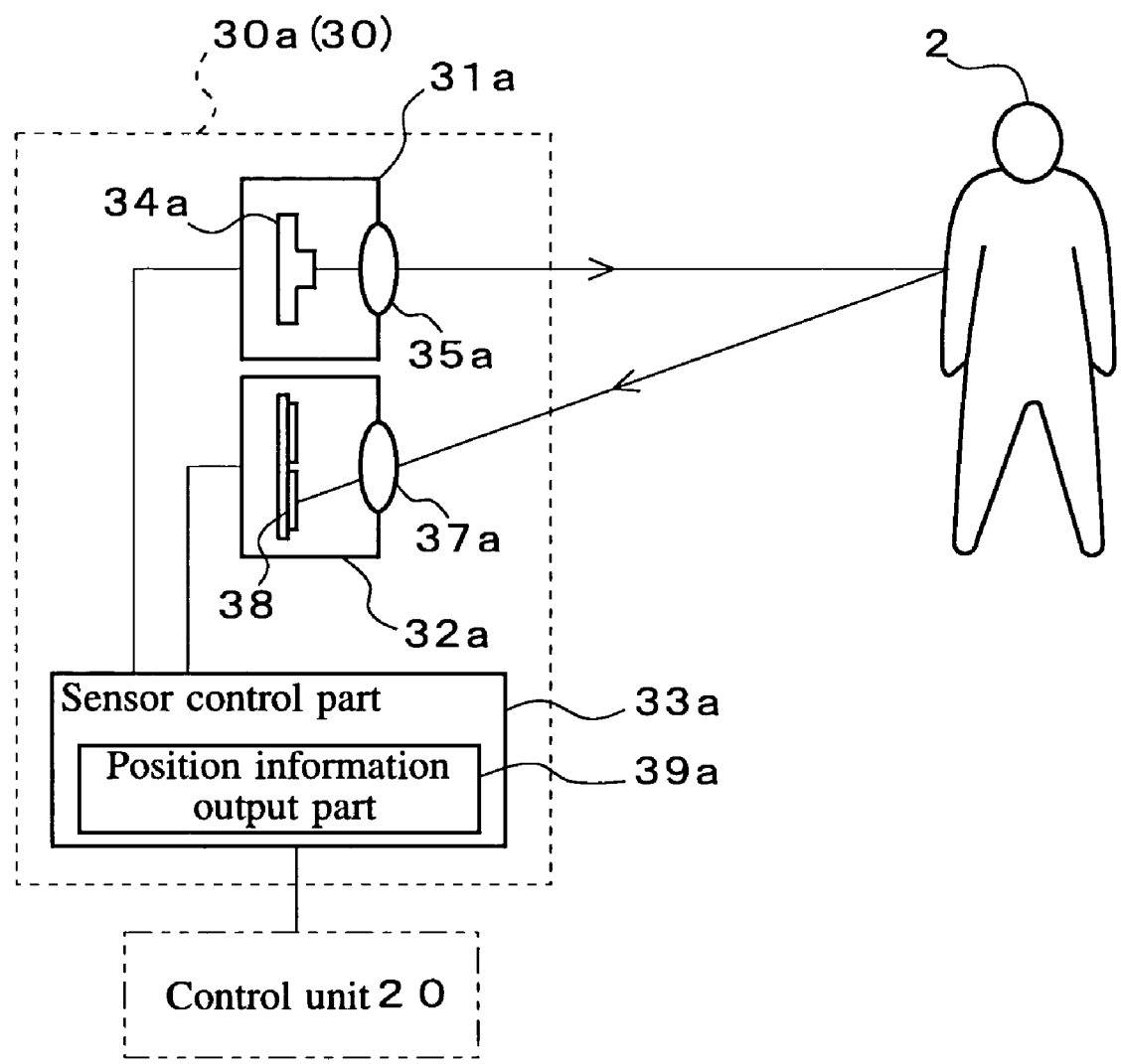
FIG. 5 is a block diagram illustrating a configuration example of an infrared distance sensor using a bipartite PD for use in the first embodiment of this invention.

Referring to FIG. 5, an infrared emitting distance sensor will be described. Here, description will be made of an infrared emitting distance sensor 30 (which will be hereinafter referred to as "infrared distance sensor 30") as an example of the distance sensor 11. The infrared distance sensor 30 is an active optical sensor, as it is called. As the infrared distance sensor 30, a sensor using a photo detector divided into a plurality of light receiving regions (which will be hereinafter referred to as "multipartite PD") or a sensor using a position detection element (which will be hereinafter referred to as "PSD") can be used. A sensor using a multipartite PD is hereinafter referred to as "infrared distance sensor 30a" and a sensor using a PSD is hereinafter referred to as "infrared distance sensor 30b". When they are not separated, the term "infrared distance sensor 30" will be used.

As shown in the block diagram of FIG. 5, the infrared distance sensor 30a using a multipartite PD comprises an infrared light emitting part 31a as light emitting means for emitting a light flux to the sleeping person 2, an infrared light receiving part 32a, and a sensor control part 33a for controlling the entire infrared distance sensor 30a. The sensor control part 33a may be incorporated in the control part 21 of the control unit 20 (see FIG. 3).

The infrared light emitting part 31a has an infrared LED 34a and an emission lens 35a. An infrared light flux emitted from the infrared LED 34a (which will be hereinafter referred to as "beam" as necessary) is emitted to the sleeping person 2 via the emission lens 35a as a narrow collimated light flux. A collimated light flux herein need to be substantially collimated and includes an approximately collimated light flux. The infrared light receiving part 32a has a light receiving lens 37a as an imaging optical system for forming an image of a light emission pattern generated on the sleeping person 2 by the infrared light emitting part 31a, and a multipartite PD 38 as a light receiving surface disposed in the vicinity of the position where the light receiving lens 37a forms an image and divided into a plurality of light receiving regions for receiving imaging pattern light from the formed image of the light emission pattern. Here, the multipartite PD 38 is divided into two light receiving regions (which will be hereinafter referred to as "bipartite PD 38").

The infrared distance sensor 30a also has a position information output part 39a as a position information output unit configured to receive signals from each of the light receiving regions, compare the intensities of imaging pattern lights incident on each of the light receiving regions based on the signals each other, and output information on the position where an imaging pattern is formed corresponding to the distance to the sleeping person 2. The position information output part 39a is incorporated in the sensor control part 33a. Here, the light flux is beam light, for example, and the light emission pattern made by the light flux is a beam light spot.

And the imaging pattern light is light incident on the bipartite PD 38 of reflected light from the sleeping person 2. The reflected light is from a beam light spot formed on the sleeping person 2. The imaging pattern is an image of the beam light spot on the sleeping person 2 formed by the light receiving lens 37a. Namely, the imaging pattern here is a generally circular image.

Figure 6:
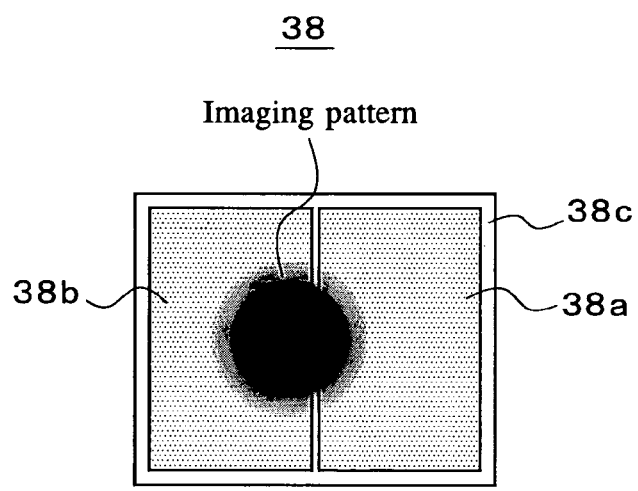
FIG. 6 is a schematic view illustrating the case in which two PDs are used in the case shown in FIG. 5.
Figure 7:
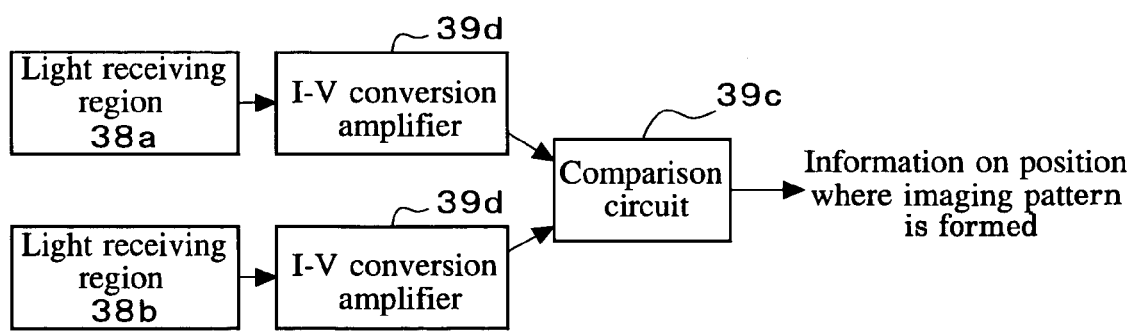
FIG. 7 is a conceptual diagram illustrating the case in which two PDs are used in the case shown in FIG. 6.

Referring now to FIG. 6 and FIG. 7, the bipartite PD 38 will be described. As shown in FIG. 6, the bipartite PD 38 is divided into two light receiving regions 38a and 38b arranged on a substrate 38c side by side. The dividing direction is generally normal to a direction in which the imaging pattern moves with change in the distance (the lateral direction in the drawing). In other words, the bipartite PD 38 is divided such that the divided light receiving regions 38a and 38b align in the direction in which the imaging pattern moves with change in the distance.

When imaging pattern light reflected on the sleeping person 2 is formed into an image across the light receiving regions 38a and 38b by the light receiving lens 37a, currents are generated in each of the light receiving regions.

As shown in FIG. 7, an individual I-V conversion amplifier 39d is connected to each of the light receiving regions 38a and 38b. The current values generated respectively in the light receiving regions 38a and 38b are converted into voltage values by the I-V conversion amplifier 39d and input into a comparison circuit 39c. The comparison circuit 39c obtains the ratio of the voltage values to calculate information on the position where an imaging pattern is formed into an image, namely the distance. The I-V conversion amplifiers 39d and the comparison circuit 39c are both incorporated in the position information output part 39a. In the case of the bipartite PD 38, the light receiving area of the bipartite PD 38 is preferably larger than the diameter of the imaging pattern (pattern diameter) having a generally circular shape so that even when the distance to the object varies and the pattern diameter is increased, the imaging pattern can not move off the bipartite PD 38 and the distance can be measured with stability and precision.

Here, the bipartite PD 38 generates current proportional to the light quantity (intensity) of the imaging pattern light. Thus, the voltage values converted by the I-V conversion amplifiers 39d from the currents output from the light receiving regions 38a and 38b can be regarded as the areas of the imaging patterns formed on the light receiving regions 38a and 38b, respectively. Namely, the ratio of the voltage values can be regarded as the ratio of the areas of the imaging patterns formed on the light receiving regions 38a and 38b. The area ratio varies when the distance to the object is changed and the imaging pattern is moved. Namely, the area ratio can be regarded as a position equivalent value of the imaging pattern. Thus, the area ratio, namely the ratio of the voltage values, can be used as information on the position where an imaging pattern is formed, namely the distance.

Figure 9:
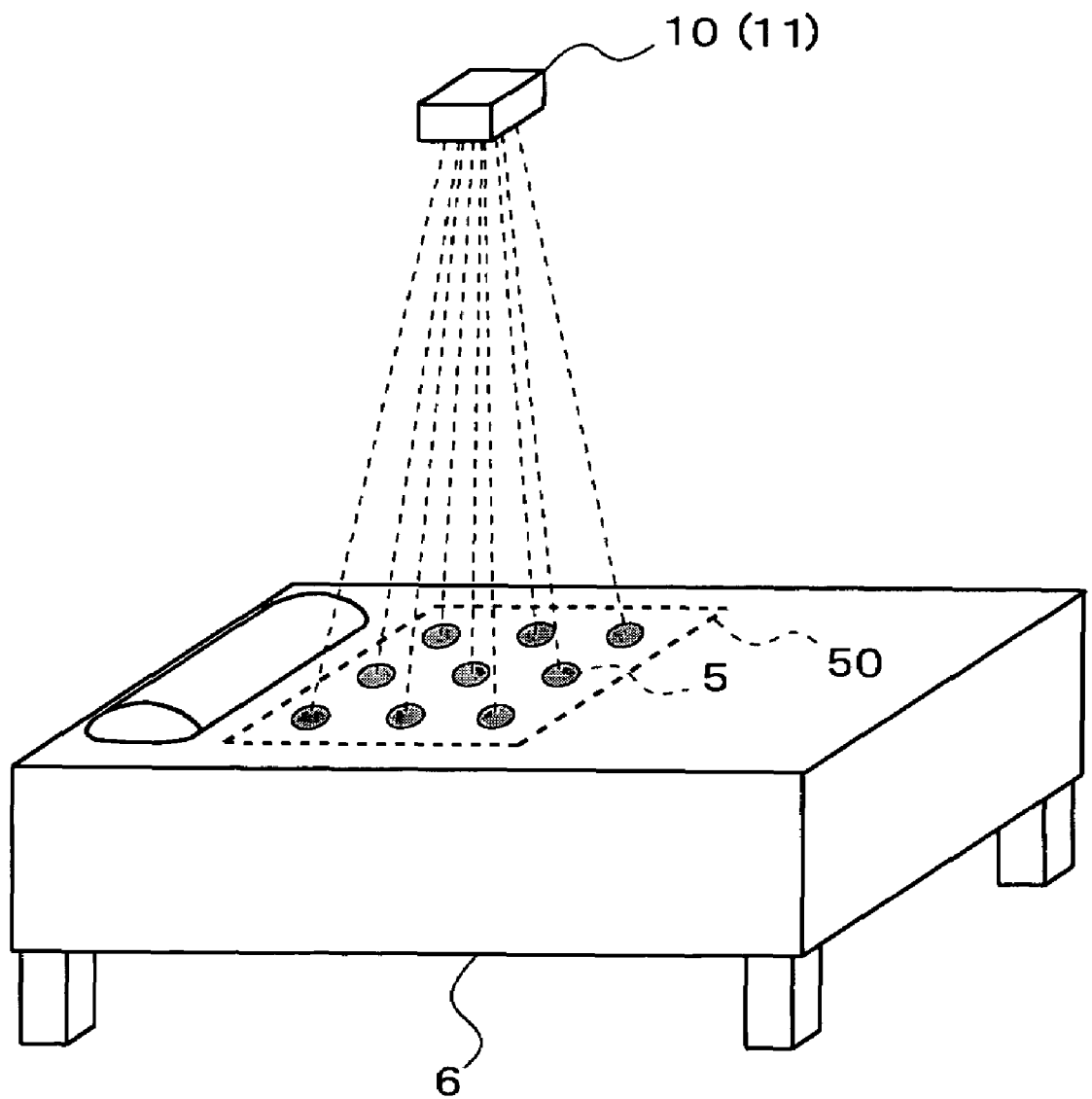
FIG. 9 is a schematic perspective view illustrating the case in which infrared distance sensors are installed with their optical axes generally perpendicular to the monitored target area in the case shown in FIG. 8.

FIG. 8 shows an example of the relation between the area ratio and the distance to the object. Here, the infrared distance sensors 30a are installed with their optical axes generally normal to the monitored area 50 (see FIG. 1) as shown in FIG. 9. Although the objective points 5 are arranged in 3×3 in the drawing, the number of the objective points may be determined appropriately as described with FIG. 2. The imaging pattern on the light receiving region 38a is defined as region A, and the imaging pattern on the light receiving region 38b is defined as region B. The baseline length is the distance between the optical axes of the emission lens 35a and the light receiving lens 37a, the beam light diameter is the diameter of the beam light emitted from the emission lens 35a, the sensor installation height is the distance from the light receiving lens 37a to the monitored area 50 (the upper surface of the bed 6), the focal length is the focal length of the light receiving lens 37a, and the image distance is the distance from the light receiving lens 37a to the imaging surface of the bipartite PD 38. The bipartite PD 38 has two 4 mm×4 mm light receiving regions.

Although the multipartite PD 38 is divided into two light receiving regions in the above description, the multipartite PD 38 may be divided into more than two light receiving regions or constituted of non-divided PDs arranged side by side.

Figure 10:
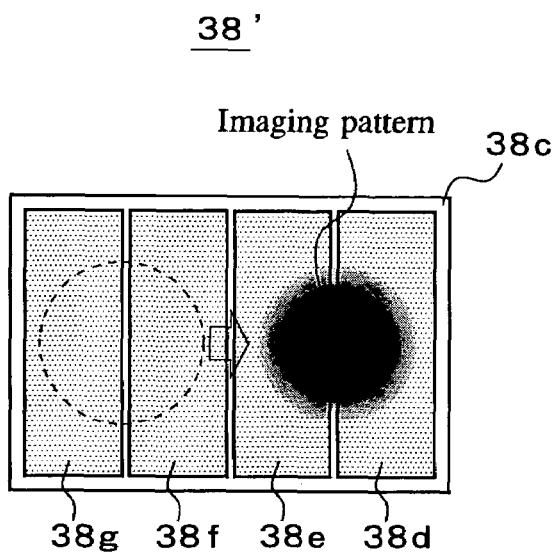
FIG. 10 is a schematic view illustrating a quadripartite PD for use in the first embodiment of this invention.
Figure 11:
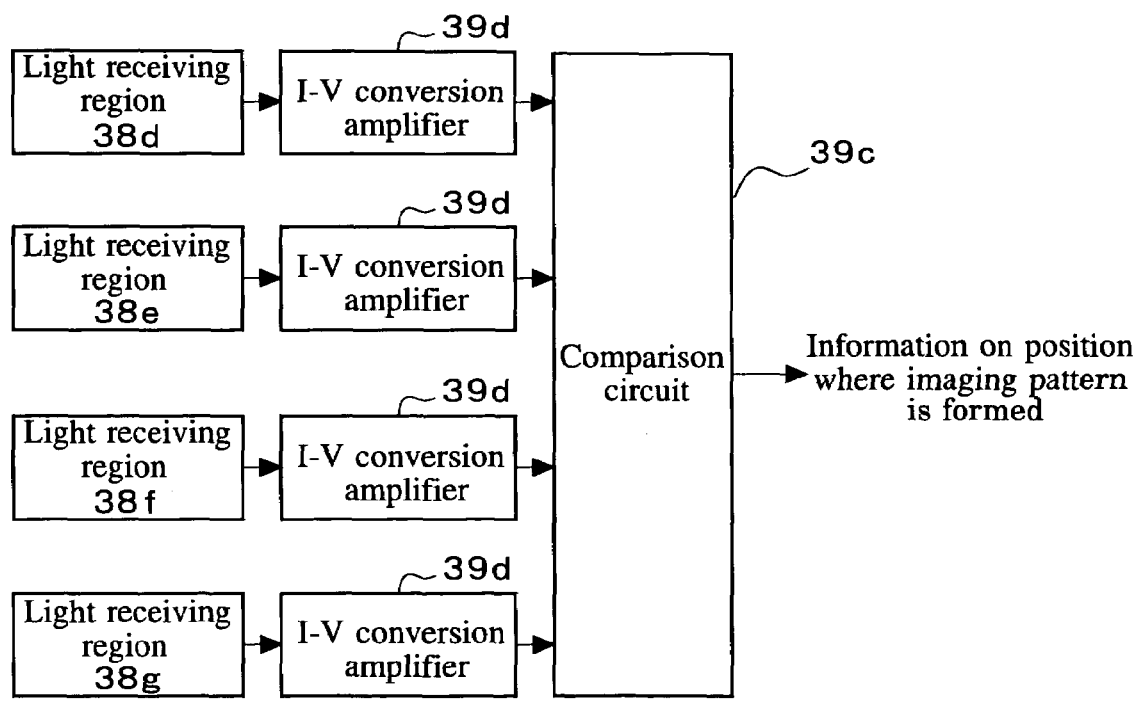
FIG. 11 is a conceptual diagram illustrating the quadripartite PD in the case shown in FIG. 10.

Here, the multipartite PD 38 is divided into four light receiving regions as shown in FIG. 10 and FIG. 11 (which will be hereinafter referred to as quadripartite PD 38'). As in the case with the bipartite PD 38, the quadripartite PD 38' is divided into four light receiving regions 38d, 38e, 38f, and 38g arranged side by side on a substrate 38c as shown in FIG. 10. When imaging pattern light reflected on the sleeping person 2 is formed into an image on the quadripartite PD 38' by the light receiving lens 37a, currents are generated in each of the light receiving regions.

As shown in FIG. 11, an individual I-V conversion amplifier 39d is connected to each of the light receiving regions 38d, 38e, 38f, and 38g. The current values generated respectively in the light receiving regions are converted into voltage values by the I-V conversion amplifiers 39d and input into a comparison circuit 39c. The comparison circuit 39c compares the voltage values to calculate information on the position where an imaging pattern is formed, namely the distance. The comparison circuit 39c preferably obtains the ratio of the two largest values among the outputs from the light receiving regions 38d, 38e, 38f, and 38g in calculating the information on the position where an imaging pattern is formed.

The number of division of the light receiving surface 38 is preferably 10 or less, more preferably 4 or less, most preferably 2. By limiting the number of division, the number of auxiliary devices such as the I-V conversion amplifiers 39d is limited and the structure can be simplified.

In the case where a multipartite PD 38 divided into three or more light receiving regions as shown in FIG. 10 is used, even when the imaging pattern is largely moved and deviated from two of the light receiving regions, namely even when the distance to the measuring object is largely varied, the information on the position where an imaging pattern is formed can be calculated with the other two light receiving regions.

Also, when a multipartite PD 38 divided into three or more light receiving regions is used, the width of one light receiving region in the direction in which the imaging pattern moves with changes in the distance (lateral direction in the drawing) is preferably smaller than the pattern diameter. This is to prevent a situation where the imaging pattern does not extend across at least two light receiving regions but falls within one light receiving region and the ratio of voltage values does not vary even when the imaging pattern moves. Namely, occurrence of a situation where the ratio of voltage values does not vary even when the imaging pattern moves can be prevented and the distance can be measured with stability and precision. A telemetric optical system may be used as the light receiving lens 37a. In this case, since the pattern diameter is constant even when the distance to the object is varied, the voltage ratio is varied only by the movement of the imaging pattern and the calculation can be simplified. A telemetric optical system is a telescope optical system in which an aperture is located at one of the focal points of the objective lens. When the bipartite PD 38 is used, a telemetric optical system may also be used as the light receiving lens 37a.

Description will be made of the case where the bipartite PD 38 is used.

Referring again to FIG. 5, the infrared distance sensor 30a will be described in further detail. The light receiving lens 37a is coated with a coating which transmits only light in the wavelength band of the emitted beam light. Thus, the infrared distance sensor 30a can perform position detection without being significantly affected by disturbing lights. Although the light flux is a narrow collimated light flux in the above description, the light flux need to be substantially collimated and may be diffused or converged to some extent, to such an extent that the size of the imaging pattern on the bipartite PD 38 is appropriate and does not influence the detection of information on the position where an imaging pattern is formed.

The infrared light emitting parts 31a of the infrared distance sensors 30a may be made to emit beam light with different wavelengths. In this case, the light receiving lenses 37a are coated with a coating which transmits beam light in a wavelength band corresponding to that of the emitted beam light. The beam lights are not thereby influenced by adjacent beam lights even when adjacent beam lights overlap with each other as described with FIG. 2(b), and the infrared distance sensors 30a does not have to be so controlled as not to make emission simultaneously. Thus, the monitoring device can be simplified. The infrared LED 34a (light sources) of the infrared distance sensor 30a may be blinked at a frequency and the infrared light receiving part 32a may be provided with an electric band pass filter which extracts only signals of the frequency. The influences of disturbing lights can thereby be reduced. When the modulation frequency is changed for each sensor, the beam lights are not influenced by adjacent beam lights even when adjacent beam lights overlap with each other as described with FIG. 2(b). Thus, the infrared distance sensors 30a do not have to be so controlled as not to make emission simultaneously even when adjacent beam lights overlap with each other, and the monitoring device can be simplified. Synchronous detection by which polarities of the amplifier of the infrared light receiving part 32a are switched in synchronization with the timing of emission of the infrared LED 34a may be preferably performed.

The infrared distance sensor 30a uses infrared ray as the beam emitted, which is invisible to human eyes and thus does not give an uncomfortable feeling. The infrared distance sensor 30a may be one in which the PSD of a hereinafter described infrared distance sensor 30b using a PSD is changed to a bipartite PD 38.

As has been described previously, the infrared distance sensor 30a using the bipartite PD 38 can simplify the circuit configuration. Thus, a cost-effective and simple monitoring device can be achieved. Especially, when the number of division is two, the circuit configuration can be significantly simplified. Thus, a cost-effective and simple monitoring device can be achieved.

The sensor control part 33a of the infrared distance sensor 30a performs modulation in detecting information on the position where an imaging pattern is formed to distinguish the imaging pattern from disturbing lights. The modulation, for example, is an operation that interrupts the emission of the beam light periodically and repeatedly. In this case, the interruption, for example, may be by turning off the light source or by rotating a shielding plate or a slit. Also, the intensity of the beam light may be varied through the modulation depending on the intensity of disturbing lights. And the sensor control part 33a subtracts the output value of the bipartite PD 38 at the time when it is not emitting the beam light from the output value of the bipartite PD 38 at the time when it is emitting the beam light to obtain an output value. The sensor control part 33a performs such an operation a plurality of times and adopts the average of the output values as the information on the position where an imaging pattern is formed (which will be hereinafter referred to as "distance measuring signal") to improve reliability. The sensor control part 33a outputs a distance measuring signal value x which is the value of the distance measuring signal as the distance to the control unit 20.

Figure 12:
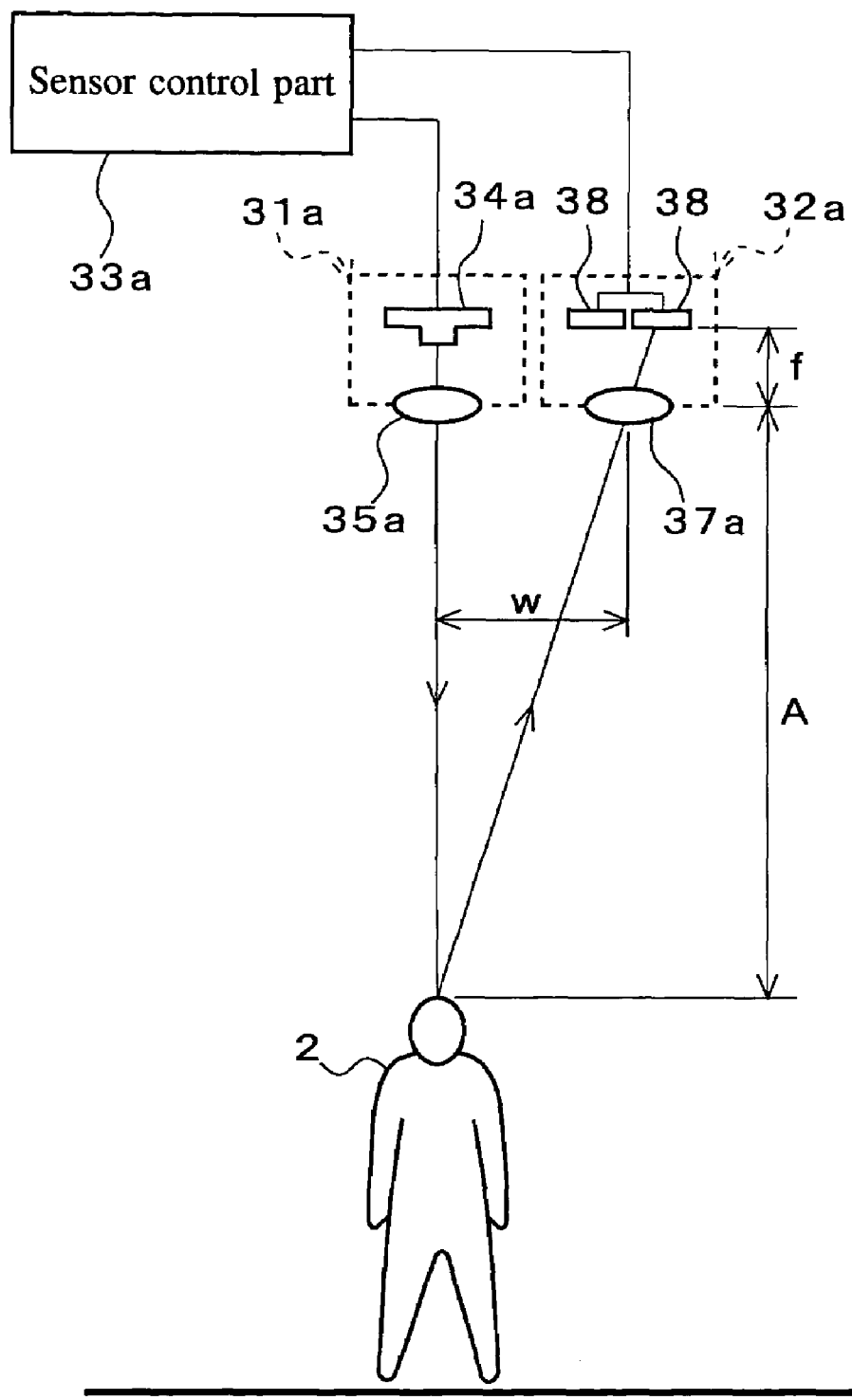
FIG. 12 is a schematic diagram illustrating the method for calculating the distance to a monitored target using the infrared distance sensor for use in the first embodiment of this invention.

As shown in the schematic view of FIG. 12, the distance value A to the sleeping person 2 as the object can be calculated by the following equation using trigonometry based on the distance measuring signal x:

$$A = f \times w/(x-b) \tag{1}$$

wherein f is the focal distance of the light receiving lens 37a of the infrared light receiving part 32a in the case where the light receiving lens 37a is a single lens, w is the distance between the infrared LED 34a and the bipartite PD 38, in other words, the distance between the optical axes of the emission lens 35a and the light receiving lens 37a (baseline length), and b is a bias value which depends on the arrangement of the light receiving element of the PD 38. When a combination lens used in general is used, the focal distance is the focal distance of the combination lens. The distance value A is preferably calculated by the control part 21 of the control unit 20.

The infrared distance sensor 30a, which outputs the distance measuring signal x as the distance in the above description, may output the distance value A calculated by the above method.

Figure 13:
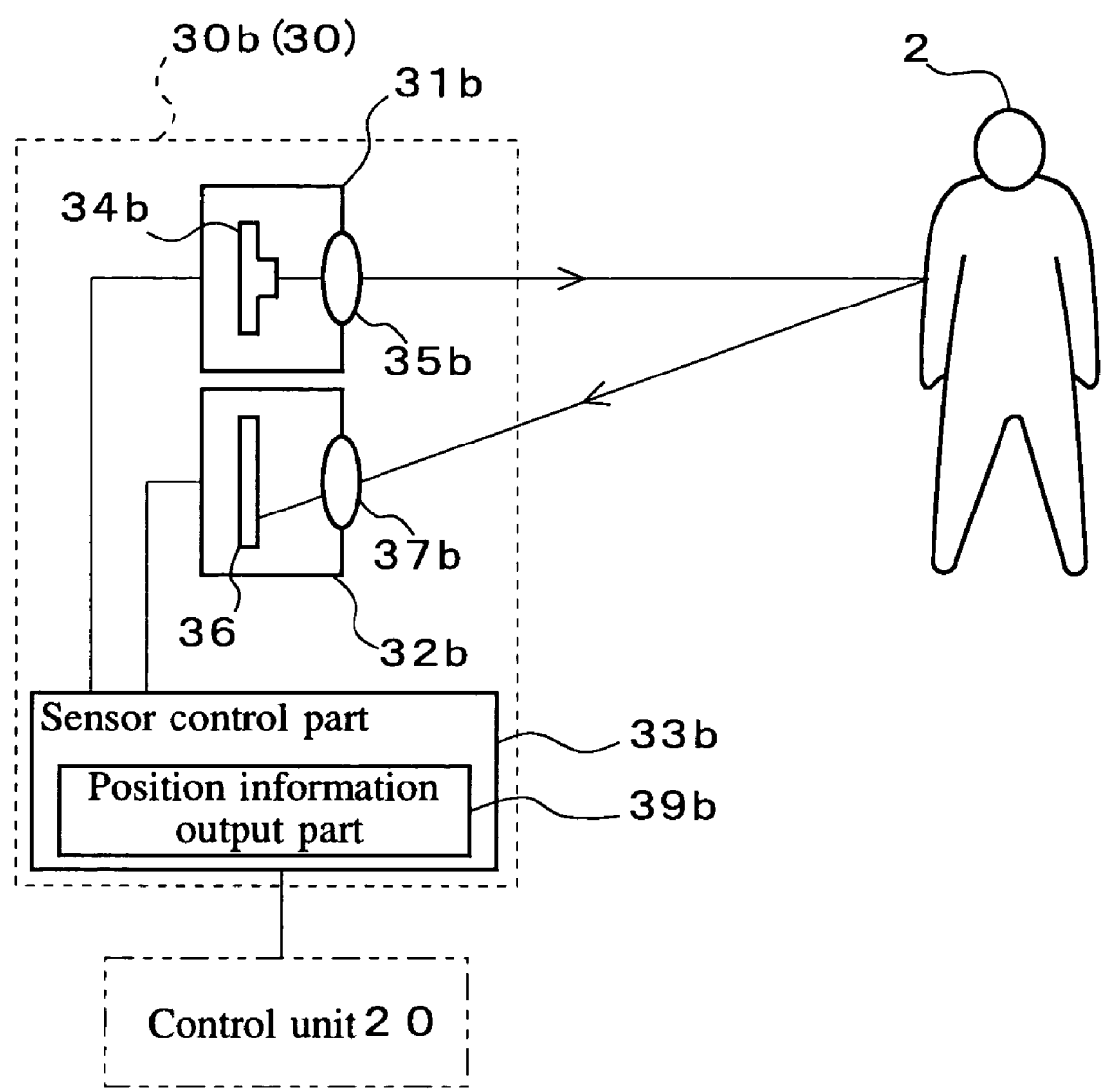
FIG. 13 is a block diagram illustrating a configuration example of an infrared distance sensor using a PSD for use in the first embodiment of this invention.

Description will be made of the infrared distance sensor 30b using a PSD with reference to the block diagram of FIG. 13. The infrared distance sensor 30b comprises an infrared light emitting part 31b as light emitting means for emitting a light flux to the sleeping person 2, an infrared light receiving part 32b, and a sensor control part 33b for controlling the entire infrared distance sensor 30b. The sensor control part 33b may be incorporated in the control part 21 of the control unit 20 (see FIG. 3).

The infrared light emitting part 31b has an infrared LED 34b and an emission lens 35b. An infrared light flux emitted from the infrared LED 34b is emitted to the sleeping person 2 via the emission lens 35b as a narrow beam of a collimated light flux. The infrared light receiving part 32b has a light receiving lens 37b as an imaging optical system for forming an image of a light emission pattern generated on the sleeping person 2 by the infrared light emitting part 31b, and a one-dimensional PSD 36 as light receiving means disposed in the vicinity of the position where the light receiving lens 37b forms an image for receiving imaging pattern light from the formed image of the light emission pattern. The infrared distance sensor 30b also has a position information output part 39b as a position information output unit configured to output information on the position where an imaging pattern is formed corresponding to the distance to the sleeping person 2 based on the position where imaging pattern light is formed into an image on the PSD 36. The position information output part 39b is incorporated in the sensor control part 33b. Here, the light flux is beam light as in the case with the infrared light emitting part 31a and the light emission pattern made by the light flux is a beam light spot. Herein below, the embodiment is described where the imaging pattern is an image of the beam light spot.

The light receiving lens 37b is coated with a coating which transmits light in a wavelength band of the emitted light.

Thus, the infrared distance sensor 30b can perform position detection without being significantly affected by disturbing lights. Although the light flux is a narrow collimated light flux in the above description, the light flux need to be substantially collimated and may be diffused or converged to some extent, to such an extent that the size of the imaging pattern on the PSD 36, which will be described later, is appropriate and does not influence the detection of the location of the center of gravity.

Description will be made of the PSD 36 in further detail with reference to FIG. 14. FIG. 14(a) is a schematic plan view of the PSD 36 and FIG. 14(b) is a schematic cross-sectional front view of the PSD 36. As shown in FIG. 14(a), the PSD 36 has a light receiving area which is larger than the imaging pattern, and has such a length in the direction which the imaging pattern moves with changes in the distance (the lateral direction in the drawing) that the image forming pattern does not move off the light receiving area when the image forming pattern moves within a necessary distance measuring range.

As shown in FIG. 14(b), the PSD 36 comprises a P layer 36a provided on the image pattern light receiving side of a silicon plate, an N layer provided on the side opposite the P layer, and an I layer 36c interposed between the P layer 36a and the N layer 36b. The imaging pattern formed on the PSD 36 is converted into photo electricity and separately output from electrodes 36d attached on both sides of the P layer 36a.

The infrared distance sensor 30b has the position information output part 39b which performs an operation of the output signals of the photo electricity output from the both sides of the PSD 36 and outputs the location of the center of gravity of the imaging pattern as information on the position where an imaging pattern is formed, and thus can measure the distance to the sleeping person 2 as described later. The beam light emitted from the infrared distance sensor 30b is invisible to human eyes since it is infrared light and thus does not give uncomfortable feeling.

The sensor control part 33b of the infrared distance sensor 30b performs modulation when the PSD 36 detects the location of the center of gravity of the imaging pattern to distinguish it from disturbing lights. The modulation is an operation similar to the modulation described in the description of the infrared distance sensor 30a. The sensor control part 33b performs the modulation operation a plurality of times and adopts the average of the output values as a gravity center complementary signal (which will be hereinafter referred to as "distance measuring signal"), which is the information on the position where an imaging pattern is formed, to improve reliability. The sensor control part 33 outputs a distance measuring signal value x, which is the value of the distance measuring signal, as the distance to the control unit 20. The distance value A to the sleeping person 2 as the object can be calculated by the same method as described with FIG. 12 using trigonometry based on the distance measuring signal x. As in the case with the infrared sensor 30a, the infrared distance sensor 30b, which outputs the distance measuring signal x as the distance in the above description, may output the distance value A calculated by the above method.

Since the infrared distance sensor 30b can be constituted in a simple manner by using the PSD 36, a cost-effective and simple monitoring device can be achieved.

Although the distance measuring signal x output from each of the infrared distance sensors 30 is modulated as described above, influences of disturbing lights still remain slightly in the distance measuring signal x and the signal is fluctuating. To absorb the fluctuation, the average of the distance measuring signals x obtained in time series is calculated and adopted as data at the moment. The data may be the average value of the distance values A calculated from the distance measuring signal values x or may be a height H2, which is the average value of hereinafter described heights H1 calculated from the distance values A or a length L2, which is the average value of hereinafter described lengths L1 calculated from the distance values A. There are several methods for obtaining the average value. The average value may be the average of data obtained in a predetermined period of time or the moving average value calculated in time series from a predetermined number of data. The former method needs only a small number of data and thus is suitable to grasp the condition roughly. The latter method needs a large number of data but is suitable to keep track of minute movement.

Figure 15:
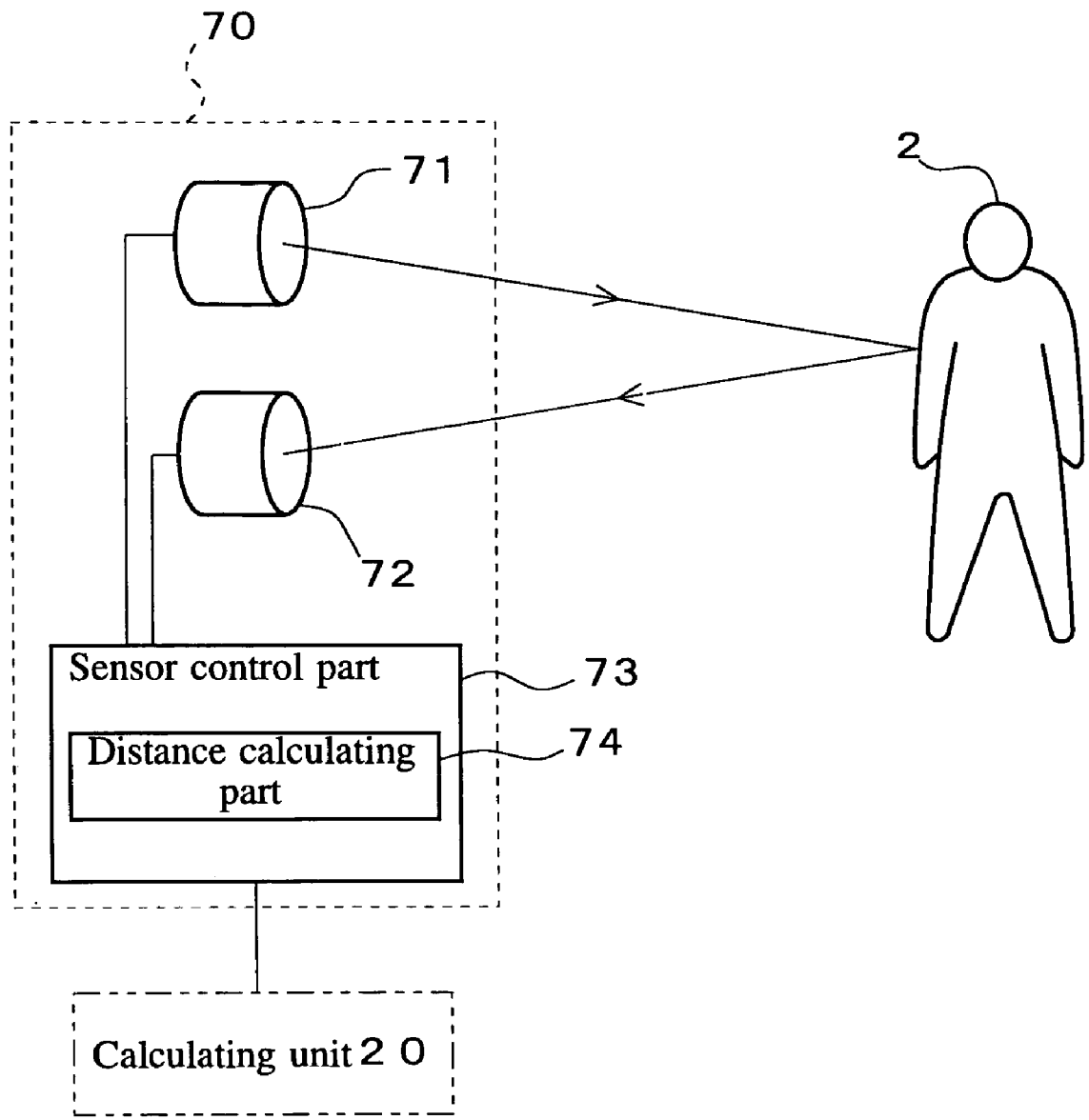
FIG. 15 is a block diagram illustrating a configuration example of an ultrasonic wave sensor for use in the first embodiment of this invention.

Description will be made of an ultrasonic wave sensor 70 in the embodiment of this invention with reference to the block diagram of FIG. 15. The ultrasonic wave sensor 70 comprises an ultrasonic wave transmitting part 71 as an ultrasonic wave generator, an ultrasonic wave receiving part 72 as an ultrasonic wave receiver, and a sensor control part 73. The sensor control part 73 has a distance calculating part 74 for calculating the distance to the sleeping person 2 from the time difference between the transmission from the ultrasonic wave transmitting part 71 and the reception by the ultrasonic wave receiving part 72. The sensor control part 73 may be incorporated in the control part 21 of the control unit 20. The ultrasonic wave transmitting part 71 and the ultrasonic wave receiving part 72, which are separate in this embodiment, may be integrated together. The distance to the sleeping person 2 calculated by the distance calculating part 74 may be the time difference. This is because the distance to the sleeping person 2 can be linearly obtained from the time difference and the changes in the time difference can be regarded as changes in the distance.

The ultrasonic wave transmitting part 71 has means for generating ultrasonic waves comprising a material which exhibits a piezoelectric effect such as piezoelectric ceramic held by a metal plate or the like (vibrator). When signal voltage is applied to the vibrator, the vibrator flexural vibrated and generates ultrasonic waves. The ultrasonic wave receiving part 72 has a vibrator as receiving means, which is vibrated by, reflected ultrasonic waves and outputs electricity. When the ultrasonic wave sensor can detect the time difference between the transmission and the reception by intermittently generating ultrasonic waves and detecting reflected signal waves, the distance to the sleeping person 2 can be obtained since the sound speed is known. In this case, it is possible to detect the closest reflection or measure an average distance to the emission region, although it depends on the way of processing the signals after the detection.

Figure 16:
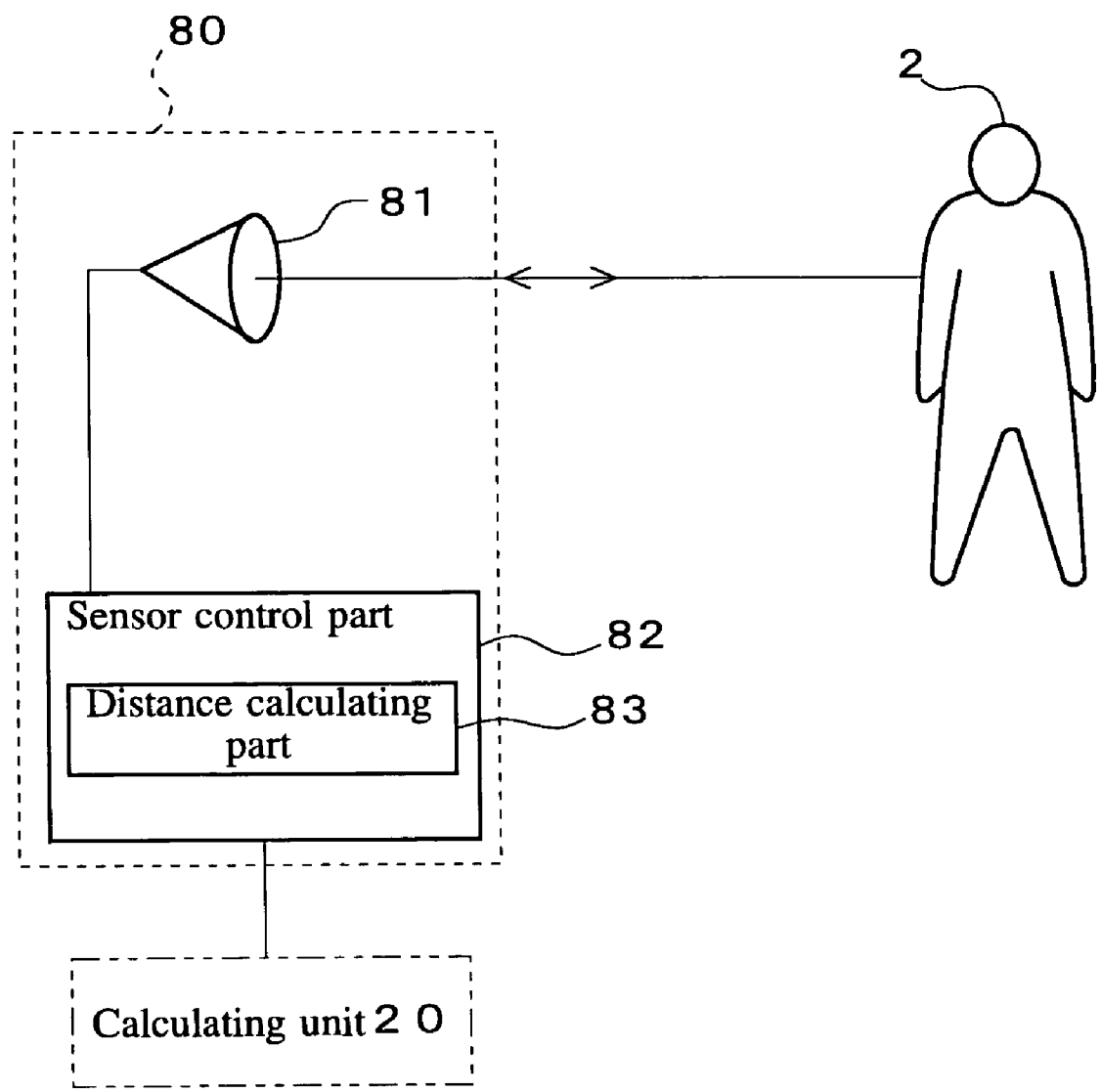
FIG. 16 is a block diagram illustrating a configuration example of an electromagnetic pulse distance sensor for use in the first embodiment of this invention.

Description will be made of an electromagnetic pulse distance sensor 80 in the embodiment of this invention with reference to the block diagram of FIG. 16. The electromagnetic pulse sensor 80 comprises an electromagnetic wave transmitting and receiving part 81 and a sensor control part 82. The electromagnetic wave transmitting and receiving part 81, which has an antenna, transmits pulse modulated electromagnetic waves toward the sleeping person 2 and receives electromagnetic waves reflected on the sleeping person 2. The sensor control part 82 has a distance calculating part 83 for calculating the distance to the sleeping person 2 based on the time difference between the transmission and reception of the electromagnetic waves. The sensor control part 82 may be incorporated in the control part 21 of the control unit 20. The electromagnetic wave transmitting and receiving part 81 may be separated into an electromagnetic pulse transmitting part and an electromagnetic wave receiving part. The distance to the sleeping person 2 may be the time difference as in the case with the ultrasonic wave sensor 70. The electromagnetic waves are typically microwaves of about 10 GHz.

The electromagnetic pulse distance sensor 80 using microwaves as the electromagnetic wave has a directivity which is higher than that of an ultrasonic wave distance sensor and thus can measure the corresponding objective point 5 with pinpoint accuracy. Also, since the electromagnetic pulse distance sensor 80 measures the distance based on the electromagnetic wave returned in the shortest period of time among the electromagnetic waves reflected on the object, it does not measure the distance erroneously, for example, although an infrared distance sensor does when an imaging beam light on the PSD moves off. Also, the electromagnetic pulse distance sensor 80 is not affected by strong contrast (such as a stripe pattern) in the emission region, although an infrared distance sensor is. In addition, the electromagnetic pulse distance sensor 80 can be easily downsized.

The infrared distance sensor 30, the ultrasonic wave sensor 70, and the electromagnetic wave pulse sensor 80 described above are emission type sensors.

Figure 17:
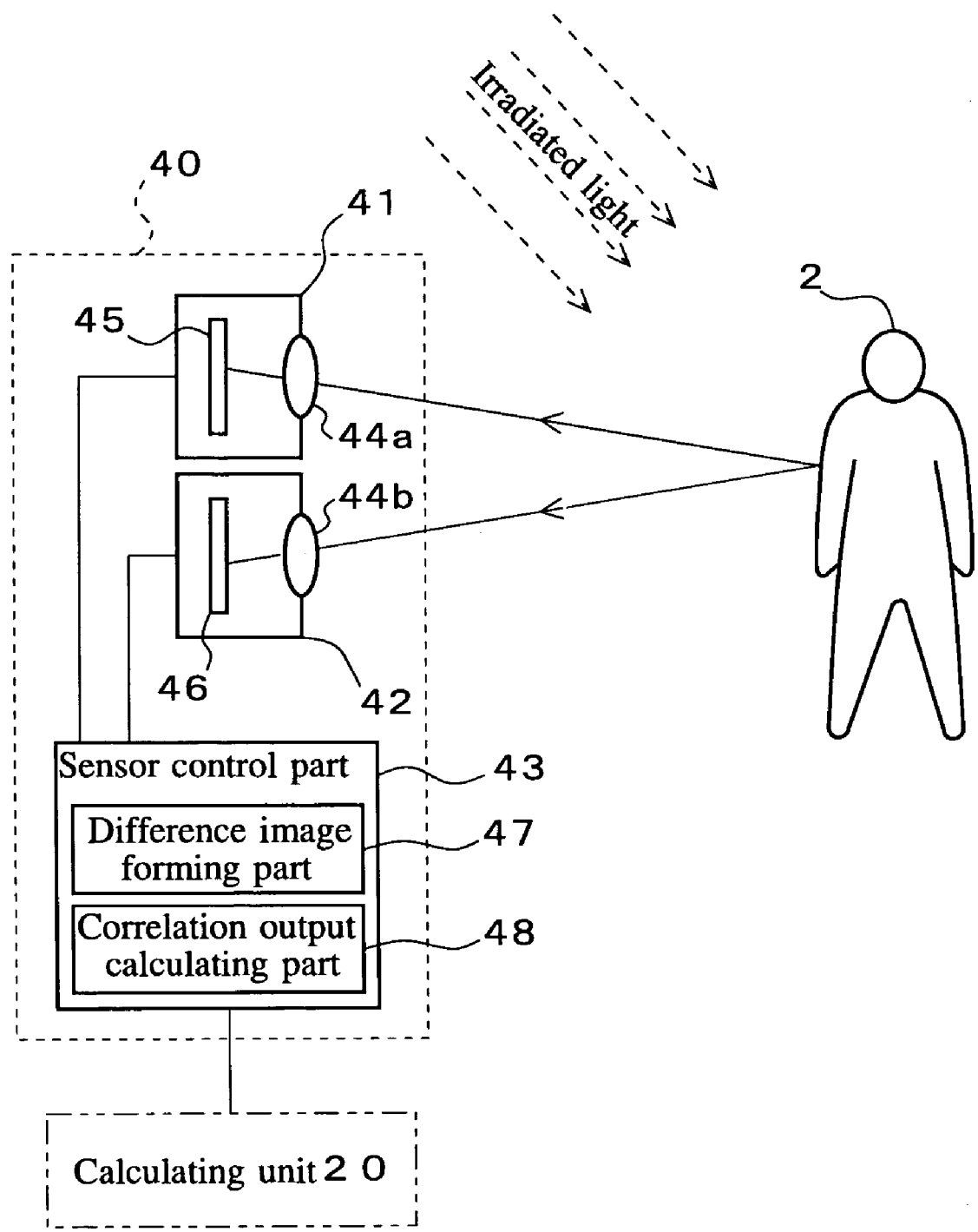
FIG. 17 a block diagram illustrating a configuration example of a passive optical distance sensor for use in the first embodiment of this invention.

Description will be made of a passive optical distance sensor 40 with reference to the block diagram of FIG. 17. The passive optical distance sensor 40 comprises a first light receiving part 41 and a second light receiving part 42 as imaging devices for receiving light from the sleeping person 2, and a sensor control part 43. The first light receiving part 41 and the second light receiving part 42 have light receiving lenses 44a and 44b, respectively, and a first line CCD 45 and a second line CCD 46, respectively, as a pair of image pickup element. Light from the sleeping person 2 is formed into images on the first line CCD 45 and the second line CCD 46 via the light receiving lenses 44a and 44b, respectively. The light from the sleeping person 2 is typically light irradiated on the sleeping person 2 and reflected thereon. The irradiated light may be natural light or artificial light.

As shown in FIG. 18, the passive optical distance sensor 40 may have illumination pattern emitting means (not shown) for emitting illumination light having a specific intensity pattern to the monitored area 50. In this case, the illumination pattern must not have a periodic structure so that a plurality of correlation peak positions described later will not appear. Namely, an periodic illumination pattern is preferably used. The periodic illumination pattern can be constituted of a plurality of periodic luminescent spots as shown in FIG. 18(*a*). Furthermore, the luminescent spots may have different sizes. Also, the periodic illumination pattern may be constituted of one or a plurality of periodic slit beams as shown in FIG. 18(*b*). In addition, the slit beams may have different intervals there between. In this case, the slit beams are preferably generally normal to the baseline direction of the distance sensors 11 as shown in the drawing. The passive optical distance sensor 40 can thereby prevent inaccurate correlation processing described later and perform accurate measurement even when the contrast of the objective point 5 is low or the object in the objective point 5 has a periodic structure (stripe pattern, for example).

The sensor control part 43 has a correlation output calculating part 48 as a correlation output calculating unit for calculating a correlation output value between the outputs from the first line CCD 45 and the second line CCD 46 respectively. Also, the sensor control part 43 may be incorporated in the control part 21 of the control unit 20. Furthermore, a difference image forming part 47 as a difference image forming unit for forming a difference image between images obtained from each of the first line CCD 45 and the second line CCD 46 at a time interval is preferably provided in the sensor control part 43. Thus, the sensor control part 43 can extract an image of the sleeping person 2 with movement from images obtained from the first line CCD 45 and the second line CCD 46. Two images for forming a difference image are obtained at a time interval. The interval may be set so that the sleeping person 2 cannot move largely and is regarded as being substantially in the same position during the interval. For example, the interval preferably is about 0.1 seconds. Or, the interval may be 1 to 10 cycles in television cycle (1/30 to ⅓). When such a difference image is formed, the background is removed and an image of the sleeping person 2 with movement can be extracted. The case where a difference image is used will be described later.

Here, the correlation output value is a relative difference between imaging positions generated by the parallax between the first line CCD 45 and the second line CCD 46, and is typically a value output as a number of pixels as a result of correlation processing. The sensor control part 43 calculates the distance from the correlation output value, namely the parallax between the first line CCD 45 and the second line CCD 46, by trigonometry. The correlation processing is an operation in which one of the images obtained from the first line CCD 45 and the second line CCD 46 is moved until the two images approximately overlap and the amount by which the image is moved, such as the number of pixels, is calculated. Judgment on whether the images overlap or not is made based on the intensity of all the signals. Where the intensity is highest is the position where the images overlap, namely the correlation peak position. In the correlation processing in difference image formation, a region with movement is extracted by diarizing each of the difference images obtained from the first line CCD 45 and the second line CCD 46 with a proper value to extract the edges thereof. Then, only the extracted region is subjected to correlation processing. Namely, the distance to the sleeping person 2 can be obtained from the correlation output value. When the first line CCD 45 and the second line CCD 46 are divided into a plurality of regions and correlation processing is performed on corresponding regions respectively, the region, a large portion of which is occupied by the background, can be roughly separated from the object.

The passive optical distance sensor 40, which is a sensor of the type used in an auto-focus camera, typically detects the brightness and darkness (difference in contrast) on a surface of the sleeping person 2 using a pair of line CCDs. The passive optical sensor 40 determines the pixels of the paired line CCDs corresponding to each other by correlation processing and measures the distance by trigonometry. The line CCDs generally used in the passive optical distance sensor 40 have a narrow field angle of about 10°. Thus, a relatively large number of sensors are needed to cover all the objective points 5. However, since the passive optical distance sensor 40 is not an emission type sensor, a plurality of sensors can be operated simultaneously without any problem. Thus, high-speed operation can be achieved. Also, since the passive optical distance sensor 40 compares relative positions on a pair of line CCDs, the passive optical distance sensor 40 is not as affected as an infrared distance sensor is affected when the beam is partially cut off, and can obtain the distance to the objective point 5 with stability.

Description will be made of a case in which a difference image is utilized in the passive optical sensor 40 to clearly distinguish the sleeping person 2 and the background in the objective point 5 in detail.

Photographed images of the objective points 5 are obtained from the first line CCD 45 and the second line CCD 46 in time series as electrical image signals. The difference image forming part 47 forms difference images from images obtained from each of the first line CCD 45 and the second line CCD 46 at different times, respectively. Here, the reason why the difference images are formed from images obtained at different times is to remove the background from the obtained images and extract the images of the sleeping person 2. Only the sleeping person 2, who is moving, is thereby extracted. The difference images are formed from images obtained at a short interval, 0.1 seconds, for example. Since the difference between the images is small, the difference in the position of the sleeping person 2 is small and does not affect the measurement of the distance. However, the background is deleted and the image of the sleeping person 2 can be extracted.

On the difference images in which the sleeping person 2 is extracted, the pixels, the brightness of which varied largely with movement of the sleeping person 2, can be regarded as the contour of the sleeping person 2. Then, correlation processing is performed on the pixels in the region inside the contour and the distance to the sleeping person 2 is measured by trigonometry. The distance to the sleeping person 2 can be thereby measured with precision and stability.

Figure 19:
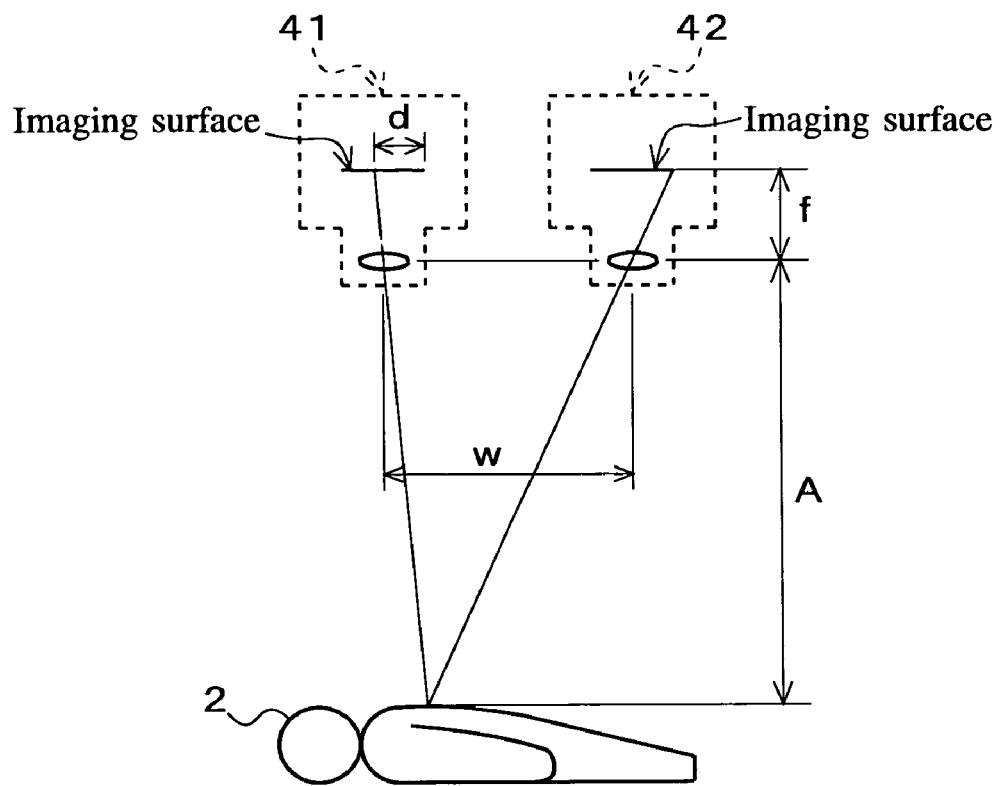
FIG. 19 a schematic view illustrating a method for calculating the distance to a monitored target from parallax between a pair of line CCD.

Description will be made of the method for calculating a distance A to the objective point 5 using the passive optical distance sensor 50 with reference to FIG. 19. Here, w is the distance between the line CCDs (baseline length), f is the focal length of the light receiving lenses of the line CCDs in the case where the light receiving lenses are single lenses, and d is the parallax on the imaging surface of each line CCD. When combination lenses used in general are used, the focal distance is the focal distance of the combination lenses. The distance A to the objective point 5 is calculated by the following equation:

$$A = w \times f / d \quad (2)$$

As has been described above, the distance to the sleeping person 2 can be obtained, namely measured, when any type of sensors described above are used as the distance sensors 11 of the monitoring device 1.

Description will be made of the monitoring device 1 in further detail with reference again to FIG. 3. The control unit 20 has a control part 21 for controlling the entire monitoring device 1. The plurality of distance sensors 11 are connected to the control part 21 and controlled thereby. The control part 21 is connected to a memory part 24 which can record data such as calculated information. In the memory part 24, a distance information storage part 25 for storing the distances output from the distance sensors 11 in time series is provided. In the distance information storage part 25, reference distances, which are the distances to the objective points 5 at the time when the sleeping person 2 is not on the bed 6, are preferably stored. The reference distances are stored in the same format as distances output from the distance sensors 11. The distances stored in the distance information storage part 25 in time series may be the distances obtained in the past before the time of monitoring. For example, the distances may be the distances obtained immediately before the time of monitoring.

The storage part 24 has a respiration pattern storage part 26 for storing the normal respiration pattern of the sleeping person 2 and abnormal respiration patterns. The normal and abnormal respiration patterns will be described later with reference to FIG. 22.

An input device 27 for inputting information to operate the monitoring device 1 and an output device 28 for outputting the results of processing in the monitoring device 1 are connected to the control part 21. The input device 27 is a touch panel, keyboard or mouse, for example. The output device 28 is a display or a printer, for example. The input device 27 and the output device 28, which are shown as external devices in the drawing, may be built in the control unit 20. The input device 27 may be a switch with which monitoring can be started or stopped, and the output device 28 may be an LED as an operation indicator. The monitoring device 1 can be thereby constituted in a simple manner.

The control part 21 is provided with an interface 29 for communicating with the outside. For example, when the sleeping person 2 is determined to be in a critical condition by a detection processing part 23 of the control part 21, the interface 29 reports the fact to the outside. The report is made by means of vocal sounds, letters, symbols, varying intensity of lights which may include room lighting, vibration, or the like. The interface 29 is connectable to a communication line such as a general telephone line, an ISDN line, a PHS line or a cellular phone line. The control part 21 may be provided with a sound output function so that it can inform a third person of the fact that the sleeping person is in a critical condition by sound through the interface 29.

The control part 21 also has an alarm device 90 which is activated when the monitoring device 1 develops a problem. The alarm device 90 is preferably configure to be activated when the detection processing part 23 determines that the sleeping person 2 is in a critical condition, namely the sleeping person 2 has a problem, or when the monitoring device 1 has an abnormality such as failure, for example. It is thereby possible to treat an abnormality of the sleeping person 2 quickly with high reliability. The control unit 20 is preferably configured to report occurrence of abnormality to the outside via the interface 29 when the alarm device 90 is activated as described above. The alarm device 90, which is shown as an external device in the drawing, may be an internal device.

The control part 21 has a calculating part 22 as a calculating unit for calculating changes over time in the distances output from a plurality of the distance sensors 11. The distance output from each of the distance sensors 11 may be the moving average value or term average value of a predetermined number of distances obtained in the past or distances obtained within a predetermined period in the past. Since random noises and accidental noises caused by flickers of sunlight shining in through a window can thereby be reduced, error in determining the peak position or zero-cross point (a point where the sign is reversed) can be reduced.

To calculate changes over time is to extract changes in shape of the sleeping person 2 by obtaining distances from the distance sensor 11 at predetermined time intervals and taking the difference between the distances obtained from the distance sensor 11 and the distances stored in the distance information storage part 25 in time series. This is to extract the respiration, motion or movement of the sleeping person 2, for example. The respiration of the sleeping person 2 extracted as described above forms a waveform pattern.

Figure 20:
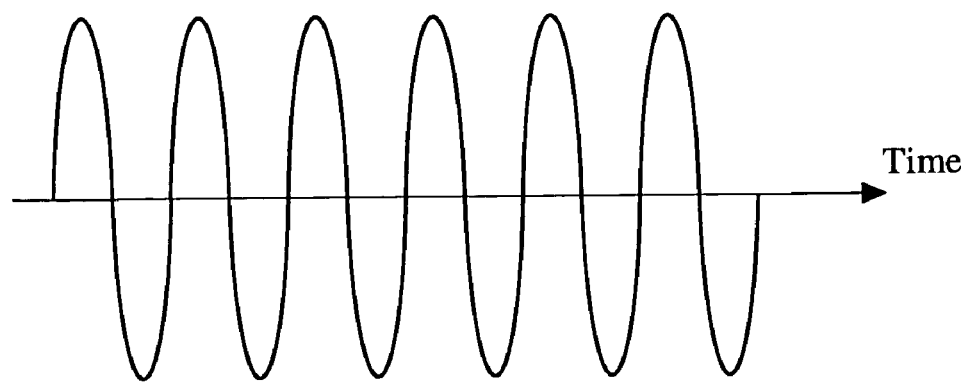
FIG. 20 is a schematic view illustrating a respiration waveform pattern of for use in the first embodiment of this invention.

FIG. 20 is a graph showing an example of a waveform pattern.

The control part 21 has a detection processing part 23 as a detection processor. The detection processing part 23 is configured to detect changes in shape of the sleeping person 2 based on the changes over time calculated by the calculating part 22. Namely, the detection processing part 23 is configured to detect the respiration, motion and movement of the sleeping person 2. The detection processing part 23 may be configured to detect changes in shape of the sleeping person 2 based on the changes over time relating to at least one distance sensor 11 selected from the plurality of distance sensors 11.

The detection processing part 23 may be configured to determine the condition of the monitored target based on either or both of the period and amplitude of periodic changes in the detected changes in shape.

Furthermore, the detection processing part 23 is configured to determine whether the sleeping person 2 is in the bed or not by comparing the distances to the objective points 5 with the reference distances stored in the distance information storage part 25. Also, the detection processing part 23 may be configured to select a distance sensor 11 which detected a distance to the corresponding objective point 5 with the largest difference from the reference distance and may detect the respiration, motion and movement of the sleeping person 2 based on the changes over time relating to the selected distance sensor 11.

The detection processing part 23 may be configured to determine whether the sleeping person 2 is in the bed or not after periodic changes (respiration of the sleeping person 2) has been detected in the detected changes in shape for a predetermined period of time. The monitoring device 1 may be configured to start determining whether the sleeping person 2 is in a critical condition or not on condition that the sleeping person 2 has been determined to be in the bed. The predetermined period of time is the period of time in which respiration can be detected with stability, and typically it is 30 to 120 seconds, more preferably 30 to 90 seconds.

The detection processing part 23 is preferably configured to determine that the monitored target 2 has deviated from the monitored area 50, namely the sleeping person 2 has left the bed when no periodic change is detected after a transitional change has been detected in the detected changes in shape and neither transitional change nor periodic change can be detected for a predetermined period of time or longer. The predetermined period of time is 1 to 3 minutes, for example. For example, when the sleeping person 2 really leaves the bed after motion or movement has been detected, the value of changes over time gradually decreases. Thus, judging only from the variation, the value comes in the range in which respiration is detected for some time and then becomes zero. Thus, the detection processing part 23 is configured to determine that the sleeping person 2 has left the bed when neither transitional changes nor periodic changes can be detected. However, when respiration was detected before this situation happens, it means that that the sleeping person 2 has been in a quiet state after motion or movement had been detected. Thus, when none of respiration, motion, or movement can be detected thereafter, the sleeping person 2 must be determined to be in a critical condition.

The detection processing part 23 is configured to monitor the period of periodic changes based on the detected continuous changes in shape of the sleeping person 2. Namely, the detection processing part 23 is configured to monitor the period of respiration of the sleeping person 2 based on the detected respiration, motion, and movement of the sleeping person 2. Also, the detection processing part 23 is configured to detect changes in shape of the sleeping person 2 based on either or both of the period and amplitude of periodic changes. Furthermore, the detection processing part 23 may be configured to monitor the respiration rate based on the period of the respiration. Here, monitoring the respiration rate is included in the concept of monitoring the period.

There are several methods by which the detection processing part 23 detects changes in shape of the sleeping person 2. Some typical examples will be hereinafter shown.

A first method for detecting changes in shape of the sleeping person 2 is a method in which a distance sensor 11 which detected the largest change over time within a predetermined period of time in the immediate past is selected from the plurality of distance sensors 11 and changes in shape of the sleeping person 2 are detected based on the changes over time detected by the selected distance sensor 11. In this case, it is good to select the distance sensor 11 which detected the largest variation in changes over time within a period of time for which the sleeping person 2 breathes a few times in the immediate past (a few seconds to ten and some seconds). The respiration, motion, and movement of the sleeping person 2 are reflected in changes over time in each of the objective points 5 in different manners depending on the positions of the objective points 5 corresponding to each of the plurality of distance sensors 11. Thus, to detect minute changes like respiration, the detection processing part 23 must select a distance sensor 11 which corresponds to changes over time reflecting the changes properly.

The thus selected distance sensor 11 may be changed when the sleeping person 2 makes motion such as rolling. In this case, a distance sensor 11 which detected the largest variation in changes over time within a predetermined period of time after the sleeping person 2 has become quiet is selected again to detect the respiration. In this case, one period of detected signals corresponds to one breath. When the sleeping person 2 is moving, a variation in changes over time, which is much larger than that by respiration, is detected and indicates that the sleeping person 2 is moving. The predetermined period of time is the time appropriate to select a distance sensor 11, which detects the largest variation in changes over time. In other words, the predetermined time is the time it takes until the fact that the sleeping person 2 has been in a quiet state is reflected in changes over time. The period of time is a few seconds (three seconds, for example) to about 20 seconds, preferably about 10 to 15 seconds in the case where only the amplitude of periodic changes is evaluated, and 30 to 90 seconds in the case where the respiration rate is evaluated by frequency analysis. The quiet state is the state where no transitional change, namely no motion or movement is detected. The state where no transitional change is detected can be determined by the following method as will be described in detail in the description of a second embodiment: it is determined that there has been a transitional change when the changes over time exceed a predetermined threshold value and it is determined that the state where no transitional change is detected has started when the changes over time fall below the threshold value.

The detection processing part 23 may be configured to select the distance sensors 11 which detected changes over time which exceed a predetermined value, to detect periodic changes in the selected changes over time, and to evaluate the presence or absence of respiration and the respiration rate based on the periodic changes with the clearest periodicity (which represents respiration).

A second method for detecting changes in shape of the sleeping person 2 is a method in which the detection processing part 23 selects all the distance sensors 11, obtains the total of changes over time in outputs from all the distance sensors 11, and detects changes in shape of the sleeping person 2 based on the total. This method, in which changes in shape of the sleeping person 2 are detected based on the total of the changes over time in the distances output from all the distance sensors 11, is not necessarily the most sensitive method but is the simplest method. Thus, high-speed processing can be easily achieved. The total of the changes over time in the distances may be the total of the differences between the distances output from the distance sensors 11 and the reference distances. In this case, one period of detected signals corresponds to one breath.

A third method for detecting changes in shape of the sleeping person 2 is the method in which the detection processing part 23 selects changes over time having absolute values which are greater than a predetermined value and detects changes in shape of the sleeping person 2 based on the average of the selected changes over time. In this method, changes in shape of the sleeping person 2 are detected based on the average of the changes over time in the distances. Thus, local large motion of the sleeping person 2 is flattened into motion with magnitude which is close to that of the motion of respiration and prevented from influencing the detection of the respiration of the sleeping person 2. In this case, one period of detected signals corresponds to one breath.

A fourth method for detecting changes in shape of the sleeping person 2 is a method in which the detection processing part 23 selects changes over time having absolute values which are greater than a predetermined value and detects changes in shape of the sleeping person 2 based on the average of the absolute values of the changes over time. In this method, changes in shape of the sleeping person 2 are detected based on the average of absolute values of changes over time in the distances. Thus, for example, when a plurality of changes over time having absolute values which are greater than a predetermined value are selected and when the detected changes over time in the distances include positive and negative values, they are not cancelled out but added up. The method is therefore sensitive to small changes such as respiration. In this case, two periods of detected signals correspond to one breath.

A fifth method for detecting changes in shape of the sleeping person 2 is a method in which the detection processing part 23 compares the phases of the changes over time relating to a plurality of selected distance sensors 11 each other, classifies the changes over time into groups according to the similarity of the phases, obtains the total of the changes over time in each group, calculates the difference between the totals of the groups, the groups having phases approximately opposite to each other, and detects changes in shape of the sleeping person 2 based on the value obtained by the calculation. In this method, the changes over time having similar phases are grouped together and the total thereof is obtained respectively. Thus, the breaths of the sleeping person 2, for example, can be extracted as members of a group and amplified. In addition, the difference between the totals of the groups having phases approximately opposite to each other is calculated and changes in shape of the sleeping person 2 are detected based on the value obtained by the calculation. Thus, even though some values are raised and other values are lowered simultaneously as the sleeping person 2 breathes, the amplitude of the respiration pattern can be amplified by the subtraction and the respiration can be detected reliably. In this case, one period of detected signals correspond to one breath.

A sixth method for detecting changes in shape of the sleeping person 2 is a method in which the detection processing part 23 calculates the frequency spectra of all the outputs from a plurality of the distance sensors 11, selects the distance sensor 11 whose output has a frequency spectrum with a peak having a sharpness which is a predetermined value or higher and the highest among the calculated frequency spectra, and then detects changes in shape of the monitoring object 2 based on the changes over time relating to the selected distance sensor 11.

A value obtained by dividing the height of the peak of a spectrum by the integration value of the heights of the spectra of all frequencies or, in a discreet case, a value obtained by adding the height of the higher spectrum of the spectra next to the peak to the height of the peak and further dividing by the sum of the heights of the spectra of all frequencies can be used as the index of the sharpness of the peak, for example. By evaluating the fact that the sharpness of the peak is a predetermined value or higher, a distance sensor 11 which is distinctly detecting the respiration of the sleeping person 2, for example, can be selected. Thus, the respiration of the sleeping person 2 can be easily detected.

A seventh method for detecting changes in shape of the sleeping person 2 is a method in which the detection processing part 23 calculates the frequency spectra of outputs from the distance sensors 11 which detected a change over time having an absolute value within a predetermined range, selects a distance sensor 11 whose output has a frequency spectrum with a peak having a sharpness which is a predetermined value or higher and the highest among the calculated frequency spectra, and detects changes in shape of the monitored object 2 based on the changes over time relating to the selected distance sensor 11. In this method, when the predetermined range of the absolute values of the changes over time is set within the region in which the respiration of the sleeping person 2 falls, the respiration of the sleeping person 2 can be easily detected.

An eighth method for detecting changes in shape of the sleeping person 2 is a method in which the detection processing part 23 calculates the frequency spectra of outputs from a plurality of the distance sensors 11 which detected a change over time having one of the largest absolute values, selects a distance sensor 11 whose output has a frequency spectrum with a peak having a sharpness which is a predetermined value or higher and the highest among the calculated frequency spectra, and detects changes in shape of the monitoring object 2 based on the changes over time relating to the selected distance sensor 11.

The detection processing part 23 detects changes in shape of the sleeping person 2 using the above detection method shown above. The monitoring device 1 determines the condition of the sleeping person 2 based on the thus detected changes in shape. For example, when the period of respiration pattern becomes irregular within a short period of time or varies suddenly, the sleeping person 2 may have a lung disease such as spontaneous hem thorax or bronchial asthma, a heart disease such as congestive heart failure, or a cerebrovascular disease such as cerebral bleeding. When the respiration pattern does not appear continuously, the sleeping person 2 may have stopped respiration. Also, when not respiration pattern but motions of the sleeping person 2 frequently appear within a short period of time, the sleeping person 2 may be suffering and struggling for some reason.

The motion or movement of the sleeping person 2 can be detected easily since the detection value largely varies as compared with the case in which only respiration is detected based on changes over time. In this case, furthermore, The detection processing part 23 can detect whether the sleeping person 2 is making motion such as rolling on the spot or moving to get out of the bed, for example, based on each of the changes over time corresponding to a plurality of the distance sensors 11. Also, when the sleeping person 2 makes periodic small motions such as spasm, the abnormality can be detected based on the waveform pattern. Furthermore, when a waveform pattern at the time when a sleeping person is having a spasm is stored in the memory part 24, it can be determined that the sleeping person 2 is having a spasm.

Description will be made of examples of normal and abnormal respiration patterns with reference to FIG. 21. A normal respiration pattern stored in the respiration pattern storage part 26 in the memory part 24 is a periodic pattern as shown in FIG. 21(*a*). In the case of an adult, the number of breaths per minute is normally in a range of about 10 to 20. Abnormal respiration patterns stored in the respiration pattern storage part 26 are respiration patters which are considered to occur when a sleeping person has a physiological defect, such as Cheyne-Stokes respiration, central hyperventilation, ataxic respiration, and Kussmaul respiration.

FIG. 21(*b*), FIG. 21(*c*), and FIG. 21(*d*) show a pattern of Cheyne-Stokes respiration, a pattern of central hyperventilation, and a pattern of ataxic respiration, respectively.

FIG. 22 shows the names of the diseases and diseased sections which cause the abnormal respiration patterns.

The detection processing part 23 determines to which pattern the respiration pattern of the sleeping person 2 belongs utilizing the fact that the respiration patterns have different frequencies, numbers of appearances, and amplitudes, and determines the conditions of the sleeping person 2.

The detection processing part 23 determines that the sleeping person 2 is breathing abnormally and thus in a critical condition when the respiration of the sleeping person 2 is determined to belong to a respiration pattern which is considered to occur when there is a physiological defect. The condition of the sleeping person 2 detected as above is output from the output device 28 by the control part 21. Here, the output includes the detected respiration rate and frequency of motion of the sleeping person 2, the name of the abnormal respiration pattern, the name of disease, diseased organ, or diseased section, which is considered to be the cause of the abnormal respiration pattern.

The monitoring device 1, which has a plurality of distance sensors 11 in the above description, may have only one distance sensor 11. In this case, the monitoring device 1 can be simplified and downsized. Also, the monitoring device 1 can perform high-speed operation since the number of outputs from the distance sensor 11 is small. Furthermore, when the infrared distance sensors 30*a* are used as the distance sensors 11, the circuit structure can be simplified since the monitoring device 1 is provided with distance sensors 11 each using bipartite PD. Thus, the monitoring device 1 can be cost-effective and simple.

According to the first embodiment as described previously, the respiration of the sleeping person 2 can be detected reliably and the condition of the sleeping person 2 can be determined. In addition, the monitoring device 1 does not use image processing using a camera, which may give a psychologically uncomfortable feeling, and high-speed processing can be achieved although it is simple. When an aged person or patient falls into a critical condition, life-saving measures can be quickly taken.

Description will be made of a monitoring device 201 according to a second embodiment of this invention with reference to the schematic perspective view of FIG. 23. As shown in FIG. 23(*a*), a monitored region 250 as a monitored target area is set on the upper surface of a bed 206. As shown in FIG. 23(*b*), a sleeping person 202 as a monitored target lies on the bed 206. A bed cloth 203 is laid over the sleeping person 202 and covers part of the sleeping person 202 and part of the bed 206. Namely, when the sleeping person 202 lies on the bed 206 (is in the bed), the monitoring device 201 monitors the upper surface of the bed cloth 203. When the bed cloth 203 is not used, the monitoring device 201 monitors the body of the sleeping person 202. The monitored region 250 will be described later with reference to FIG. 25. In this embodiment, the periodic changes of the sleeping person 202 are, for example, the respiration of the sleeping person 202. The transitional changes of the sleeping person 202 are motion or movement of the sleeping person 202.

As shown in FIG. 23(*a*), a plurality of distance sensors 211 as sensors for detecting distance information as a variable having a correlation with the distance to the sleeping person 202 are installed in a ceiling 204. The distance information in this embodiment is a distance value which is a distance as it is or an output value corresponding to the distance value. These will be hereinafter referred to simply as "distance". Description will be hereinafter made using the term "distance".

The plurality of distance sensors 211 are preferably installed in the ceiling via a casing 210. The plurality of distance sensors 211 can thereby be installed with ease since there is no need to install the sensors one by one. In the casing 210, the plurality of distance sensors 211 are arranged corresponding to a plurality of objective points 205 (distance measurement points). In other words, the distance sensors 211 correspond in number with the objective points 205 and are oriented to corresponding objective points 205. The objective points 205 will be described later in detail with reference to FIG. 25. The casing 210 (the distance sensors 211), which is installed in the ceiling 204 in this embodiment, may be installed in a wall if possible. The installation position may be determined depending upon the purpose or type of the monitoring device.

Figure 24:
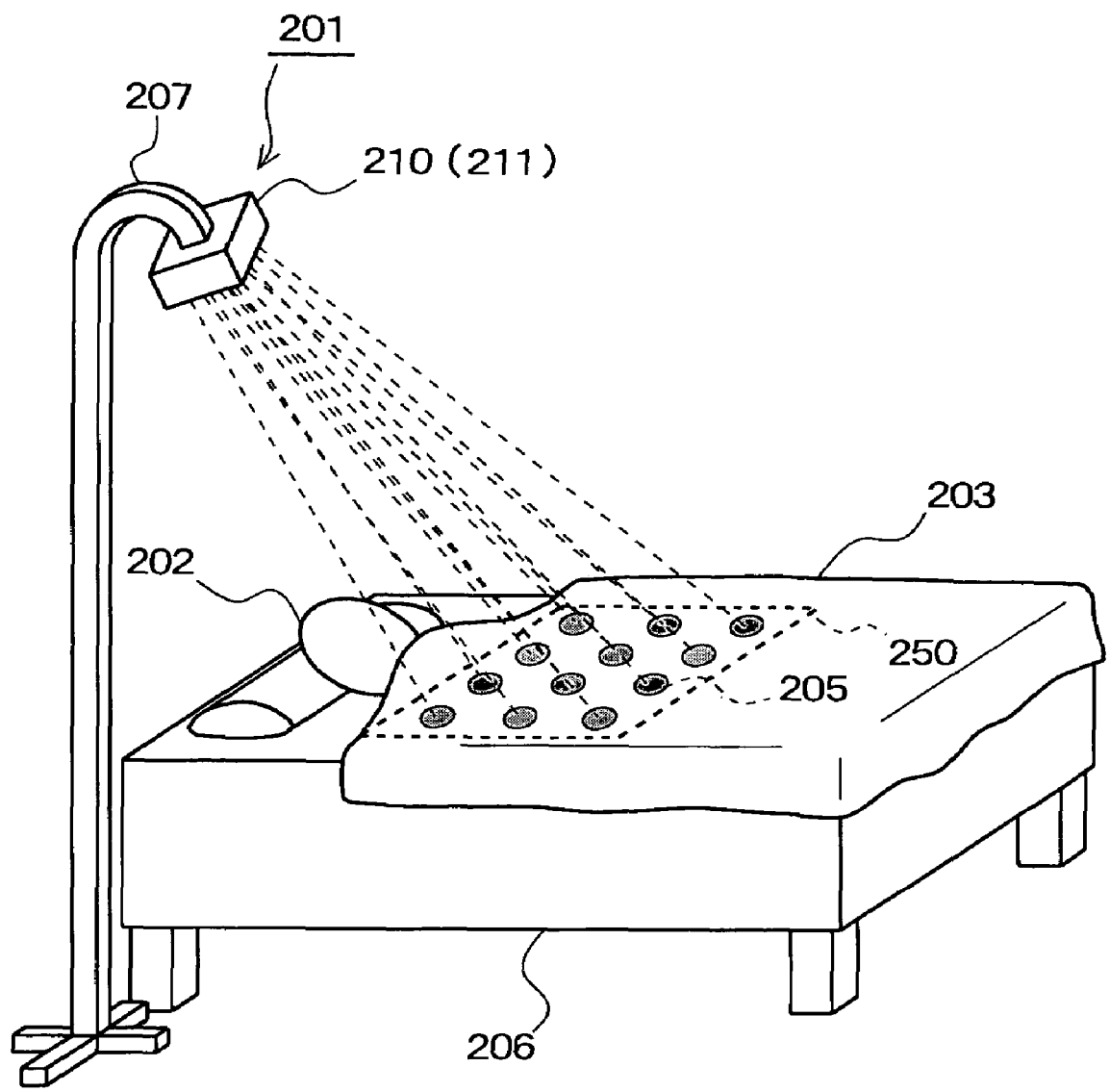
FIG. 24 is a schematic perspective view illustrating a case in which a casing of the monitoring device is mounted on a stand.

As shown in FIG. 24, the casing 210 may be mounted on a movable stand 207. The plurality of distance sensors 211 can thereby be placed easily. For example, the distance sensors 211 can be conveniently placed when and where needed in a hospital or the like.

Description will be made of examples of arrangement of the objective points 205 with reference to the schematic plan view of FIG. 25. The objective points 205 are arranged in the monitored region 250. Also, the objective points 205 are preferably arranged in at least two columns in the monitored region 250. FIG. 25(*a*) shows an example in which a plurality of objective points 251*a* to 254*c* corresponding to the plurality of distance sensors 211 are arranged in such a manner that they do not overlap with each other.

In this case, the plurality of objective points 205 are arranged so that they do not overlap with others as follows, as shown in the drawing: the objective points 251*a*, 251*b*, 251*c*, 254*a*, 254*b*, and 254*c* are placed in the vicinity of the sides of the bed 206; and the objective points 252*a*, 252*b*, 252*c*, 253*a*, 253*b*, and 253*c* are placed in the vicinity of the center of the bed 206 in the monitored region 50 (the objective points will be hereinafter referred to as "objective points 205 when they are not mentioned separately). Also, the objective points 205 are preferably arranged in a grid pattern as shown in the drawing. The objective points 205 are preferably arranged in an area which covers the area in which the chest, abdomen, back, and shoulders of the sleeping person 202 on the bed 6 (under the bed cloth 3) move while it is sleeping. Although the objective points 205 are arranged in a matrix of four rows by three columns (which will be hereinafter represented as "4×3") in this embodiment, the number of the objective points 205 can be determined depending upon conditions, such as the place to be monitored and the sleeping person 202. The objective points 5 may be arranged in, for example, 3×3, 4×4, or 2×2.

When the objective points 205 are arranged as described above, a wide monitored region 250 can be covered with a relatively small number of distance sensors with high efficiency. Namely, since the monitored region 250, which covers an area required to be monitored, can be monitored with a relatively small number of distance sensors 211, the monitoring device 201 (see FIG. 23) can be small and highly effective. Also, even when emission type sensors which measure distance by emitting light flux as described in the description of the first embodiment are used for the distance sensors 211, the distance sensors 211 corresponding to adjacent objective points 205 do not have to be so controlled as not to make emission simultaneously. Thus, the monitoring device 201 can be simpler in structure.

As shown in the arrangement example of FIG. 25(b), adjacent objective points 205 may overlap with each other. In this case, since blind areas in the monitored region 250 can be reduced, monitoring can be performed with higher precision. When emission type sensors which measure distance by emitting light flux as described in the description of the first embodiment are used as the distance sensors 211, for example, the distance sensors 211 corresponding to the objective point 205 overlapping with each other must be so controlled as not to make emission simultaneously. This is because when a plurality of distance sensors 211 emit light, for example, simultaneously, the light which must be received is mixed with and influenced by light emitted from other distance sensors 211, making it difficult to measure the distance.

When the distance sensors 211 emit light fluxes with different wavelengths as in the case with the infrared distance sensors 30a (see FIG. 5) as described in the description of the first embodiment and when the light receiving lenses 37a (see FIG. 5) are made to transmit light in a wavelength band corresponding to that of the emitted beam light by means of coating or the like, the distance sensors 30a does not have to be so controlled as not to make emissions simultaneously even when adjacent objective points 205 overlap with each other. Also, when the light sources of the emitted light flux are blinked at prescribed frequencies, as in the case with the infrared distance sensors 30a, which are different from each other among the distance sensors 211 and electric band pass filters for extracting signals with the frequencies are provided with the distance sensor 211, the distance sensors 211 do not have to be so controlled as not to make emissions simultaneously even when adjacent objective points 205 overlap with each other.

Figure 26:
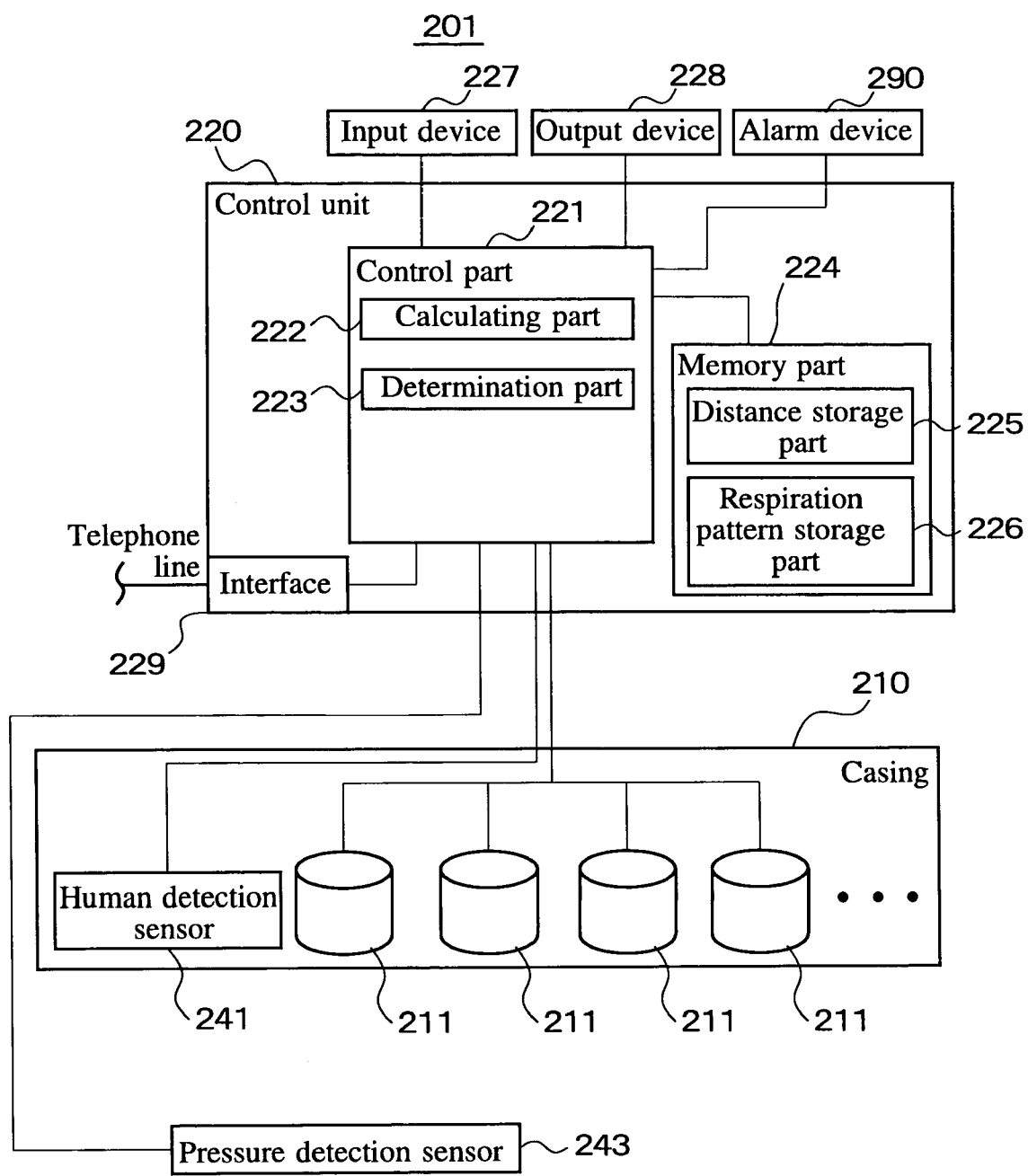
FIG. 26 is a block diagram illustrating a configuration example of the monitoring device for use in the second embodiment of this invention.

Description will be made of an example of the configuration of the monitoring device 201 with reference to FIG. 26. The monitoring device 201 comprises a casing 210 in which a plurality of distance sensors 211 are installed and a control unit 220. The control unit 220 is typically a personal computer or microcomputer. The plurality of distance sensors 211 are connected to the control unit 220 and configured to output distances to the control unit 220. The distances are preferably obtained from each of the distance sensors 211 in time series. The distance sensors 211 and the control unit 220, which are shown as being separate in the drawing, may be integrated together. The distance sensors 211 are arranged in the casing 210 in 4×3.

Although the distance sensors 211 are typically aligned in the casing 210, the casing 210 may be curved as in the case with the housing 10'described before with FIG. 4. In this case, the distance sensors 211 are arranged along the curve. When the casing 10' is used, the wide monitored region 250 can be easily secured even when the casing 10' is small. The casing 10' enables the distance sensors 211 to be arranged in such a manner that adjacent objective points 205 do not overlap with each other with ease even when the casing 10' is small. Thus, the device can be downsized.

As the distance sensors 211 for use in the monitoring device 201, infrared emitting distance sensors, ultrasonic wave sensors, electromagnetic pulse distance sensors, passive optical distance sensors, or the like can be used. Among them, infrared emitting distance sensors, ultrasonic wave sensors, and electromagnetic pulse distance sensors are emission type sensors. As the distance sensors 211, relatively simple and inexpensive sensors such as sensors used in auto-focus cameras are preferably used in the above description. By using such distance sensors 211, the monitoring device 1 can be simple and cost-effective. The infrared emitting sensors described with FIG. 5 and FIG. 13, ultrasonic wave sensors described with FIG. 15, electromagnetic distance wave sensors described with FIG. 16, or passive optical distance sensor described with FIG. 17 can be preferably used. In this embodiment, description will be made of the case in which the infrared distance sensors 30 described in the description of the first embodiment are used.

With any type of distance sensors described as above, the distance to the sleeping person 202 can be obtained, namely, the distance to the sleeping person 202 can be measured.

Referring again to FIG. 26, the monitoring device 201 will be described in further detail. The control unit 220 has a control part 221. The control part 221 controls the entire monitoring device 201. The plurality of distance sensors 211 are connected to the control part 221 and controlled thereby. The control part 221 is connected to a memory part 224 which can record data such as calculated information. In the memory part 224 is provided a distance storage part 225 for storing the distances output from the distance sensors 211 in time series. The distances stored in the distance storage part 225 in time series may be the distances obtained in the past before the time of monitoring. The distances may be the distances obtained immediately before the time of monitoring.

An input device 227 for inputting information to operate the monitoring device 201 and an output device 228 for outputting the result of processing in the monitoring device 201 are connected the control part 221. The input device 227 is a touch panel, keyboard, or mouse, for example. The output device 228 is a display or printer, for example. The input device 227 and the output device 228, which are shown as external devices in the drawing, may be built in the control unit 220. The input device 227 may be a switch with which monitoring can be started or stopped, and the output device 228 may be an LED as an operation indicator. The monitoring device 201 can be thereby constituted in a simple manner.

The monitoring device 201 has an alarm device 290 as alarming means for issuing an alarm. The alarm device 290 is connected to the control part 221. The alarm device 290 is configured to issue an alarm when it receives an alarm signal from a hereinafter described determination part 223. Namely, the alarm device 290 is configured to issue an alarm when the determination part 223 determines that the sleeping person. 202 is in a critical condition. The alarm device 290 may be configured to issue an alarm when an abnormal event such as breakdown of the monitoring device 201 occurs. Since it is therefore possible to inform a third person of the fact that the sleeping person 202 is in a critical condition quickly, necessary measures can be taken quickly. Namely, the monitoring device 201 can have high reliability in monitoring. The alarm device 290, which is shown as an external device in the drawing, may be an internal device.

The control unit 220 is preferably configured to report the fact that the alarm device 290 issues an alarm to the outside via an interface 229 when the alarm device 290 issues an alarm. The outside herein is the place from which the monitoring device 201 is managed, or, in the case of a personal home, a living room or a fire station. The report is made by means of vocal sounds, letters, symbols, varying intensity of lights which may include room lighting, vibration, or the like. The interface 229 is connectable to a communication line such as a general telephone line, an ISDN line, a PHS line, or a cellular phone line. In a personal home, the report to another room such as the living room or another bed room is preferably made by radio or power line communication. The control unit 220 may be provided with a sound output function so that it can inform a third person of the fact that the person is in a critical condition by sound through the interface 229.

The control unit 220 has a human detection sensor 241 as presence detecting means for detecting the sleeping person 202 present in or in the vicinity of the monitored region 250. As the human detection sensor 241, a piezoelectric sensor which can detect the presence of a human by detecting heat rays, an ultrasonic sensor which detects the presence of a human using ultrasonic waves, a motion sensor using image processing can be used. A piezoelectric sensor is preferably used as the human detection sensor 241. By using a piezoelectric sensor, the monitoring device 201 can be small and cost-effective. The human detection sensor 241 functions as a motion sensor which detects fluctuations in a detection level since it is difficult to distinguish environmental changes and changes due to the presence or absence of the sleeping person 202 based on absolute values of detection levels.

The human detection sensor 241 is preferably installed in the casing 210. The work to install the monitoring device 201 can be thereby facilitated and the monitoring device 201 can be downsized. The installation position of the human detection sensor 241 is not limited to the above. The human detection sensor 241 may be installed in any position as long as it can detect the sleeping person 202 present in the monitored region 250 or around it.

When the monitoring device 201 is provided with the human detection sensor 241, power can be saved since power supply to the monitoring device 201 can be cut off when the human detection sensor 241 cannot detect the presence of the sleeping person 202 in or in the vicinity of the monitored region 250. In other words, since power can be supplied to the monitoring device 201 when necessary, power can be saved. Also, when the distance sensors 211 cannot detect a motion of the sleeping person 202, the human detection sensor 241 can help determine whether the sleeping person 202 is present or not or whether the person is making a motion or not.

A pressure detection sensor 243 may be provided as a device for detecting whether the sleeping person 202 is present or absent. The pressure detection sensor 243 is a load sensor or a pressure sensor, for example. The pressure detection sensor 243 is preferably located in a position where the load of the sleeping person 202 on the bed 206 is applied such as a position on the side of the upper body of the sleeping person 202 on the bed 206 or in one of the legs of the bed 206 (which are located at the four corners of the rectangular bed 206) on the side of the upper body of the sleeping person 202. In this case, by utilizing the output from the pressure detection sensor 243, the reliability in determining whether the sleeping person 202 is in the bed or not can be improved.

The control part 221 also has a calculating part 222 as a calculating unit for calculating distance-related values based on the distances output from the distance sensors 211, and a determination part 223 as a determination unit for determining the presence or absence of changes in shape of the sleeping person 202 based on the calculated distance-related values.

Here, the distance-related values calculated by the calculating part 222 are changes in the distances with time or the absolute values of the changes over time. Herein below, this embodiment is described where the distance-related values are the absolute values of changes in the distances with time. The changes in shape of the sleeping person 202 are continuous changes in shape, for example. The continuous changes in shape are periodic changes. The periodic changes are respiration of the sleeping person 202, for example.

To calculate changes over time based on the distances means to obtain the displacement in the distances within a predetermined period of time in the past by obtaining distances from the distance sensor 211 at predetermined intervals and calculating the difference between distances obtained at the time of monitoring and distances obtained in the past. In other words, it is to obtain the displacement in the distances within a predetermined period of time in the past by calculating the difference between distances obtained from the distance sensor 211 and the distances stored in the distance storage part 225 in time series. To calculate changes over time based on the distances may be to obtain the displacement in the distances within a predetermined period of time in the past by obtaining distances from the distance sensor 211 at predetermined intervals and calculating the differences between the maximum values and minimum values (Max–Min) of the distances obtained in a predetermined period of time in the past. Here, the former is suitable to detect periodic changes. The latter is suitable to distinguish hereinafter described the respiration, motion or sitting-up of the sleeping person 202. Although description will be made of the case in which the latter distance displacement is used, the former may be used. Alternatively, both of the distance displacements may be used. In this case, a hereinafter described determination part 223 selects which to use. The detection of periodic changes may not be necessarily performed using a difference between distances and may be performed by means of frequency analysis or the like based on distances obtained in time series.

Here, the interval at which distances are obtained from the distance sensors 211 is about 0.1 to 3 seconds, preferably about 0.1 to 0.5 seconds. However, when the distances obtained include random noises, distances are preferably obtained at shorter intervals and subjected to averaging or filtering. The predetermined period of time here is about 30 seconds, preferably about 10 to 20 seconds, and may be a shorter period of time such as about 3 seconds. When the predetermined period of time is relatively long, it is useful for hereinafter described the determination part 223 to determine that the sleeping person 202 is sitting up. When the predetermined period of time is relatively short, it is useful for the determination part 223 to detect motion of the sleeping person 202.

Preferably, a first predetermined period and a second predetermined period, which is shorter than the first predetermined period, are set and the calculating part 222 obtains both of distance displacement within the first predetermined period and distance displacement within the second predetermined period. In this case, in the same manner as above, the first predetermined period is set to about 30 seconds, preferably about 10 to 20 seconds, and the second predetermined period is set to about 1 to 10 seconds, preferably about 3 to 6 seconds. The determination part 223 thereby can make a more accurate determination. The predetermined periods, which are time periods in the above description, may be numbers of distances obtained (ten, for example). The calculation of changes over time is performed for each distance sensor 211. Namely, distance displacement is obtained for each distance sensor 211.

The distance displacements obtained by calculating changes over time based on the distances in the calculating part 222 are arranged in chronological order to form a waveform pattern.

Figure 27:
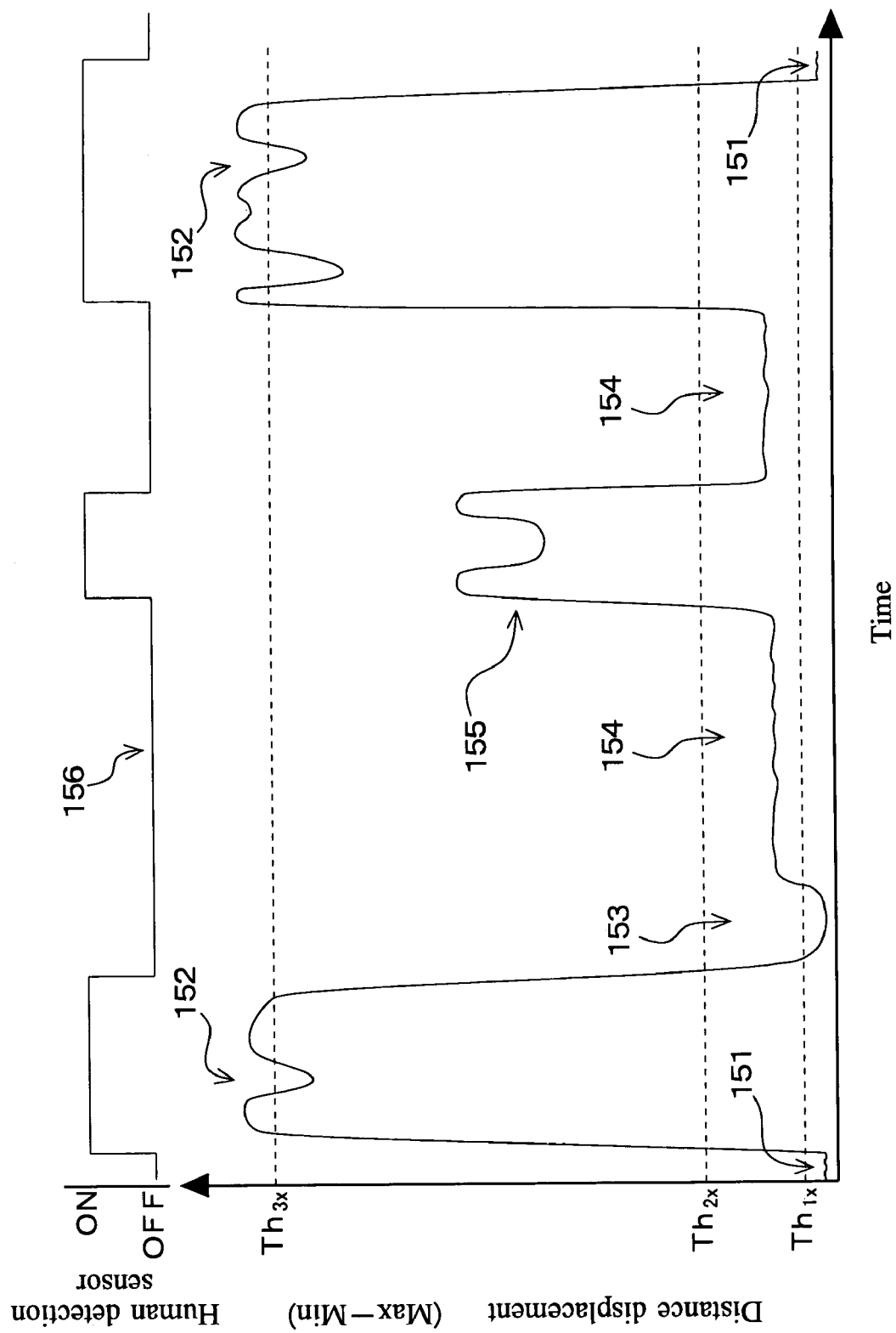
FIG. 27 is a graph showing an example of a waveform pattern of changes over time for use in the second embodiment of this invention.

FIG. 27 shows an example of a waveform pattern formed by the changes over time. Shown is a waveform pattern corresponding to normal actions of the sleeping person 202: getting into the bed, quiet state, rolling, quiet state, sitting-up, and leaving the bed from the left. Shown is the case where the predetermined period is set to about 15 seconds.

The distance-related values, which are changes in distances with time or particularly absolute values of the changes over time in the above description, may be the distances from a reference position. In this case, to calculate distance-related values based on the distances is to obtain distances from the reference position at predetermined intervals. The thus obtained distances are arranged in chronological order. Here, the reference position, which is typically the upper surface of the bed 206, may be a position on the breast or abdomen of a sleeping person 202 with a standard body shape. The reference position is preferably stored as the distance from the distance sensor 211 to the reference position in the distance storage part 225. The hereinafter described determination part 223 can thereby easily determine the sitting-up.

As has been described above, the distance-related values are formed into a waveform pattern by calculation of the calculating part. 222.

Figure 28:
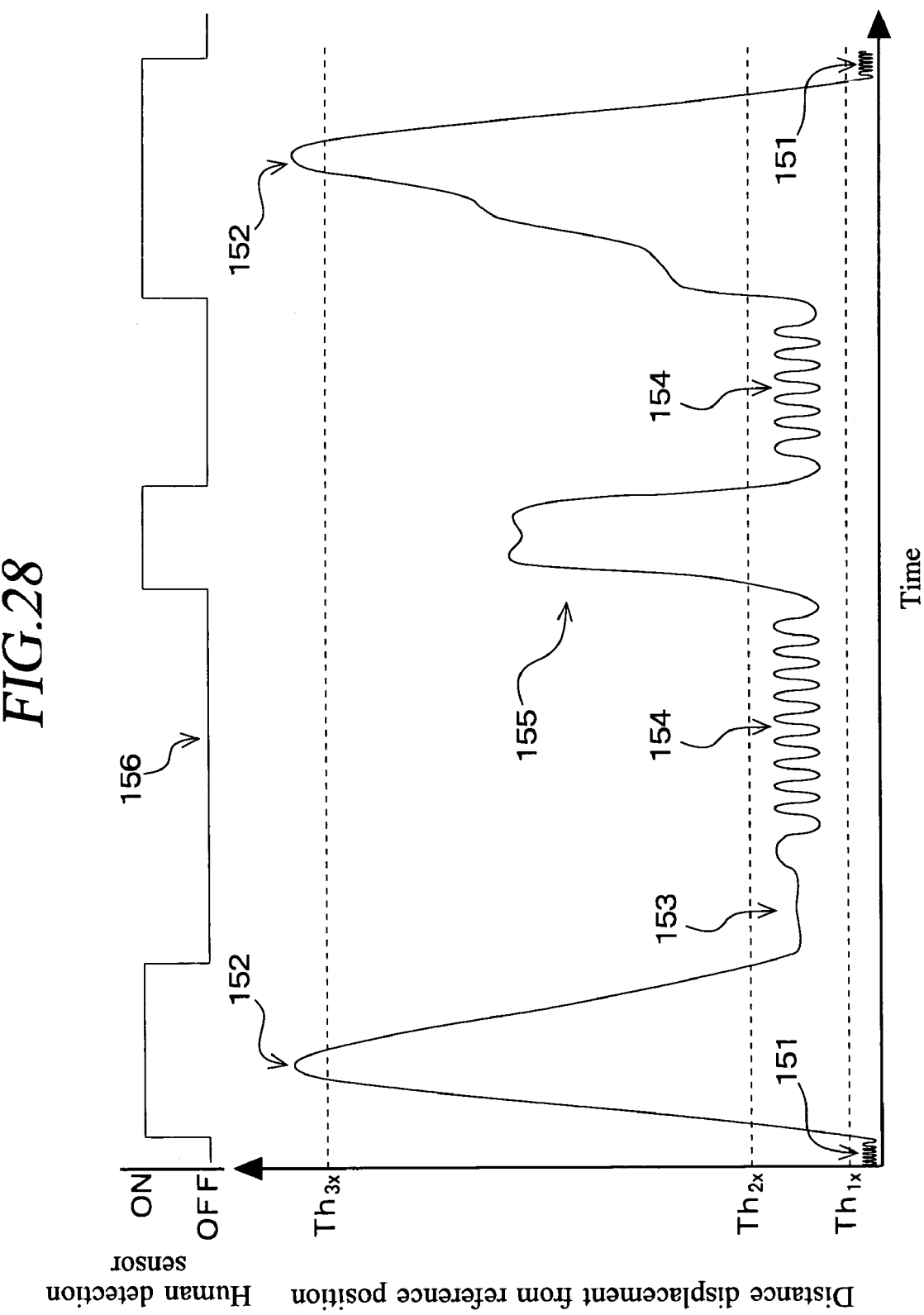
FIG. 28 is a graph showing an example of a waveform pattern of distance displacement from a reference position.

FIG. 28 shows an example of a waveform pattern formed by the distance-related values. This is an example in the case where the reference position is set on upper surface of the breast of the sleeping person 202 having a standard body shape. Shown is a waveform pattern corresponding to normal actions of the sleeping person 202 as in the case with the waveform pattern shown in FIG. 27.

Description will be made of the case where the distance-related values are changes in the distances with time with reference to FIG. 27 as necessary.

The calculating part 222 may be configured to calculate the moving average value or term average value of a predetermined number of distances obtained in the past or distances obtained within a predetermined period of time in the past. In this case, the thus calculated moving average value or term average value of the distances are treated in the same manner as the distances output from the distance sensors 211 when the calculating part 222 calculates changes in the distances with time. In other words, the calculating part 222 calculates changes in the distances with time based on the moving average value or term average value. The moving average value or term average value may be calculated in each distance sensor 211. In other words, the distance sensors 211 may be configured to calculate the moving average value or term average value of the measured distances and output the result of the calculation as the distance. Since random noises and accidental noises caused by flickers of sunlight shining in through a window or the like can thereby be reduced, error in determining the peak position or zero-cross point (a point where the sign is reversed) can be reduced.

The calculating part 222 may be configured to receive distances within a predetermined range among distances output from the distance sensors 211. This can be easily accomplished by a band pass filter or low-pass filter. A hereinafter described first threshold value $Th_{1x}$ can be thereby set to a relatively low value, and a hereinafter described determination part 223 can determine the presence or absence of changes in shape of the sleeping person 202 more accurately.

Description will be made of the determination part 223. In the determination part 223, a first threshold value $Th_{1x}$, a second threshold value $Th_{2x}$, which is greater than the first threshold value $Th_{1x}$, and a third threshold value $Th_{3x}$, which is greater than the second threshold value $Th_{2x}$, are set. The first threshold value $Th_{1x}$ is a value corresponding to a distance displacement of about 0.1 to 3 mm, preferably about 0.1 to 0.5 mm. The second threshold value $Th_{2x}$ is a value corresponding to a distance displacement of about 3 to 20 mm, preferably about 5 to 10 mm. The third threshold value $Th_{3x}$ is a value corresponding to a distance displacement of about 300 to 700 mm, preferably about 400 to 600 mm, more preferably about 450 to 550 mm. Also, each of the threshold values may be set to different values for each objective point 205, namely, for each distance sensor 211. The monitoring device 201 can thereby set proper threshold values for each distance sensor 211 and have improved judgment accuracy.

When the reference position is set as shown in FIG. 28, the first threshold value $Th_{1x}$ is a value corresponding to a distance from the reference position of about 0.1 to 3 mm, preferably about 0.1 to 0.5 mm. The second threshold value $Th_{2x}$ is a value corresponding to a distance from the reference position of about 3 to 20 mm, preferably about 5 to 10 mm. The third threshold value $Th_{3x}$ is a value corresponding to a distance from the reference position of about 300 to 700 mm, preferably about 400 to 600 mm, more preferably about 450 to 550 mm. In this case, the reference positions of the first threshold value $Th_{1x}$ and the second threshold value $Th_{2x}$ must be corrected depending upon the spot on the sleeping person 202 where the light flux is incident. However, the reference position of the third threshold value $Th_{3x}$ can be a fixed position (a position on the upper surface of the bed 206, for example) and is easy to use.

The determination part 223 is configured to determine that the sleeping person 202 has had a first change in shape when the distance showed a change over time which is not smaller than the first threshold value $Th_{1x}$ and not greater than the second threshold value $Th_{2x}$. The determination part 223 is configured to determine that the sleeping person 202 has had a second change in shape, which is different from the first change in shape, when the distance showed a change over time which is greater than the second threshold value $Th_{2x}$ and not greater than the third threshold value $Th_{3x}$. The first change in shape in this embodiment is small motion of the sleeping person 202 such as respiration, abnormal respiration or spasm. This is the state designated as 153 or 154 in FIG. 27, for example. The second change in shape in this embodiment is large motion of the sleeping person 202 such as rolling. This is the state designated as 155 in FIG. 27, for example.

The determination part 223 is configured to determine that the sleeping person 202 has had a third change in shape when periodic changes in the distance with time are detected. The determination is preferably made while the first change is determined to be continuing. The third change in shape in this embodiment is respiration of the sleeping person 202 including normal and periodic abnormal respirations. This is the state designated as 154 in FIG. 27. In the example shown in FIG. 27, since the predetermined period is about 15 seconds, the respiration does not appear as periodic changes.

The determination part 223 is preferably configured to determine that there has been a third change in shape by evaluating the period and amplitude of the periodic changes. To evaluate the period and amplitude of the periodic changes is to examine synchronism, for example. Namely, the determination part 223 examines the synchronism between the periodic changes and prescribed changes and determines that there has been a third change in shape when they are synchronized with each other. The prescribed changes are waveform patterns of normal or abnormal respirations, which will be described later with reference, for example, to FIG. 29. The accuracy in determining the presence or absence of respiration of the sleeping person 202 can be thereby improved, and the amount of calculation in the control part 221 can be reduced.

To examine the synchronism is to analyze the period (frequency) of changes in the distance with time using a high speed Fourier transform operation or the like and to evaluate whether the peak of the spectrum of the period within an objective period range (period range of respiration), for example, has a sharpness which is not lower than a certain level. The sharpness of the peak can be evaluated based on the ratio of the power of the period of changes over time in the distance to the total or average of the powers of the spectra within the objective period range.

The determination part 223 is configured to monitor the period of the periodic changes based on the detected periodic changes. To monitor the period of the periodic changes is to monitor the respiration rate of the sleeping person 202 per unit time, for example.

The determination part 223 is configured to determine that the sleeping person 202 has had a fourth change when the distance showed a change over time which exceeds the third threshold value $Th_{3x}$. The fourth change in shape in this embodiment is a motion of the sleeping person 202 which is greater than the second change in shape such as sitting-up. For example, this is the state designated as 152 in FIG. 27.

Also, the determination part 223 is configured to determine that the sleeping person 202 has deviated from the monitored region 250, namely has left the bed, when no change in shape of the sleeping person 202 can be detected within a first predetermined period of time after the distance has showed a change over time which exceeds the third threshold value $Th_{3x}$. This is the transition from the state designated as 152 to the state designated as 151 shown, for example, on the right side in FIG. 27. The first predetermined period of time is about 10 to 60 seconds, for example. In this case, the determination part 223 may be configured to determine that the sleeping person 202 has deviated from the monitored region 250 when the human detection sensor 241 detects the presence of the sleeping person 202 for a certain period of time and then cannot detect the presence of the sleeping person 202 after the transition from the state designated as 152 to the state designated as 151. The determination part 223 may be configured to make determination in combination with the detection of the presence or absence of the sleeping person 202 by the human detection sensor 241.

The determination part 223 may be configured to determine that the sleeping person 202 has deviated from the monitored region 250 when neither the first change in shape nor the second change in shape of the sleeping person 202 cannot be detected for a predetermined period of time or longer without detection of periodic changes after the distance has showed a change over time which exceeds the third threshold value $Th_{3x}$. The predetermined period of time is about 1 to 3 minutes, for example. For example, when the sleeping person 202 really leaves the bed after the changes over time have exceeded the third threshold value $Th_{3x}$, the value of changes over time gradually decreases. Thus, judging only from the variation, the value causes in the range of motion or respiration for some time and then becomes zero. When noise is high, there may be a case in which the amplitude of change over time exceeds the first threshold value but the changes over time cannot be detected as respiration when the periodicity is evaluated. Thus, the determination on whether the sleeping person 202 has left the bed is made when neither the first change in shape nor the second change in shape can be detected. However, when periodic changes have been detected before this situation happens, it means that the sleeping person 202 has been in a quiet state after the distance had shown a change which exceeded the third threshold value $Th_{3x}$. Thus, when neither the first change in shape nor the second change in shape appear thereafter, the sleeping person 202 must be determined to be in a critical condition.

The determination part 223 may be configured to determine that the sleeping person 202 has deviated from the monitored region 250 when the distance sensors 211 corresponding to the objective points 251a, 251b, 251c, 254a, 254b, and 254c along the sides of the bed 206 (see FIG. 25) detect changes over time which are greater than those which the distance sensors 211 corresponding to the objective points 252a, 252b, 252c, 253a, 253b, and 253c at the center of the bed 206 (see FIG. 25) detect at the time when the distance shows a change over time which is greater than the third threshold value $Th_{3x}$. It is thereby possible to determine that the sleeping person 202 left the bed irrespective of time. This is because when the sleeping person 202 leaves the bed, the motion at a side of the bed 206 is greater than the motion at the center of the bed 206. Also, it is thereby possible to determine that the sleeping person 202 has left the bed even when it takes time for the sleeping person 202 to leave the bed.

Also, the determination part 223 is configured to determine that the sleeping person 202 is in the monitored region 250, namely the sleeping person 202 is in the bed 206, when changes in shape of the sleeping person 202 is determined to have continued for a second predetermined period of time. This is the case where the waveform makes the transition from the state designated as 151 to any one of the states designated as 152, 153, 154, and 155 shown on the left side in FIG. 27, and the, for example,state continues for a second predetermined period of time. The second predetermined period of time is about 30 to 60 seconds, for example. In this case, any one of the above states may appear or a plurality of the states may appear in sequence.

The determination part 223 may be configured to determine that the sleeping person 202 is in the monitored region 250, namely in the bed 206, when the distance has shown periodic changes over time for a predetermined period of time. The determination part 223 may be configured to start determining whether the sleeping person 202 is in a critical condition or not on condition that the sleeping person 202 is determined to be in the bed. The predetermined period of time must be long enough to detect the respiration stably, and it is typically 30 to 90 seconds.

The determination on whether the sleeping person 202 is in the bed or not may be made on condition that the human detection sensor 241 has detected the presence of the sleeping person 202. This is the state designated as 156 in FIG. 27.

The determination part 223 is configured to determine that the sleeping person 202 has no change in shape when the distance shows changes over time which is lower than the threshold value $Th_{1x}$ and to determine that the sleeping person 202 is in a critical condition when no change in shape has been detected for a third predetermined period of time after the sleeping person 202 has been determined to be in the monitored region 250. The first threshold value $Th_{1x}$ is set to remove noise in signals in this embodiment.

This is because the respiration of the sleeping person 202 can be determined to have been stopped or the sleeping person 202 may have fallen off the bed 206 since the sleeping person 202 is not determined to have left the bed but no changes in shape has been detected. This is the case where the waveform makes transition, for example, from the state designated as 154 to the state designated as 151 without passing through the state designated as 152 in FIG. 27. The reason why the determination is made after the third period of time has passed is that respiration may stop for a short period of time even if the sleeping person 202 is in a normal condition. The third predetermined period of time is about 60 second, for example.

The determination part 223 is configured to determine that the sleeping person 202 is in a critical condition when the second change in shape is determined to have continued for a fourth predetermined period of time. This is because the sleeping person 202 may be suffering and struggling for some reason when large motion of the sleeping person 202 does not stop in a short period of time but continues. This is the case where the state designated as 155 in FIG. 27 has continued for the fourth period of time. This determination is made to issue an alarm when the sleeping person 202 is suffering and struggling, for example. The fourth predetermined period of time is about 60 seconds, for example.

The determination part 223 may be configured to determine that the sleeping person 202 is in a critical condition when the second change in shape is determined to have continued for the fourth predetermined period of time after the third change in shape (respiration) is determined to have continued for a predetermined period of time. The predetermined period of time, which must be long enough to detect respiration with stability, is 30 to 120 seconds, for example. When the sleeping person 202 is doing something on the bed 206 immediately after entering the bed 206, or after the sleeping person 202 sits up once and lie again, the sleeping person 202 may be determined to be in a critical condition. Thus, the determination is made after it is determined that the sleeping person 202 has been in a quiet state and is breathing for the predetermined period of time.

The determination part 223 may be configured to determine that the sleeping person 202 has fallen off the bed 206 when it is determined that there is no changes in shape after the second change in shape has been detected in the objective points 251a, 251b, 251c, 254a, 254b, or 254c (see FIG. 25) along the sides of the bed 206.

The determination part 223 may be configured to determine that the sleeping person 202 is in a critical condition when the sleeping person 202 is determined to have deviated from the monitored region 250, namely when the sleeping person 202 is determined to have left the bed. The monitoring device 201 can thereby determine the fact that the sleeping person 202 who must stay in the bed has freely left the bed or is walking around when the device is installed in a hospital or a nursing facility. When the monitoring device 201 is installed in a personal home and this determination is not necessary, the determination part 223 is configured not to make the determination.

The determination part 223 is preferably configured to determine that the sleeping person 202 is in a critical condition when the respiration rate of the sleeping person 202 is not within a predetermined range. The predetermined range is about 10 to 25 times per minute.

The determination part 223 is preferably configured to determine that the sleeping person 202 is in a critical condition when the period of the waveform pattern becomes irregular within a short period of time or varies suddenly while the sleeping person 202 is determined to be breathing. This is because the sleeping person 202 may have a lung disease such as spontaneous hem thorax or bronchial asthma, a heart disease such as congestive heart failure, or a cerebrovascular disease such as cerebral bleeding.

The determination part 223 is configured to send an alarm signal to the alarm device 290 when the sleeping person 202 is determined to be in a critical condition.

The determination by the determination part 23 on the presence or absence of changes in shape of the sleeping person 202 is preferably made based on changes over time in the distances corresponding to the plurality of distance sensors 211 in a comprehensive manner. However, when there is no need to designate the objective points 205, the determination on the presence or absence of changes in shape may be made based on changes over time in the distance detected by one distance sensor 211 selected from the distance sensors 211.

When one distance sensor 211 is selected from the plurality of distance sensors 211, for example, the distance sensor 211 which detected the largest change over time in the distance within a predetermined period of time in the immediate past is preferably selected. Then, the determination on the presence or absence of changes in shape of the sleeping person 202 is made based on the changes over time in the distance corresponding to the selected distance sensor 211. In this case, it is good to select the distance sensor 211 which detected the largest variation in changes over time in the distance within a period of time for which the sleeping person 202 breathes a few times in the past (a few seconds to ten and some seconds). The change in shape of the sleeping person 202 are reflected in changes over time in the objective points 205 in different manners depending on the positions of the objective points 205 corresponding to the plurality of distance sensors 211. Thus, to detect minute changes like the third change in shape (respiration), the determination part 223 must select a distance sensor 211 which detected changes over time reflecting the minute changes properly.

Alternatively, a method may be used in which one or more distance sensors 211 which detected large changes over time are selected, each selected distance sensor thereof is subjected to frequency analysis, and the distance sensor 211 whose output has a frequency spectrum with the clearest peak is selected.

The thus selected distance sensor 211 may be changed when the sleeping person 202 makes motion such as rolling. In this case, a distance sensor 211 which detected the largest variation in changes over time within a few seconds after the sleeping person 202 has become quiet is selected again and, for example, respiration of the sleeping person 202 is detected. In this case, one period of the waveform pattern which the changes over time in the distance form corresponds to one breath. In detecting respiration, the total of changes over time in the distances obtained from all the distance sensors 211 may be used. In this case, the changes may be cancelled out since changes with different phased are added. Thus, the largest change described above are compared and the larger one is used. Alternatively, the frequency spectra of them are compared and the one with a clearer peak is used.

The determination part 223 can determine whether the sleeping person 202 is moving or not based on each of the changes over time in the distances corresponding to the plurality of distance sensors 211 respectively. In this case, the determination is made based on the transitions of the changes over time in each of the distances to the objective points 205. For example, the distances to the objective points 252a, 252b, and 252c in the center part (see FIG. 25) show large changes after the distances to the objective points 251a, 251b, and 251c on one side (see FIG. 25) have shown large changes, the sleeping person 202 can be determined to be moving from the edge to the center of the bed 206. Also, the moving speed can be calculated from the time differences among the changes.

Figure 29:
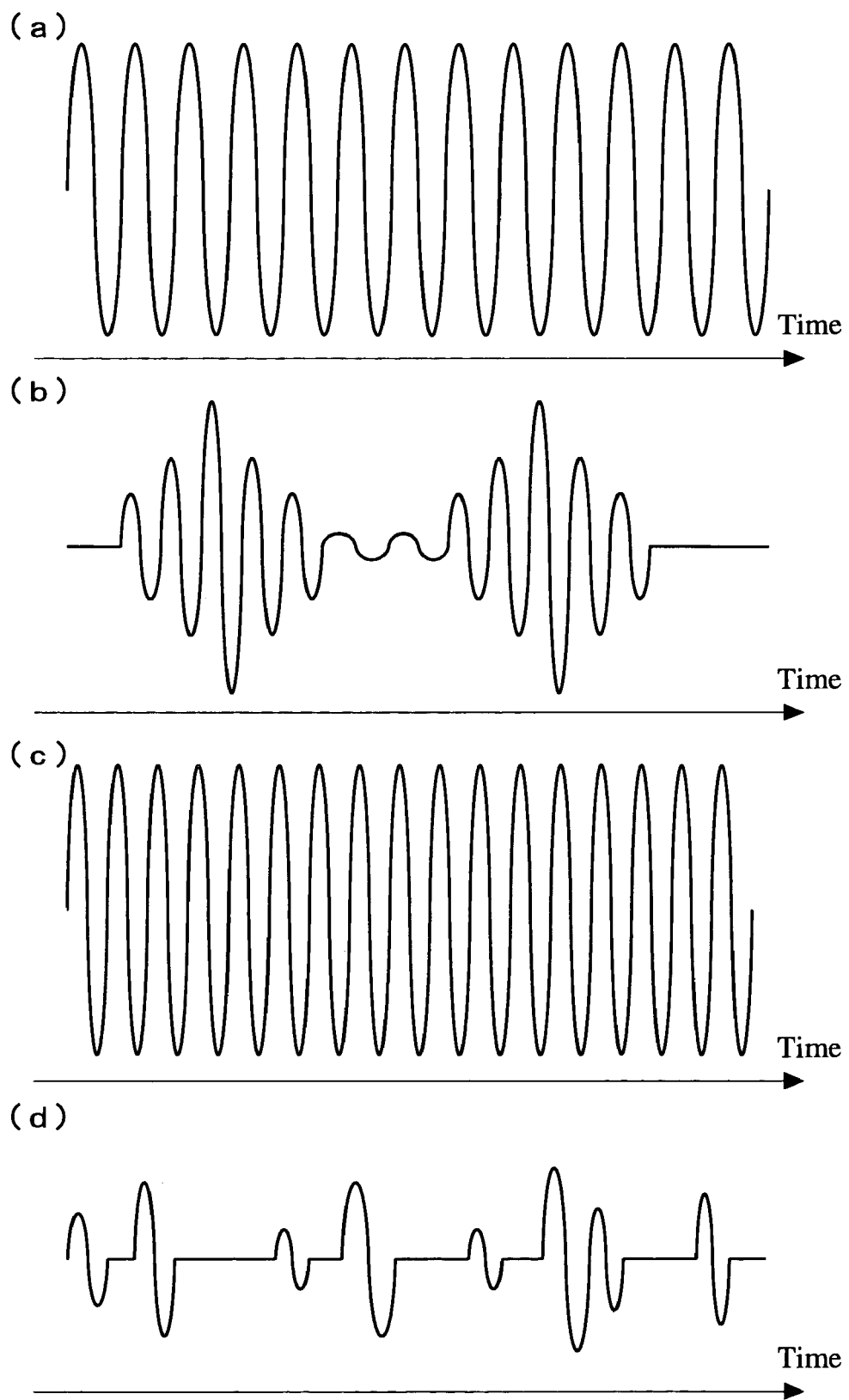
FIG. 29 is a schematic view illustrating normal and abnormal respiration waveform patterns for use in the second embodiment of this invention.

Description will be made of examples of normal and abnormal respiration waveform patterns with reference to FIG. 29. Normal respiration shows a waveform pattern similar to a sine wave as shown in FIG. 29(*a*). The waveform patterns of abnormal respiration are waveform patterns which are considered to occur when a sleeping person has a physiological defect such as Cheyne-Stokes respiration, central hyperventilation, ataxic respiration, and Kussmaul respiration. The above waveform patterns of abnormal respiration are examples and this invention is not limited thereto.

The monitoring device 201 may have a respiration pattern storage part 226 for storing the waveform patterns of normal respiration of the sleeping person 202 and the waveform patterns of abnormal respiration in the memory part 224. It is thereby possible to easily determine to which waveform pattern the respiration waveform pattern of the sleeping person 202 belongs. Also, a waveform pattern at the time when a sleeping person is having a spasm is preferably stored in the respiration pattern storage part 226 of the memory part 224. The determination part 223 can thereby determine that the sleeping person 202 is having a spasm when the first change in shape is detected.

FIG. 29(b), FIG. 29(c), and FIG. 29(d) show waveform patterns of Cheyne-Stokes respiration, central hyperventilation, and ataxic respiration, respectively.

FIG. 22 shows the names of diseases and the diseased sections which are considered to be the causes of the abnormal respiration waveform patterns shown above.

The determination part 223 determines to which waveform pattern the waveform pattern of the changes over time in distances belongs utilizing the fact that the respiration patterns have different frequencies, number of appearances, and amplitudes. Also, the determination part 223 determines that the sleeping person 202 is in a critical condition when the distance shows changes over time which belong to the above waveform patterns of abnormal respiration. The control part 221 may output the result of the determination from the output device 228. Here, the output includes the detected respiration rate and frequency of motions of the sleeping person 202, the name of the abnormal respiration pattern, the name of disease, the diseased organ, or the diseased section which is considered to be the cause of the abnormal respiration pattern, and so on.

The monitoring device 201, which has a plurality of distance sensors 211 in the above description, may have only one distance sensor 211. In this case, the monitoring device 201 can be simplified and downsized. Also, the monitoring device 201 can perform high-speed operation since the number of outputs from the distance sensor 211 is small.

When the monitoring device 201 has the pressure detection sensor 243 (see FIG. 26) in addition to the distance sensors 211, the reliability, for example, in determining whether the sleeping person 202 is in the bed or not can be improved by utilizing outputs from the pressure detection sensor 243.

The monitoring device 201 according to the second embodiment as described above can detect respiration of the sleeping person 202 reliably and determine changes of the sleeping person 202 such as being in the bed, leaving bed and respiratory arrest. The monitoring device 201 does not use image processing using a camera, which may give a psychologically uncomfortable feeling, and can perform high-speed processing although it is simple. In addition, since the monitoring device 201 issues an alarm when the sleeping person 202 is determined to be in a critical condition, life-saving measures can be quickly taken. This is advantageous when the monitoring device 201 is used for an aged person or a sick person.

INDUSTRIAL APPLICABILITY

As has been described above, the monitoring device comprises a plurality of independent distance sensors oriented to different positions respectively in a monitored target area for measuring the distance to a monitored target, a calculating unit for calculating each of changes over time in outputs from the plurality of distance sensors, and a detection processing part for detecting periodic changes of the monitored target based on changes over time relating to one or more of distance sensors selected from the plurality of distance sensors. Thus, there can be provided a monitoring device which can detect the condition of a sleeping person reliably and which is small and simple.

The invention claimed is:

1. A monitoring device comprising:
   a distance sensor installed facing monitored target area for measuring a distance to a monitored target;
   a calculating unit for calculating changes over time in the output of said distance sensor; and
   a detection processor for detecting changes in shape of said monitored target based on the calculated change over time,
   wherein said detection processor determines the condition of said monitored target based on either or both of the period and amplitude of periodic changes in said detected changes in shape.

2. A monitoring device comprising:
   multiple independent distance sensors installed facing different positions respectively within a monitored target area for measuring a distance to a monitored target;
   a calculating unit for calculating changes over time in the outputs of each of the multiple distance sensors; and
   a detection processor for detecting changes in shape of said monitored target based on the calculated changes over time in one or multiple selected distance sensors among the multiple sensors,
   wherein said detection processor selects an output which showed the largest change over time within a predetermined period of time in the immediate past and detects changes in shape of said monitored target based on change over time in said output.

3. A monitoring device comprising:
   multiple independent distance sensors installed facing different positions respectively within a monitored target area for measuring a distance to a monitored target;
   a calculating unit for calculating changes over time in the outputs of each of the multiple distance sensors; and
   a detection processor for detecting changes in shape of said monitored target based on the calculated changes over time in one or multiple selected distance sensors among the multiple sensors,
   wherein said detection processor selects all of said multiple distance sensors, obtains the total of changes over time in the distances, and detects changes in shape of said monitored target based on said total.

4. A monitoring device comprising:
   multiple independent distance sensors installed facing different positions respectively within a monitored target area for measuring a distance to a monitored target;
   a calculating unit for calculating changes over time in the outputs of each of the multiple distance sensors; and
   a detection processor for detecting changes in shape of said monitored target based on the calculated changes over time in one or multiple selected distance sensors among the multiple sensors,
   wherein said detection processor calculates the frequency spectra of all the outputs from said multiple distance sensors, selects a distance sensor whose output has a frequency spectrum with a peak having a sharpness which is a predetermined value or higher and the highest among the calculated frequency spectra, and detects changes in shape of said monitored target based on changes over time in the selected distance sensor.

5. A monitoring device comprising:

multiple independent distance sensors installed facing different positions respectively within a monitored target area for measuring a distance to a monitored target;

a calculating unit for calculating changes over time in the outputs of each of the multiple distance sensors; and a detection processor for detecting changes in shape of said monitorecPtarget based on the calculated changes over time in one or multiple selected distance sensors among the multiple sensors, wherein said detection processor calculates the frequency spectra of outputs from the distance sensors which detected a change over time having an absolute value within a predetermined range, selects a distance sensor whose output has a frequency spectrum with a peak having a sharpness which is a predetermined value or higher and the highest among the calculated frequency spectra, and detects changes in shape of said monitored target based on changes over time in the selected distance sensor.

6. A monitoring device comprising:

multiple independent distance sensors installed facing different positions respectively within a monitored target area for measuring a distance to a monitored target;

a calculating unit for calculating changes over time in the outputs of each of the multiple distance sensors; and a detection processor for detecting changes in shape of said monitored target based on the calculated changes over time in one or multiple selected distance sensors among the multiple sensors, wherein said detection processor calculates the frequency spectra of outputs from a plurality of the distance sensors which detected a change over time having one of the largest absolute values, selects a distance sensor whose output has a frequency spectrum with a peak having a sharpness which is a predetermined value or higher and the highest among said calculated frequency spectra, and detects changes in shape of said monitored target based on changes over time in the selected distance sensor.

7. A monitoring device comprising:

multiple independent distance sensors installed facing different positions respectively within a monitored target area for measuring a distance to a monitored target;

a calculating unit for calculating changes over time in the outputs of each of the multiple distance sensors; and a detection processor for detecting changes in shape of said monitored target based on the calculated changes over time in one or multiple selected distance sensors among the multiple sensors, wherein said detection processor selects changes over time having absolute values which are larger than a predetermined value and detects change in shape of said monitored target based on the average of said selected changes over time.

8. A monitoring device comprising:

multiple independent distance sensors installed facing different positions respectively within a monitored target area for measuring a distance to a monitored target;

a calculating unit for calculating changes over time in the outputs of each of the multiple distance sensors; and a detection processor for detecting changes in shape of said monitored target based on the calculated changes over time in one or multiple selected distance sensors among the multiple sensors, wherein said detection processor selects changes over time having absolute values which are larger than a predetermined value and detects changes in shape of said monitored target based on the average of said absolute values of the selected changes over time.

9. A monitoring device comprising:

multiple independent distance sensors installed facing different positions respectively within a monitored target area for measuring a distance to a monitored target;

a calculating unit for calculating changes over time in the outputs of each of the multiple distance sensors; and a detection processor for detecting changes in shape of said monitored target based on the calculated changes over time in one or multiple selected distance sensors among the multiple sensors, wherein said detection processor compares the phases of changes over time relating to a plurality of the selected distance sensors each other, classifies said changes over time into groups according to the similarity of said phases, obtains the total of said changes over time in each group, calculates the difference between the totals of groups, the groups having approximately opposite phases each other, and detects changes in shape of said monitored target based on the value obtained by said calculation.

10. A monitoring device comprising:

a distance sensor installed facing monitored target area for measuring a distance to a monitored target;

a calculating unit for calculating changes over time in the output of said distance sensor; and a detection processor for detecting changes in shape of said monitored target based on the calculated change over time, wherein said distance sensor has light emitting means for emitting a light flux to said monitored target and an imaging optical system for forming an image of a light emission pattern generated on said monitored target by said light emitting means, and obtains an output corresponding to the distance by trigonometry based on the position where imaging pattern light is formed into an image by said imaging optical system.

11. A monitoring device comprising:

multiple independent distance sensors installed facing different positions respectively within a monitored target area for measuring a distance to a monitored target;

a calculating unit for calculating changes over time in the outputs of each of the multiple distance sensors; and a detection processor for detecting changes in shape of said monitored target based on the calculated changes over time in one or multiple selected distance sensors among the multiple sensors, wherein said distance sensor has light emitting means for emitting a light flux to said monitored target and an imaging optical system for forming an image of a light emission pattern generated on said monitored target by said light emitting means, and obtains an output corresponding to the distance by trigonometry based on the position where imaging pattern light is formed into an image by said imaging optical system.

12. A monitoring device comprising: a distance sensor installed facing monitored target area for measuring a distance to a monitored target;

a calculating unit for calculating changes over time in the output of said distance sensor; and a detection processor for detecting changes in shape of said monitored target based on the calculated change over time, wherein said distance sensor has at least two imaging units for forming images of said monitored target with individual optical axes and obtains an output corresponding to the distance by trigonometry based on information on the position where said images are formed from said imaging units.

13. A monitoring device comprising:

multiple independent distance sensors installed facing different positions respectively within a monitored target area for measuring a distance to a monitored target;

a calculating unit for calculating changes over time in the outputs of each of the multiple distance sensors; and a detection processor for detecting changes in shape of said monitored target based on the calculated changes over time in one or multiple selected distance sensors among the multiple sensors, wherein said distance sensor has at least two imaging units for forming images of said monitored target with individual optical axes and obtains an output corresponding to the distance by trigonometry based on information on the position where said images are formed from said imaging units.

14. A monitoring method comprising the steps of:

measuring a distances to multiple different positions within a monitored target area to measure the distances to a monitored target changing in shape within said monitored area;

calculating changes over time in the multiple distances; and detecting changes in shape of said monitored target based on the calculated changes over time in one or multiple selected distances among changes over time, wherein an output which showed the largest change over time within a predetermined period of time in the immediate past is selected and changes in shape of said monitored target are detected based on change over time in said output in said step of detecting.

15. A monitoring method comprising the steps of:

measuring a distances to multiple different positions within a monitored target area to measure the distances to a monitored target changing in shape within said monitored area;

calculating changes over time in the multiple distances; and detecting changes in shape of said monitored target based on the calculated changes over time in one or multiple selected distances among changes over time, wherein changes over time having absolute values which are larger than a predetermined value are selected and changes in shape of said monitored target are detected based on the average of the selected changes over time in said step of detecting.

16. A monitoring method comprising the steps of:

measuring a distances to multiple different positions within a monitored target area to measure the distances to a monitored target changing in shape within said monitored area;

calculating changes over time in the multiple distances; and detecting changes in shape of said monitored target based on the calculated changes over time in one or multiple selected distances among changes over time, wherein changes over time having absolute values which are larger than a predetermined value are selected and changes in shape of said monitored target are detected based on the average of said absolute values of said selected changes over time in said step of detecting.

17. A monitoring method comprising the steps of:

measuring a distances to multiple different positions within a monitored target area to measure the distances to a monitored target changing in shape within said monitored area;

calculating changes over time in the multiple distances; and detecting changes in shape of said monitored target based on the calculated changes over time in one or multiple selected distances among changes over time, wherein each of the phases of changes over time relating to the multiple distances are compared to each other, said changes are classified into groups according to the similarity of said phases, the total of said changes over time in each group is obtained, the difference between the totals of groups, the groups having approximately opposite phases each other, is calculated, and changes in shape of said monitored target are detected based on the value obtained by the calculation in said step of detecting.

18. A monitoring device comprising:

a distance sensor for measuring a distance to a monitored target in a monitored target area;

a calculating unit for calculating changes in output from said distance sensor over time; and detection processor for detecting changes in shape of said monitored target based on the calculated changes over time;

wherein said distance sensor has light emitting means for emitting a light flux to said monitored target, an imaging optical system for forming an image of a light emission pattern generated on said monitored target by said light emitting means, and a light receiving surface installed in the vicinity of the position where said imaging optical system forms an image and divided into a plurality of light receiving regions for receiving imaging pattern light from said formed image of said light emission pattern; and further has a position information output unit for receiving signals from said light receiving regions, comparing the intensities of imaging pattern light incident on said light receiving regions each other based on the receive signals, and outputting information on the position where an imaging pattern is formed corresponding to the distance to said monitored target.

19. The monitoring device as recited in claim 18, wherein said monitored target is an object which changes periodically, and wherein said detection processor monitors the period of the periodic changes based on the detected changes in shape of said monitored target.

20. The monitoring device as recited in claim 18, having a plurality of said distance sensors, said plurality of distance sensors being independent and installed facing different positions in said monitored target area.

21. The monitoring device as recited in claim 20, wherein said detection processor selects a distance sensor which detected the largest change over time within a predetermined period of time in the immediate past and detects changes in shape of said monitored target based on said change over time.

22. A monitoring device comprising:

a distance sensor for measuring a distance to a monitored target in a monitored target area;

a calculating unit for calculating changes in the output from said distance sensor over time; and detection processor for detecting changes in shape of said monitored target based on the calculated changes over time;

wherein said distance sensor has light emitting means for emitting a light flux to said monitored target, an imaging optical system for forming an image of a light emission pattern generated on said monitored target by said light emitting means, light receiving means disposed in the vicinity of the position where said imaging optical system forms an image for receiving imaging pattern light from said formed image of said light emission pattern; and a position information output unit for outputting information on the position where an imaging pattern is formed corresponding to the distance to said monitored target based on the position where imaging pattern light is formed into an image on said light receiving means.

23. The monitoring device as recited in claim 22, wherein said monitored target is an object which changes periodically, and wherein said detection processor monitors the period of the periodic changes based on the detected changes in shape of said monitored target.

24. The monitoring device as recited in claim 22, having a plurality of said distance sensors, said plurality of distance sensors being independent and installed facing different positions in said monitored target area.

25. The monitoring device as recited in claim 24, wherein said detection processor selects a distance sensor which detected the largest change over time within a predetermined period of time in the immediate past and detects changes in shape of said monitored target based on said change over time.

26. A monitoring device, comprising:

a sensor for detecting a variable correlating to a distance to an monitored target in a monitored target area;

a calculating unit for calculating a distance-related value based on said variable output from said sensor;

a determination unit for determining if there are changes in the shape of said monitored target based on the calculated distance-related value;

wherein said determination unit determines that said monitored target has had a first change in shape when said distance-related value is the same or larger than a first threshold, and lower than a second threshold, with said second threshold being larger than said first threshold; and wherein said determination unit determines that said monitored target has had a second change in shape, which is different from said first change in shape, when said distance-related value is the same or larger than a second threshold value, and lower than a third threshold, with said third threshold being larger than said second threshold.

27. A monitoring device as recited in claim 26, wherein said determination unit determines that the monitored target has deviated from said monitored target area when no change in shape of said monitored target can be detected within a first predetermined period of time after said distance-related value has exceeded said third threshold value.

28. The monitoring device as recited in claim 26, wherein said determination unit determines that the monitored target has deviated from said monitored target area when neither said first change in shape nor said second change in shape of said monitored target can be detected for a predetermined period of time or longer without detection of periodic changes after said distance-related value has exceeded said third threshold value.

29. The monitoring device as recited in claim 26, wherein said determination unit determines that there has been a third change in shape when periodic changes in said distance-related value are detected.

30. The monitoring device as recited in claim 26, wherein said determination unit determines that said monitored target is in said monitored target area when changes in shape of said monitored target are determined to have continued for a second predetermined period of time.

31. The monitoring device as recited in claim 30, wherein said determination unit determines that said monitored target has no change in shape when said distance-related value is lower than said first threshold value and determines that said monitored target is in a critical condition when said monitored target is determined to have had no change in shape for a third predetermined period of time after said monitored target has been determined to be in said monitored target area.

32. The monitoring device as recited in claim 31, further comprising alarm means, wherein said determination unit sends an alarm signal to said alarm means when said monitored target is determined to be in a critical condition.

33. The monitoring device as recited in claim 26, wherein said determination unit determines that said monitored target is in said monitored target area when periodic changes in said distance-related value has been detected for a predetermined period of time or longer.

34. The monitoring device as recited in claim 33, wherein said determination unit determines that said monitored target has no change in shape when said distance-related value is lower than said first threshold value and determines that said monitored target is in a critical condition when said monitored target is determined to have had no change in shape for a third predetermined period of time after said monitored target has been determined to be in said monitored target area.

35. The monitoring device as recited in claim 34, further comprising alarm means, wherein said determination unit sends an alarm signal to said alarm means when said monitored target is determined to be in a critical condition.

36. The monitoring device as recited in claim 26, wherein said determination unit determines that said monitored target is in a critical condition when said second change in shape is determined to have continued for a fourth predetermined period of time.

37. The monitoring device as recited in claim 26, wherein the determination unit determines that said monitored target has had a fourth change in shape when said distance-related value exceeds said third threshold value.

38. The monitoring device as recited in claim 26, wherein the calculated distance-related value is changes over time in said variable or the absolute value of said changes over time.

39. The monitoring device as recited in claim 26, wherein said sensor has light emitting means for emitting a light flux to said monitored target, an imaging optical system for forming an image of a light emission pattern generated on said monitored target by said light emitting means, a light receiving surface disposed in the vicinity of the position where said imaging optical system forms an image and divided into a plurality of light receiving regions for receiving imaging pattern light from the formed image of said light emission pattern; and a position information output unit for receiving signals from said light receiving regions, comparing the intensities of imaging pattern lights incident on said light receiving regions based on said receiving signals, and outputting information on the position where an imaging pattern is formed corresponding to the distance to said monitored target.

40. The monitoring device as recited in claim 26, wherein said sensor has light emitting means for emitting a light flux to said monitored target, an imaging optical system for forming an image of light emission pattern generated on said monitored target by said light emitting means, light receiving means disposed in the vicinity of the position where said imaging optical system forms an image for receiving imaging pattern light from said formed image of said light emission pattern; and a position information output unit for outputting information on the position where an imaging pattern is formed corresponding to the distance to said monitored target based on the position where imaging pattern light is formed into an image on said light receiving means.

41. The monitoring device as recited in claim 26, having a plurality of said sensors.

42. A monitoring device, comprising:
a sensor for detecting a variable correlating to the distance to a monitored target in a monitored target area;
a calculating unit for calculating a distance-related value based on said variable output from said sensor;
a determination unit for determining if there are changes in the shape of said monitored target based on said calculated distance-related value;
wherein said determination unit determines that said monitored target has deviated from said monitored target area when no change in shape of said monitored target can be detected within a first predetermined period of time after said distance-related value has exceeded a third threshold.

43. The monitoring device as recited in claim 42, wherein the determination unit determines that said monitored target has had a fourth change in shape when said distance-related value exceeds said third threshold value.

44. The monitoring device as recited in claim 42, wherein the calculated distance-related value is changes over time in said variable or the absolute value of said changes over time.

45. The monitoring device as recited in claim 42, wherein said sensor has light emitting means for emitting a light flux to said monitored target, an imaging optical system for forming an image of a light emission pattern generated on said monitored target by said light emitting means, a light receiving surface disposed in the vicinity of the position where said imaging optical system forms an image and divided into a plurality of light receiving regions for receiving imaging pattern light from the formed image of said light emission pattern; and a position information output unit for receiving signals from said light receiving regions, comparing the intensities of imaging pattern lights incident on said light receiving regions based on said receiving signals, and outputting information on the position where an imaging pattern is formed corresponding to the distance to said monitored target.

46. The monitoring device as recited in claim 42, wherein said sensor has light emitting means for emitting a light flux to said monitored target, an imaging optical system for forming an image of light emission pattern generated on said monitored target by said light emitting means, light receiving means disposed in the vicinity of the position where said imaging optical system forms an image for receiving imaging pattern light from said formed image of said light emission pattern; and a position information output unit for outputting information on the position where an imaging pattern is formed corresponding to the distance to said monitored target based on the position where imaging pattern light is formed into an image on said light receiving means.

47. The monitoring device as recited in claim 42, having a plurality of said sensors.

48. A monitoring device, comprising:
multiple independent distance sensors installed facing different positions respectively within a monitored target area for measuring the distances to an monitored target;
a calculating unit for calculating changes over time in respectively the outputs from the multiple distance sensors; and
a detection processor for selecting the distance sensor which detected the largest change over time within a predetermined period of time in the immediate past, and detect changes in shape of said monitored target based on changes over time detected by said selected distance sensor;
wherein said detection processor selects a distance sensor which detected the largest change over time within a predetermined period of time after said monitored target has been in a quiet state, and detects changes in the shape of said monitored target based on changes over time detected by the selected distance sensor when movement of said monitored target has been detected.

* * * * *